(12) United States Patent
Sullivan et al.

(10) Patent No.: US 9,060,760 B2
(45) Date of Patent: Jun. 23, 2015

(54) TISSUE REMOVAL SYSTEM

(75) Inventors: Roy H. Sullivan, Uxbridge, MA (US); Ronald D. Adams, Holliston, MA (US); Andrew Barnes, Naugatuck, CT (US); Jeffrey Radziunas, Wallingford, CT (US); Joe Paul, Thomaston, CT (US); Paul DiCesare, Easton, CT (US)

(73) Assignee: HOLOGIC, INC., Marlborough, MA (US)

( * ) Notice: Subject to any disclaimer, the term of this patent is extended or adjusted under 35 U.S.C. 154(b) by 495 days.

(21) Appl. No.: 13/589,003

(22) Filed: Aug. 17, 2012

(65) Prior Publication Data

US 2013/0046316 A1 Feb. 21, 2013

Related U.S. Application Data

(60) Provisional application No. 61/524,991, filed on Aug. 18, 2011.

(51) Int. Cl.
| A61B 17/32 | (2006.01) |
|---|---|
| A61B 10/02 | (2006.01) |
| A61M 1/00 | (2006.01) |
| A61B 10/04 | (2006.01) |

(Continued)

(52) U.S. Cl.
CPC ......... *A61B 10/0275* (2013.01); *A61B 10/0266* (2013.01); *A61B 2010/0208* (2013.01); *A61B 10/0283* (2013.01); *A61B 10/0291* (2013.01); *A61B 10/04* (2013.01); *A61B 17/320016* (2013.01); *A61B 2010/0225* (2013.01); *A61B 2017/00389* (2013.01); *A61B 2017/320028* (2013.01); *A61B 2017/320064* (2013.01); *A61B 19/5202* (2013.01); *A61B 2017/00685* (2013.01); *A61B 2017/4216* (2013.01);

(Continued)

(58) Field of Classification Search
CPC .......... A61B 10/02; A61B 2010/0208; A61B 2010/0225; A61B 10/0266; A61B 10/0275; A61B 10/0291; A61B 10/04; A61B 10/0283; A61B 17/42; A61B 2017/4216; A61B 2217/005; A61B 17/32; A61B 17/320016; A61B 2017/320028; A61B 2017/320064
USPC .................................. 606/119, 167, 170, 171
See application file for complete search history.

(56) References Cited

U.S. PATENT DOCUMENTS

| 5,505,210 A | 4/1996 | Clement |
|---|---|---|
| 8,162,850 B2 | 4/2012 | Parihar et al. |
| 2010/0152611 A1 | 6/2010 | Parihar et al. |
| 2010/0312140 A1 | 12/2010 | Smith et al. |

OTHER PUBLICATIONS

International Search Report and Written Opinion for International Application No. PCT/US2012/051487, Applicant Hologic, Inc., Forms PCT/ISA/210, 220, and 237, dated Jan. 18, 2013 (20 pages).

(Continued)

*Primary Examiner* — Jonathan W Miles
(74) *Attorney, Agent, or Firm* — Vista IP Law Group LLP

(57) ABSTRACT

A tissue removal device includes an outer tubular member coupled to a housing and a having a tissue resection window, an inner tubular member slidably disposed within the outer tubular member, a tissue trap having a sealed interior in fluid communication with a vacuum chamber, an open proximal end of the inner tubular member being disposed within the tissue trap interior, and an actuator moveably coupled to the housing and operatively connected to a movable piston in the vacuum chamber, such that movement of the actuator relative to the housing generates a vacuum in the tissue trap.

14 Claims, 41 Drawing Sheets

(51) Int. Cl.
  *A61B 17/00* (2006.01)
  *A61B 19/00* (2006.01)
  *A61B 17/42* (2006.01)

(52) U.S. Cl.
  CPC .... *A61B 2217/005* (2013.01); *A61B 2217/007* (2013.01); *A61M 1/0047* (2013.01)

(56) References Cited

OTHER PUBLICATIONS

Invitation to Pay Additional Fees for International Application No. PCT/US2012/051487, Applicant Hologic, Inc., Form PCT/ISA/206 and Annex to Form PCT/ISA/206, dated Nov. 14, 2012 (8 pages).

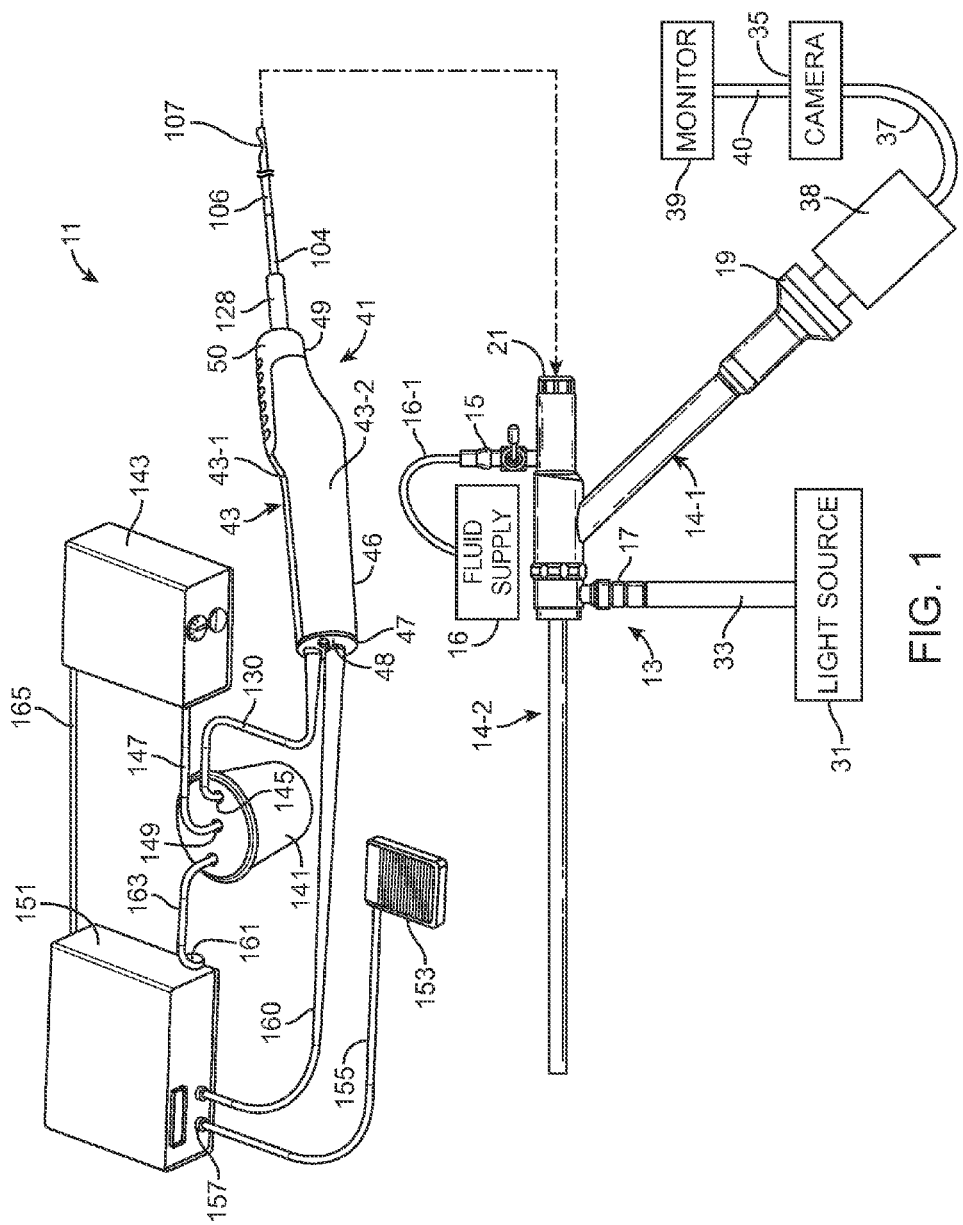

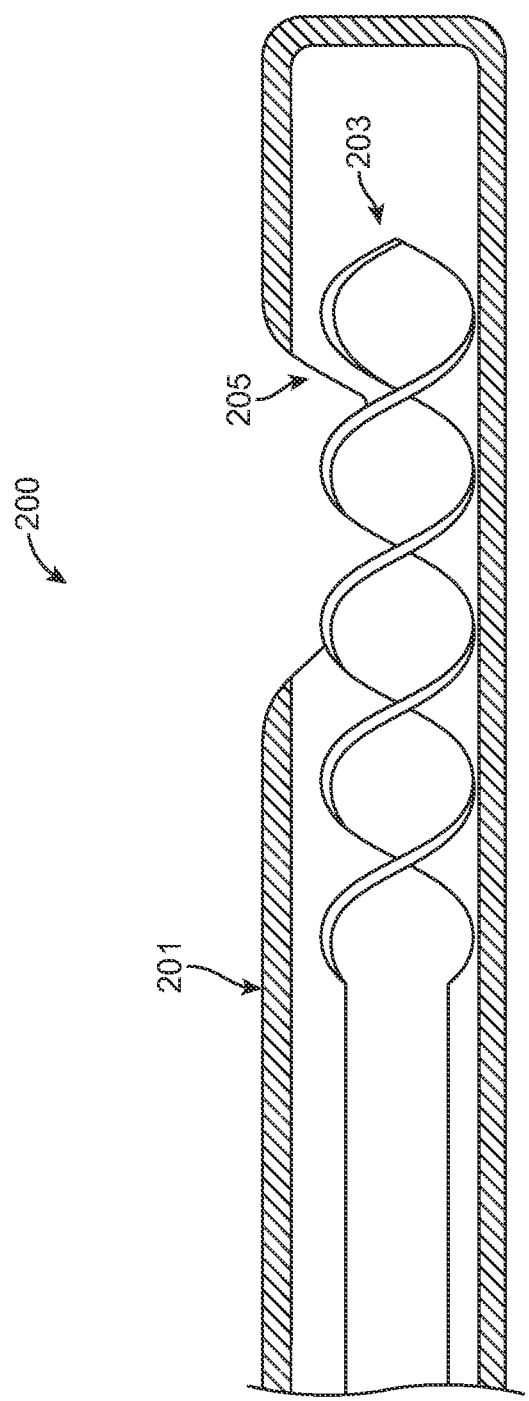

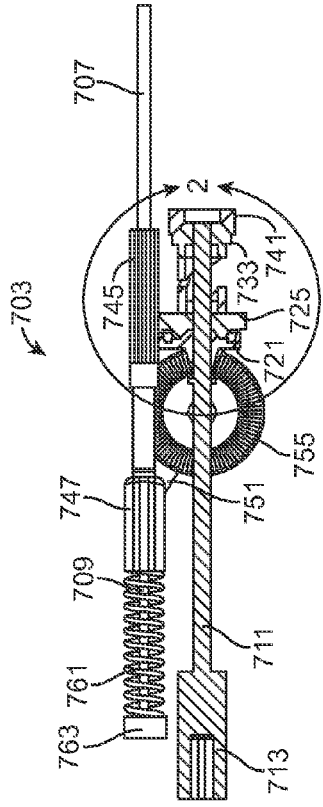
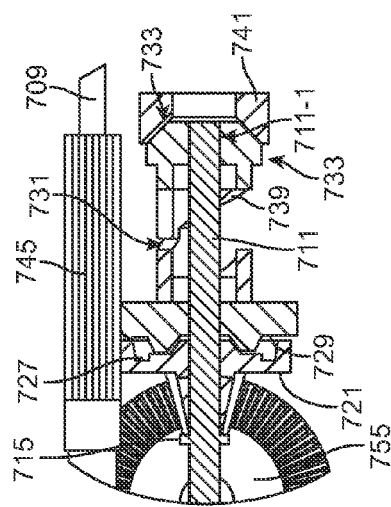
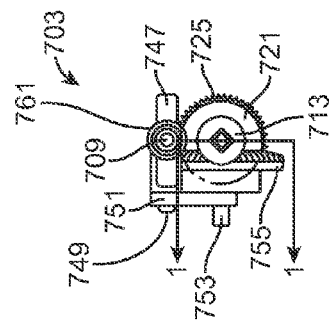
FIG. 21(c)
FIG. 21(d)
FIG. 21(b)

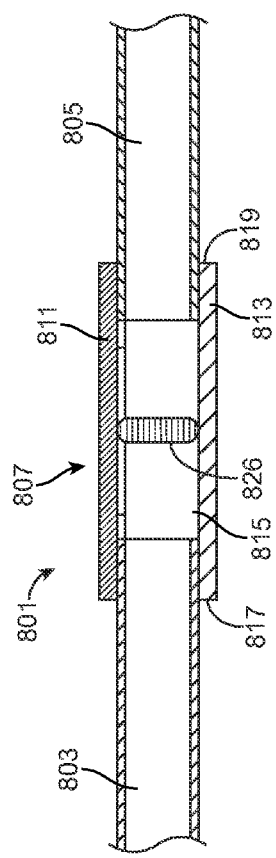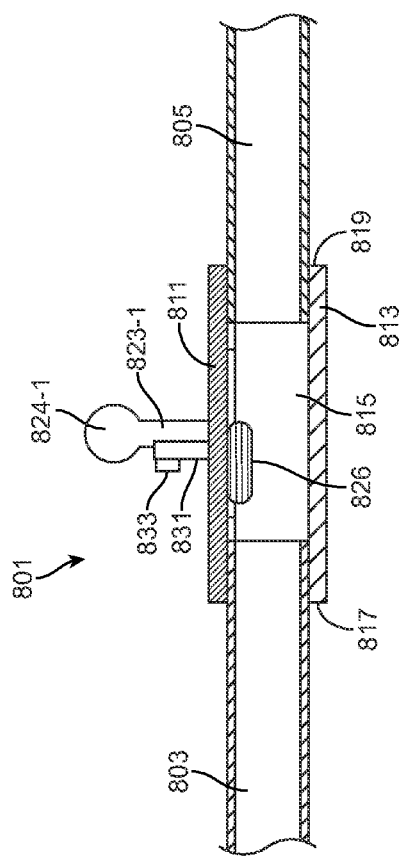

TISSUE REMOVAL SYSTEM

RELATED APPLICATION DATA

The present application claims the benefit under 35 U.S.C. §119 to U.S. Provisional Patent application No. 61/524,991, filed Aug. 18, 2011. The foregoing application is hereby incorporated by reference into the present application in its entirety.

FIELD

The disclosure relates generally to methods, systems and devices for surgical procedures, and relates more particularly to tissue removal systems for the removal of uterine fibroids and other abnormal gynecological tissues.

BACKGROUND

There are many situations in which it is desirable to remove unwanted tissue from a patient. Uterine fibroids and uterine polyps represent two such types of unwanted tissue. Uterine fibroids are well-defined, non-cancerous tumors that are commonly found in the smooth muscle layer of the uterus. Uterine polyps are wispy masses that are commonly found extending from the inner lining of the uterus. In many instances, uterine fibroids and uterine polyps can grow to be several centimeters in diameter and may cause symptoms like menorrhagia (prolonged or heavy menstrual bleeding), pelvic pressure or pain, and reproductive dysfunction. It is believed that uterine fibroids occur in a substantial percentage of the female population, perhaps in at least 20 to 40 percent of all women, and that uterine polyps occur in up to 10 percent of all women.

One type of treatment for uterine fibroids and uterine polyps is hysteroscopic resection. Hysteroscopic resection typically involves inserting a hysteroscope (i.e., an imaging scope) into the uterus through the vagina, i.e., transcervically, and then cutting away the unwanted tissue from the uterus using a device delivered to the unwanted tissue by the hysteroscope. Hysteroscopic resections typically fall into one of two varieties. In one variety, an electrocautery device in the form of a loop-shaped cutting wire is fixedly mounted on the distal end of the hysteroscope. The combination of the hysteroscope and the electrocautery device is typically referred to as a resectoscope. The transmission of electrical current to the uterus with a resectoscope is typically monopolar, and the circuit is completed by a conductive path to the power unit for the device through a conductive pad applied to the patient's skin. In this manner, tissue is removed by contacting the loop with the part of the uterus wall of interest. Examples of such devices are disclosed, for example, in U.S. Pat. No. 5,906, 615, inventor Thompson, issued May 25, 1999.

In the other variety of hysteroscopic resection, an electromechanical cutter is inserted through a working channel in the hysteroscope. The electromechanical cutter typically includes (i) a tubular member having a window through which tissue may enter and (ii) a cutting instrument positioned within the tubular member for cutting the tissue that has entered the tubular member through the window. In use, the cutter is positioned near the part of the uterus wall of interest. Tissue is then drawn, typically by suction, into the window, and then the tissue drawn into the window is cut with the cutting instrument. Examples of the electromechanical cutter variety of hysteroscopic resection are disclosed in, for example, U.S. Pat. No. 7,226,459, inventors Cesarini et al., issued Jun. 5, 2007; U.S. Pat. No. 6,032,673, inventors Savage et al., issued Mar. 7, 2000; U.S. Pat. No. 5,730,752, inventors Alden et al., issued Mar. 24, 1998; U.S. Patent Application Publication No. US 2009/0270898 A1, inventors Chin et al., published Oct. 29, 2009; U.S. Patent Application Publication No. US 2009/0270812 A1, inventors Litscher et al., published Oct. 29, 2009; U.S. Patent Application Publication No. US 2006/0047185 A1, inventors Shener et al., published Mar. 2, 2006; and PCT International Publication No. WO 99/11184, published Mar. 11, 1999, all of which are incorporated herein by reference.

In both of the above-described varieties of hysteroscopic resection, prior to tissue removal, the uterus is typically distended to create a working space within the uterus. Such a working space typically does not exist naturally in the uterus because the uterus is a flaccid organ. As such, the walls of the uterus are typically in contact with one another when in a relaxed state. The conventional technique for creating such a working space within the uterus is to administer a fluid to the uterus through the hysteroscope under sufficient pressure to cause the uterus to become distended. Examples of the fluid used conventionally to distend the uterus include gases like carbon dioxide or, more commonly, liquids like water or certain aqueous solutions (e.g., a saline or other physiologic solution or a sugar-based or other non-physiologic solution).

One of the benefits of fluid distension is the tamponade effect that the distension fluid provides on resected vascular tissue. Since the distension fluid is typically maintained at a pressure that exceeds the patient's mean arterial pressure (MAP), the fluid pressure provided by the distension fluid prevents the leakage of arterial blood from the resected tissue from flowing or oozing into the uterine cavity. When arterial blood flows or oozes into the cavity, it mixes with the distension fluid and renders visualization more difficult and, if not constrained, the flowing or oozing blood will force the suspension of the procedure. Thus, maintenance of fluid pressure above the intracavity arterial pressure is critical for the maintenance of a clear visual field.

Nevertheless, one shortcoming with existing hysteroscopic tissue removal systems, particularly of the electromechanical cutter variety, is that it is often difficult to maintain fluid distension of the uterus during the resection procedure. This is because such systems typically employ a vacuum source that continuously subjects the electromechanical cutter to suction, even when the cutting mechanism of the electromechanical cutter is not switched on. The purpose of such suction is to draw tissue into the cutter, typically through the window, and to facilitate the removal of resected tissue from the uterus. However, such suction also typically has the unwanted effect of removing some of the distending fluid from the uterus along with the resected tissue. Moreover, because suction is continuously applied to the cutter, even when the cutting mechanism is not being operated, fluid tends to be continuously removed from the uterus whenever the cutter is inserted into the patient. If such fluid cannot be replenished quickly enough, the fluid pressure within the uterus may drop to an undesired level. In particular, a steep drop in uterine fluid pressure will result in the leakage of blood into the uterine cavity, causing a loss of visualization and ultimately stoppage of the procedure if the surgeon can no longer properly visualize the treatment site. Moreover, depending on the extent and speed of the drop in uterine fluid pressure, there may be a significant lapse of time before the uterine fluid pressure can be restored to a desired level such that adequate visualization is possible. Such lapses in time are clearly undesirable as they interrupt the resection procedure, as well as lengthen the overall time for the procedure and increase the risk that distending fluid may be taken up by a blood vessel in the uterus, i.e., intravasation, which uptake may be quite harmful to the patient.

One approach to the above problem has been to provide the electromechanical cutter with a mechanism actuated by an electrical switch that causes the window in the cutter to be closed off when the cutting mechanism is turned off. In this manner, when the cutting mechanism is switched off, distension fluid from the uterus cannot escape from the uterus through the resection window of the cutter, and adequate uterine fluid pressure may be maintained. Unfortunately, however, the cost of the aforementioned electrical switch, as well as the cost of several other components of the cutter, may make the cost of the above-described electromechanical cutter prohibitive for certain procedures, such as polypectomies, for which the costs covered by most insurers are typically relatively low.

SUMMARY

In accordance with one embodiment of the disclosed inventions, a tissue removal device comprises a housing; an outer tubular member coupled to the housing and having a distal portion including a tissue resection window; an inner tubular member slidably disposed within the outer tubular member and defining an inner lumen extending from an open distal end to an open proximal end, the open distal end comprising a cutting edge to sever tissue extending through the tissue resection window; a vacuum generation chamber disposed in the housing including a movable piston disposed in the vacuum generation chamber; a tissue trap disposed in or coupled to the housing, the tissue trap defining a sealed interior in fluid communication with the vacuum generation chamber via a one-way valve, so that air may be withdrawn from the tissue trap interior into the vacuum generation chamber by movement of the piston in a first direction, while air is prevented from entering the tissue trap interior from the vacuum generation chamber due to movement of the piston in a second direction opposite the first direction, wherein the open proximal end of the inner tubular member is disposed within the tissue trap interior; and an actuator moveably coupled to the housing and operatively connected to the piston, such that movement of the actuator relative to the housing causes movement of the piston within the vacuum generation chamber, wherein the actuator may be selectively operatively coupled to the inner tubular member, such that movement of the actuator relative to the housing also causes movement of the inner tubular member relative to the outer tubular member. A distal portion of the outer tubular member is preferably configured for insertion through a working channel of an endoscopic instrument for positioning the tissue resection window in an interior region of a patient's body.

The actuator may be coupled to the housing by a pinned connection, wherein rotation of the actuator about the pin moves the piston within the vacuum generation chamber, and selectively moves the inner tubular member relative to the outer tubular member. In one embodiment, the actuator is selectively operatively coupled to the inner tubular member by a slider having a first position relative to the housing in which the actuator is not operatively coupled to the inner tubular member, and a second position relative to the housing in which the actuator mechanically engages the inner tubular member to cause the open distal end of the inner tubular member to move distally across the tissue resection window as the actuator is moved relative to the housing.

Alternatively, the actuator may comprise an actuation member that slides axially relative to the housing, wherein sliding the actuator along the housing moves the piston within the vacuum generation chamber. For example, the vacuum generating actuation member may be a ring positioned around tubular portion of the housing. The same or a different mechanism may be used for selectively moving the inner tubular member relative to the outer tubular member.

The device may further comprise a seal disposed within the tissue trap interior and configured for engaging and sealing the open proximal end of the inner tubular member when the inner tubular member is in a proximally withdrawn position relative to the outer tubular member. A first spring may be provided that restores the actuator following movement of the actuator. A second spring may be provided to restore the inner tubular member to a proximally withdrawn position following movement of the inner tubular member caused by the actuator.

In another embodiment, a tissue removal device comprises a housing; an outer tubular member coupled to the housing and having a distal portion including a tissue resection window; an inner tubular member slidably disposed within the outer tubular member and defining an inner lumen extending from an open distal end to an open proximal end, the open distal end comprising a cutting edge to sever tissue extending through the tissue resection window; a vacuum generation chamber disposed in the housing including a movable piston disposed in the vacuum generation chamber; a tissue trap disposed in or coupled to the housing, the tissue trap defining a sealed interior in fluid communication with the vacuum generation chamber via a one-way valve, so that air may be withdrawn from the tissue trap interior into the vacuum generation chamber by movement of the piston in a first direction, while air is prevented from entering the tissue trap interior from the vacuum generation chamber due to movement of the piston in a second direction opposite the first direction, wherein the open proximal end of the inner tubular member is disposed within the tissue trap interior; an actuator moveably coupled to the housing by a pinned connection and operatively connected to the piston, such that rotation of the actuator about the pin moves the piston within the vacuum generation chamber, and wherein the actuator may be selectively operatively coupled to the inner tubular member, such that movement of the actuator relative to the housing also causes movement of the inner tubular member relative to the outer tubular member; and a spring configured to restore the actuator following manual rotation of the actuator relative to the housing.

The actuator may be selectively operatively coupled to the inner tubular member by a slider having a first position relative to the housing in which the actuator is not operatively coupled to the inner tubular member, and a second position relative to the housing in which the actuator mechanically engages the inner tubular member to cause the open distal end of the inner tubular member to move distally across the tissue resection window as the actuator is rotated relative to the housing. The device may include a further spring configured to restore the inner tubular member to a proximally withdrawn position following movement of the inner tubular member caused by the actuator. The device may further include a seal disposed within the tissue trap interior and configured for engaging and sealing the open proximal end of the inner tubular member when the inner tubular member is in a proximally withdrawn position relative to the outer tubular member. Preferably, a distal portion of the outer tubular member is configured for insertion through a working channel of an endoscopic instrument for positioning the tissue resection window in an interior region of a patient's body.

In accordance with yet another embodiment, a tissue removal device comprises a housing; an outer tubular member having a proximal portion connected to the housing, and a distal portion including a tissue resection window; an inner tubular member having a tissue cutting open distal end disposed within the outer tubular member; and a manually powered actuation assembly operatively coupled to the inner tubular member for moving the inner tubular member to move relative to the outer tubular member to thereby cause the open distal end of the inner tubular member to move distally across the tissue resection window for cutting tissue extending through the resection window, wherein the actuation assembly is configured such that manual activation of the assembly causes the inner tubular member to rotate and axially translate relative to the resection window.

By way of non-limiting example, the actuation assembly may be a trigger pivotally coupled to the housing, wherein pivoting the trigger relative to the housing causes the inner tubular member to move relative to the resection window. In one such embodiment, the trigger has a first end disposed within the housing, a second end disposed outside of the housing, the actuation assembly further comprising a drive gear mounted within the housing and operatively engaging a mating gear on the inner tubular member. The actuation assembly may be configured such that the resection window is closed by a distal end portion of the inner tubular member when the inner tubular member is stationary. In some embodiments, the device further comprises a tissue aspiration port formed by or coupled to the housing and in fluid communication with an open proximal end of the inner tubular member.

In still another embodiment, a tissue removal system is provided, including a tissue cutting device having an outer tubular member having a resection window and an inner tubular member disposed within the outer tubular member and movable across the resection window for cutting tissue extending therethrough. A motor is operatively coupled to the inner tubular member for moving the inner tubular member across the resection window, with a user-operable switch that activates and deactivates the motor. A vacuum source is fluidly coupled to an open proximal end of the inner tubular member for continuously applying suction thereto, wherein the tissue cutting device further comprises a mechanical arrangement for preventing suction from being applied through the resection window if the inner member is stationary.

Additional objects, as well as aspects, features and advantages, of the disclosure are set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the disclosed inventions. The following detailed description is, therefore, not to be taken in a limiting sense, and the scope of the disclosure is best defined by the appended claims.

BRIEF DESCRIPTION OF THE DRAWINGS

The above and other aspects and features of the disclosed embodiments will become more apparent upon consideration of the following detailed description, taken in conjunction with the accompanying drawings, in which like reference characters refer to like parts throughout, and in which:

FIG. 1 is a perspective view of a first embodiment of a tissue removal system constructed according to the teachings of the disclosure;

FIG. 6 is a fragmentary side view, partly in section, of a third alternate embodiment of a tissue cutting device for use in system of FIG. 1;

FIG. 21(b) is a rear view of the tissue cutting device shown in FIG. 21(a);

FIG. 21(c) is a section view of the tissue cutting device shown in FIG. 21(b) taken along line 1-1;

FIG. 21(d) is a fragmentary enlarged view of the circled area 2 of the tissue cutting device shown in FIG. 21(c);

FIGS. 22(a) through 22(d) are fragmentary perspective in a rest state, fragmentary exploded perspective, fragmentary longitudinal section in a rest state, and fragmentary longitudinal section in a rotating state views, respectively, of a first alternate embodiment of a tissue cutting device for use in the system of FIG. 20;

DETAILED DESCRIPTION

Figure 2A:
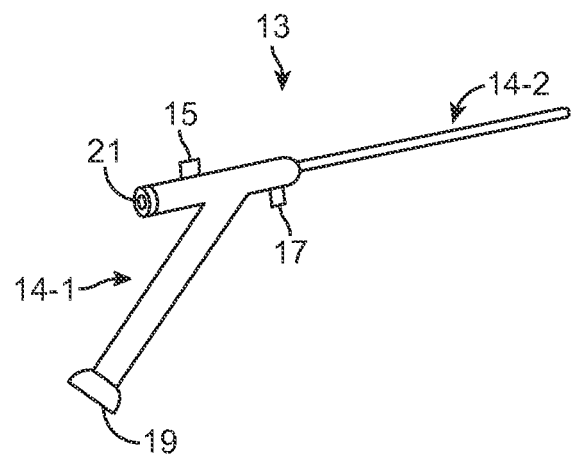
FIGS. 2(a) and 2(b) are enlarged perspective and enlarged transverse section views, respectively, of the access device shown in FIG. 1, the access device of FIG. 2(b) being shown with a tissue removal device inserted thereinto.

The disclosure is described below primarily in the context of devices and procedures optimized for performing one or more therapeutic or diagnostic gynecological or urological procedures such as the removal of uterine polyps or other abnormal uterine tissue. However, the devices and related procedures of the disclosure may be used in a wide variety of applications throughout the body, through a variety of access pathways.

For example, the devices of the disclosure can be optimized for use via open surgery, less invasive access such as laparoscopic access, or minimally invasive procedures such as via percutaneous access. In addition, the devices of the disclosure can be configured for access to a therapeutic or diagnostic site via any of the body's natural openings to accomplish access via the ears, nose, mouth, and via trans-rectal, urethral and vaginal approach.

In addition to the performance of one or more gynecological and urologic procedures described in detail herein, the systems, methods, apparatus and devices of the disclosure may be used to perform one or more additional procedures, including but not limited to access and tissue manipulation or removal from any of a variety of organs such as the bladder, breast, lung, stomach, bowel, esophagus, oral cavity, rectum, nasal sinus, Eustachian tubes, heart, gall bladder, arteries, veins, and various ducts. Routes of access include but are not limited to trans-cervical; trans-vaginal-wall; trans-uteral; trans-vesicle; trans-urethral; and other routes.

FIG. 1 is a perspective view of a first embodiment of a tissue removal system, the tissue removal system being constructed according to the teachings of the disclosure and being represented generally by reference numeral 11. System 11 is particularly well-suited for removing uterine polyps and other similar abnormal gynecological tissues. However, it should be understood that system 11 is not limited to such a use and may be used in other anatomies and for other purposes apparent to those of ordinary skill in the art.

System 11 comprises an access device 13. In the present embodiment, access device 13 may be a hysteroscope, wherein access to the patient's body is achieved through the cervix. However, access device 13 may alternatively be any of a wide variety of other instruments, such as endoscopes, catheters, cannulas, and the like, and access may be gained through other natural openings or orifices in the body, for example, ears, nose, mouth, via trans-rectal, urethral, vaginal, or though surgical incision, or the like.

Figure 2B:
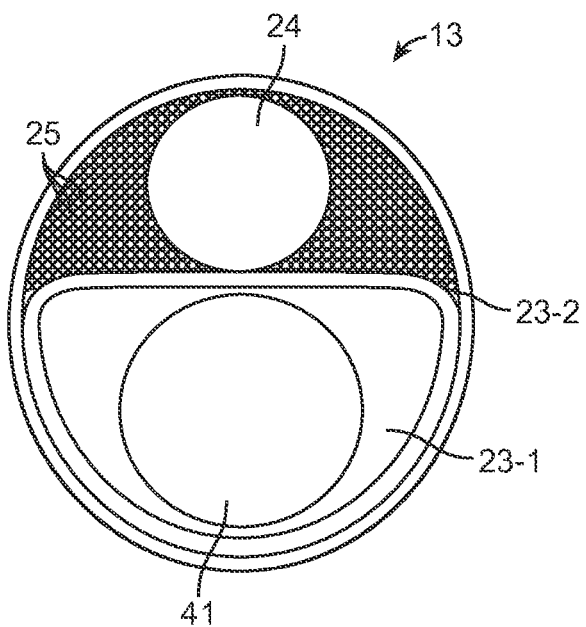
Figure 3A:
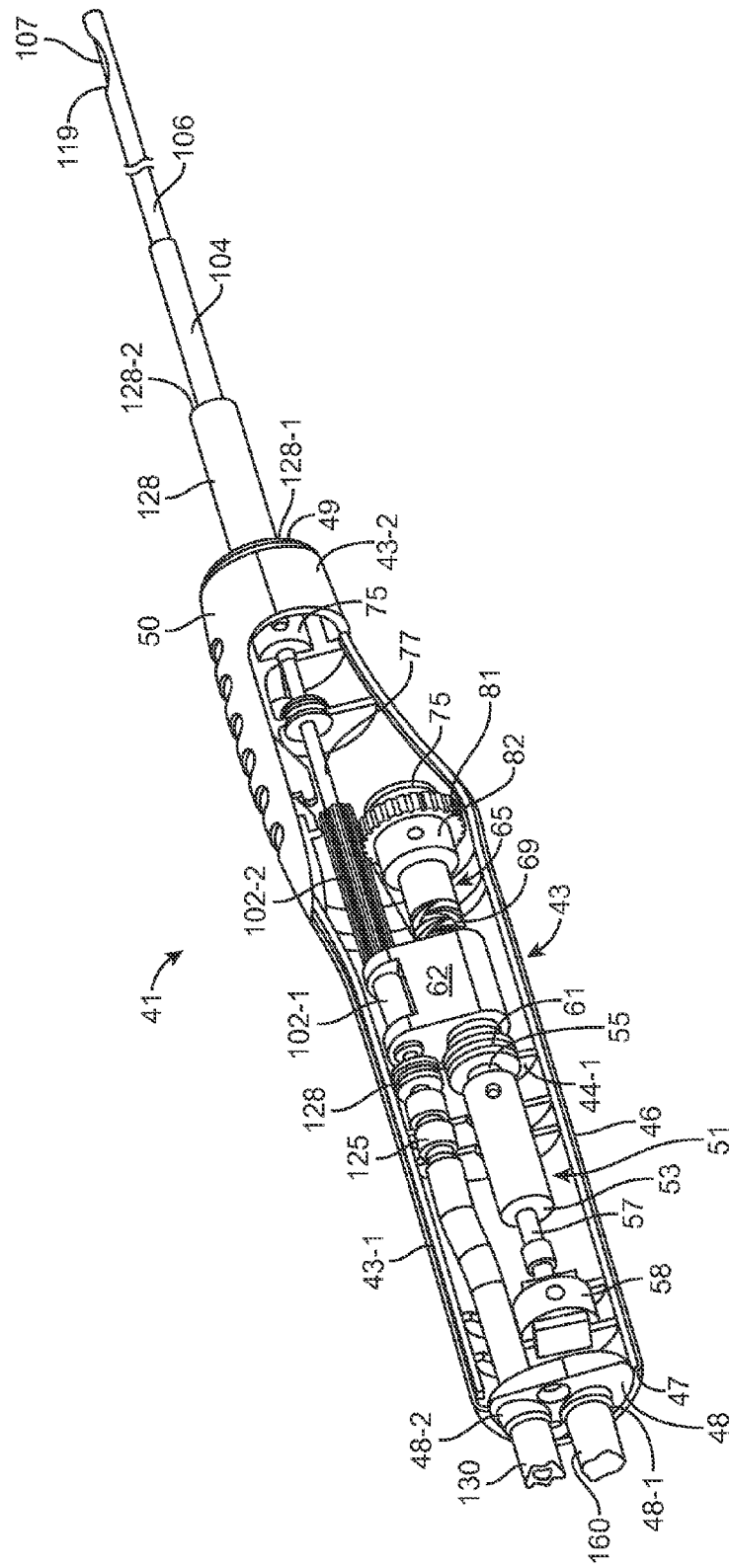
FIGS. 3(a) through 3(d) are various views of the tissue cutting device shown in FIG. 1, the tissue cutting device being shown in FIGS. 3(a) through 3(c), together with the distal ends of the vacuum tube and the sheath covering the external drive shaft.
Figure 3B:
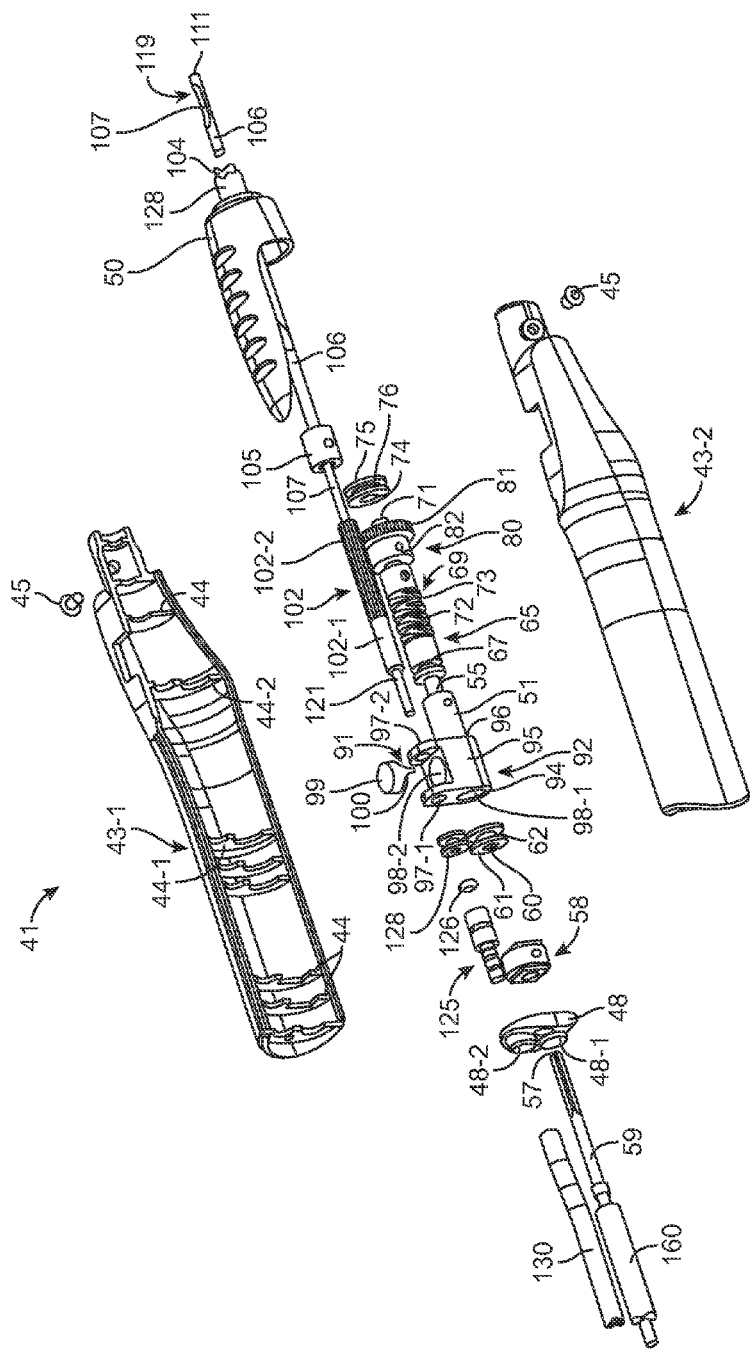
Figure 3C:
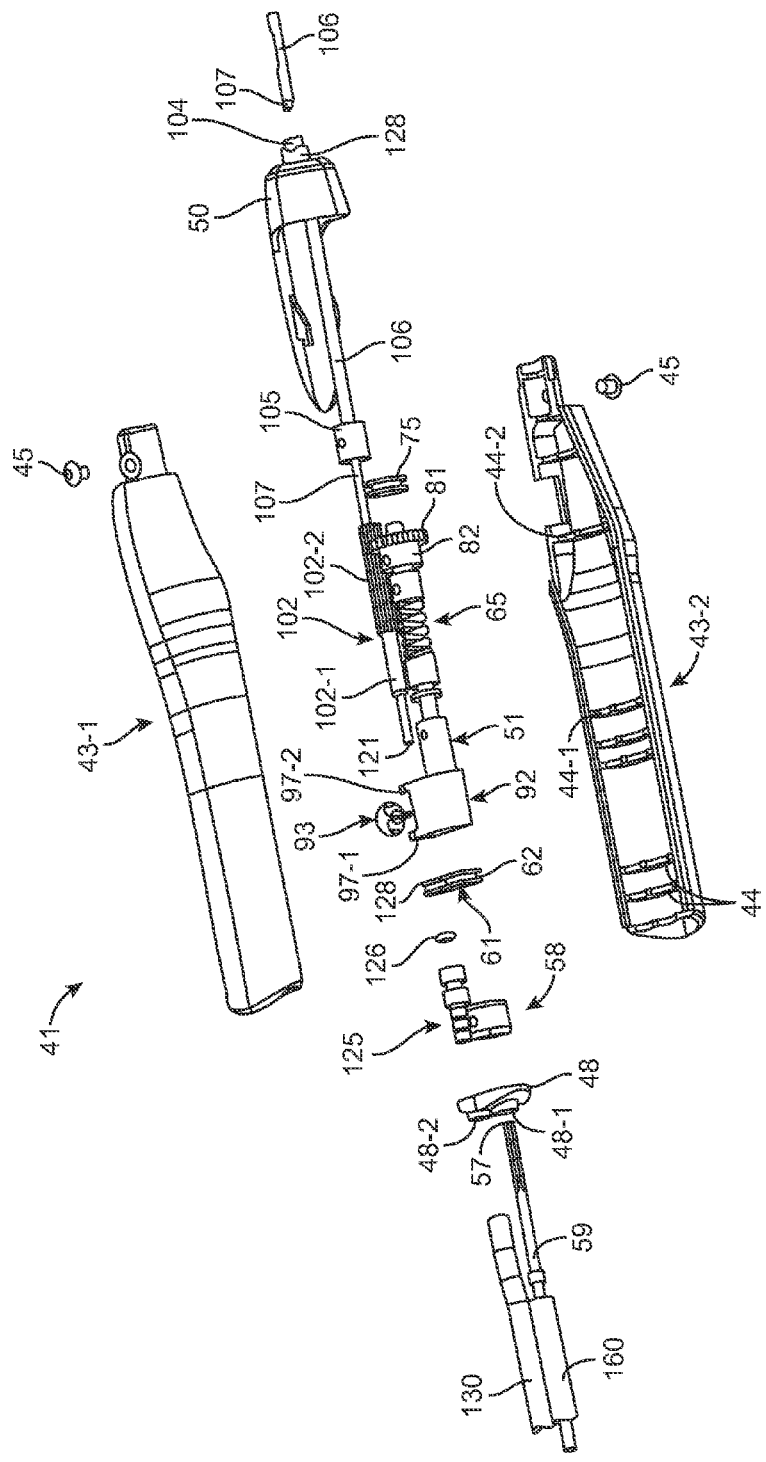
Figure 3D:
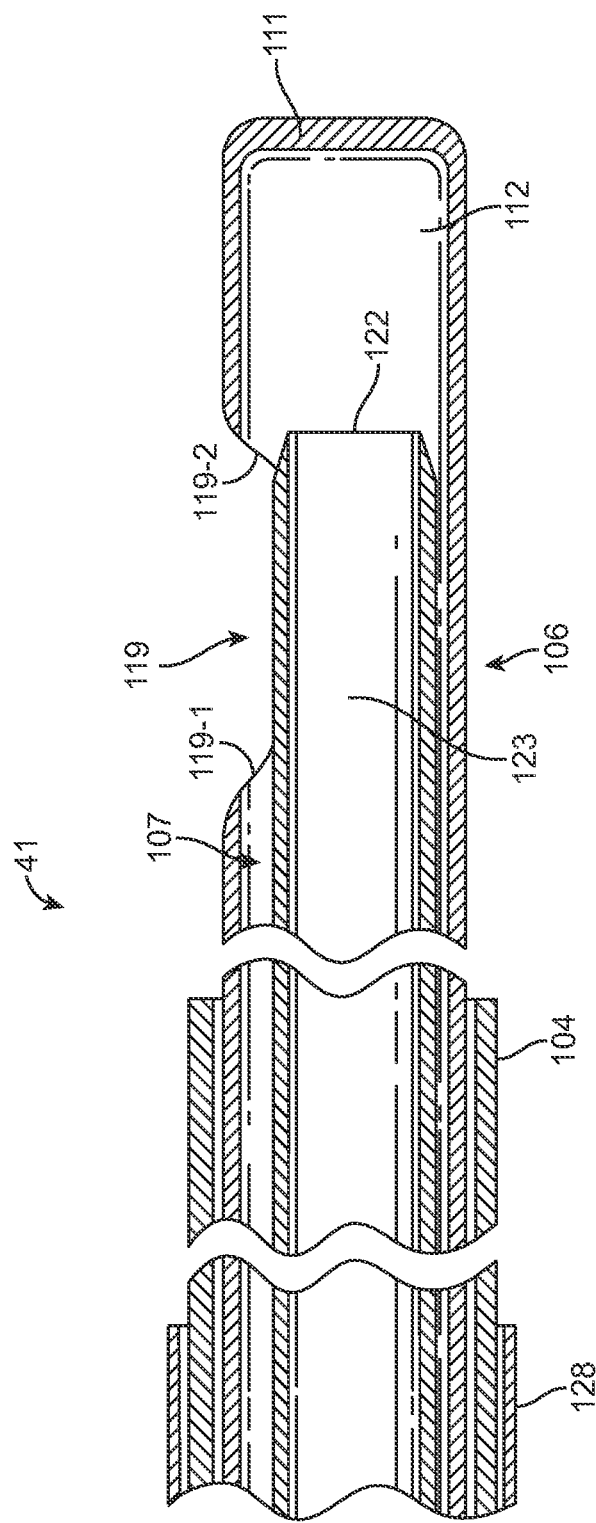

Access device 13, shown separately in FIGS. 2(a) and 2(b), may be conventional in construction for a hysteroscope and is shaped to comprise a handle 14-1, which is adapted to be held in the hand of a user, and a shaft 14-2, which extends distally from handle 14-1 and whose distal end is adapted to be removably inserted into a patient. Handle 14-1 is shaped to include a fluid input port 15, an illumination input port 17, an observation output port 19, and an instrument input opening 21. In addition, access device 13 comprises a plurality of channels extending distally from handle 14-1 and continuing longitudinally through shaft 14-2. The channels include a first channel 23-1 and a second channel 23-2. First channel 23-1 is in fluid communication with fluid input port 15 and, at the same time, is accessible through instrument input opening 21. In this manner, a medical instrument, such as a tissue removal device, may be inserted into opening 21 and through first channel 23-1, with the unoccupied remainder of first channel 23-1 being available to conduct distension fluid. A rod lens 24 or other suitable light collecting means is disposed in second channel 23-2, with the remainder of second channel 23-2 being occupied by fiber optics 25 or other suitable light transmitting means.

System 11 also comprises a fluid supply 16 for supplying input port 15 with distension fluid. Fluid supply 16 comprises a fluid-containing syringe, a peristaltic pump, or another suitable fluid-dispensing device coupled to input port 15 through tubing 16-1. Fluid supply 16 may comprise automated means (not shown) for dispensing inflow fluid therefrom at a desired rate. System 11 additionally comprises a means for supplying illuminating light to the distal end using optical fibers 25. The illumination supplying mechanism includes a light source 31 and an optical cable 33. Cable 33 comprises a first end optically coupled to light source 31 and an opposite end optically coupled to illumination input port 17 of access device 13.

System 11 includes a mechanism for converting light signals transmitted from rod lens 24 in access device 13 into corresponding electrical signals. The signal converting mechanism includes a camera 35 and an optical cable 37. Optical cable 37 has a first end optically coupled to observation output port 19 of access device 13 through an adapter 38 and a second end optically coupled to camera 35. System 11 also includes a monitor 39 electrically coupled to camera 35 via a cable 40, for converting the electrical signals generated by camera 35 into images. In this manner, monitor 39 may be used to display real-time images of the uterus or other body part into which access device 13 has been inserted. System 11 further includes a tissue cutting device 41.

Referring to FIGS. 3(*a*) through 3(*d*), the tissue cutting device 41 may be seen in greater detail. Device 41 has complementary left and right housing halves 43-1 and 43-2, respectively, each of which is made of a rigid polymer or other suitable material. Halves 43-1 and 43-2 are joined together with screws 45 to form an elongated hollow housing 43 comprising a rounded side wall 46, an open proximal end 47, and an open distal end 49. Housing 43 may be bent or otherwise ergonomically shaped to fit comfortably in the hand of a user. A proximal cap 48 is mounted in proximal end 47, cap 48 being shaped to include a pair of lumens 48-1 and 48-2. Lumen 48-1 may be used to receive, for example, an external drive shaft, and lumen 48-2 may be used to receive, for example, a vacuum tube. A distal cap 50 is mounted in distal end 49, cap 50 being shaped to include a lumen, which receives a pair of coaxial cutting tubes.

A plurality of ribs 44 are integrally formed and appropriately positioned along the respective interior surfaces of halves 43-1 and 43-2, ribs 44 providing structural reinforcement to housing 43 and being used to align certain of the mechanical components that are positioned within housing 43.

An internal drive shaft 51 is provided and adapted for rotation about its longitudinal axis. Shaft 51, which may be an elongated unitary structure made of a suitably rigid metal or polymer, is shaped to include a proximal end 53 and a distal end 55. Proximal end 53 of shaft 51 is coaxially mounted over and fixed to the distal end 57 of an external drive shaft 59, external drive shaft 59 being inserted through a retainer 58 mounted in housing 43. In this manner, the rotation of shaft 51 is mechanically coupled to the rotation of shaft 59. Distal end 55 of shaft 51 is inserted through an opening 60 in an annular bushing 61, which bushing 61 is matingly mounted on a rib 44-1 via a circumferential slot 62 provided in bushing 61.

Device 41 further comprises a translation drive shaft 65 adapted for rotation about its longitudinal axis. Shaft 65, which may be an elongated unitary structure made of a suitably rigid metal or polymer, is shaped to include a proximal end 67, an intermediate portion 69, and a distal end 71. Proximal end 67 of shaft 65 is coaxially mounted over and fixed to the distal end 55 of internal drive shaft 51. In this manner, the rotation of shaft 65 is mechanically coupled to the rotation of shaft 51. Intermediate portion 69 is shaped to include a double helical portion comprising a right-handed threaded helical channel 72 and a left-handed threaded helical channel 73. Helical channels 72 and 73 may have identical or different pitches. Helical channels 72 and 73 are smoothly blended together at their respective ends to form a continuous groove so that there is a smooth transition from one helical channel to the other. Distal end 71 of shaft 65 is appropriately dimensioned to be received within an opening 74 in an annular bushing 75, which bushing 75 is matingly mounted on a rib 44-2 via a circumferential slot 76 provided in bushing 75. It should be noted that, although shaft 65 is adapted for rotation, shaft 65 is translationally stationary.

Device 41 further comprises a gear assembly 80 adapted for rotation about its longitudinal axis. Gear assembly 80, which may be an elongated unitary structure made of a suitably rigid metal or polymer, is shaped to include a proximal spur gear 81 and a distal tube portion 82. Gear assembly 80 is coaxially mounted over intermediate portion 69 of shaft 65 in an area between the double helical portion and distal end 71, and gear assembly 80 is fixed to shaft 65 using a pin inserted radially through tube portion 82 and into an opening provided in shaft 65. In this manner, the rotation of spur gear 81 is mechanically coupled to the rotation of shaft 65.

Device 41 further comprises an oscillating translation assembly 91. Translation assembly 91, in turn, includes a carriage 92 and a channel engagement member 93. Carriage 92, which may be a unitary structure made of a suitably rigid metal or polymer, is shaped to include a proximal portion 94, an intermediate portion 95, and a distal portion 96. The tops of proximal portion 94 and distal portion 96 extend beyond the top of intermediate portion 95 and are shaped to include loops 97-1 and 97-2, respectively, loops 97-1 and 97-2 being aligned with one another. A longitudinal bore 98-1 is provided near the bottom of carriage 92, bore 98-1 being appropriately dimensioned to coaxially receive intermediate portion 69 of shaft 65 while permitting intermediate portion 69 to rotate freely therewithin. Channel engagement member 93, which may be a unitary structure made of a suitably rigid metal or polymer, is shaped to include a base 99 and a pawl 100. Base 99 is disposed in an opening 98-2 that extends downwardly from the top of intermediate portion 95 into communication with bore 98-1, with pawl 100 traveling within the double helical portion of shaft 65. In this manner, as shaft 65 rotates, pawl 100 continuously travels back and forth through the double helical portion of shaft 65, thereby causing carriage 92 to oscillate translationally.

As can be appreciated, the speed at which carriage 92 oscillates translationally may be varied, for example, by varying the translational length of the double helical portion of shaft 65, the angles of channels 72 and 73, the rotational speed of shaft 59, etc. As will be discussed further below, it may be desirable to operate device 41 so that carriage 92 oscillates translationally at about 2.8 cycles per second.

Device 41 further comprises a shaft 102 adapted for rotation about its longitudinal axis. Shaft 102, which may be an elongated, unitary, tubular structure made of a suitably rigid metal or polymer, is shaped to include a proximal portion 102-1 and a distal portion 102-2. Proximal portion 102-1 is inserted through loops 97-1 and 97-2 of carriage 92 and freely rotates relative to loops 97-1 and 97-2. Distal portion 102-2 is in the form of an elongated spur gear. Distal portion 102-2 is engaged with spur gear 81 of gear assembly 80 so that the rotation of spur gear 81 causes the rotation of shaft 102. Distal portion 102-2 is elongated so that it maintains engagement with spur gear 81 even as distal portion 102-2 moves translationally relative to spur gear 81.

The speed at which distal portion 102-2 rotates (and, therefore, the speed at which shaft 102 rotates) may be the same as or different than the speed at which spur gear 81 rotates, depending, for example, on the relative diameters of the two gears (the ratio of the rotational speeds of the two gears being inversely proportional to the ratio of the diameters of the two gears). Consequently, by appropriately dimensioning spur gear 81 and distal portion 102-2, one can achieve a desired rotational speed, even where the rotational speed of the external drive shaft is fixed. For example, in the embodiment shown, distal portion 102-2 has a diameter that is one-fourth the diameter of spur gear 81 and, therefore, rotates four times as fast as gear 81. Therefore, if the external drive shaft has a speed of rotation of about 1500 rpm, gear 81 would rotate at 1500 rpm and distal portion 102-2 would rotate at 6000 rpm. As can be appreciated, the rotational speed of distal portion 102-2 does not depend on the interaction of translation assembly 91 with the double helical portion of shaft 65; consequently, distal portion 102-2 may attain higher or lower rotational speeds than would be possible based on the requirements of a desired translational speed. Notwithstanding the above, shaft 102 is translationally coupled to carriage 92. Consequently, as carriage 92 oscillates translationally, so does shaft 102.

Device 41 further comprises a strain relief member 104, which may be a unitary tubular structure made of a rigid polymer or metal. The proximal end of strain relief member 104 is fixedly mounted in a retainer 105, which is mounted at the distal end of housing 43, with the distal end of strain relief member 104 extending distally from housing 43 for a short distance, such as, for example, approximately 2 inches.

Device 41 further comprises a cutting mechanism, which includes an outer tubular member 106 and an inner tubular member 107. Inner tubular member 107 moves rotationally and simultaneously oscillates translationally relative to outer tubular member 106 in a manner further described below. Outer tubular member 106, which may be a unitary structure made of a suitable plastic, is shaped to include an open proximal end, a closed distal end 111, and a lumen 112 extending from the open proximal end to a point just prior to closed distal end 111. Member 106 is coaxially mounted within strain relief member 104, with the proximal end of member 106 disposed within the proximal end of strain relief member 104 and with distal end 111 of member 106 extending distally beyond the distal end of strain relief member 104 for an extended distance, such as, for example, five inches. The proximal end of member 106 is fixed within retainer 105.

Outer tubular member 106 includes a resection window 119 into which tissue may be captured and drawn, window 119 being located proximate to distal end 111, such as, for example, 0.25 inch from distal end 111. Window 119 is shaped to include a proximal end 119-1 and a distal end 119-2. Proximal end 119-1 slopes gradually upwardly proximally, and distal end 119-2 slopes gradually upwardly distally. More specifically, window 119 may have a length of approximately 0.55 inch, proximal end 119-1 may be a radial end having a radius of curvature of, for example, 0.085 inch, and distal end 119-2 may be a radial end having a radius of curvature of, for example, 0.150 inch. Window 119 may extend over a substantial portion of the circumference of tubular member 106, such as, for example, about 60% of the circumference.

Outer tubular member 106 may have an outer diameter less than about 5.5 mm. However, in order to reduce the risk of injury to the patient and in order to obviate the need for anesthesia to be administered to the patient, outer tubular member 106 preferably has an outer diameter less than about 5 mm, more preferably less than 4 mm, even more preferably less than 3 mm, and still even more preferably less than 2 mm. However, should device 41 be used in an operating room setting where general anesthesia is available, the diameter of the outer tubular member 106 could be increased to maximize tissue removal. In such a case, outer tubular member 106 could have a diameter generally less than about 12 mm, preferably less than about 11 mm, and, for certain applications, less than 10 mm. Depending on the particular clinical application, outer tubular member 106 could be constructed having an outer diameter of no more than about 9 mm, in some applications less than about 8 mm, preferably less than 7 mm, and more preferably less than 6 mm where OD is desirably minimized.

Inner tubular member 107, which may be an elongated one-piece structure made of 300-series stainless steel, includes a proximal end 121, a distal end 122, and a longitudinal lumen 123. Distal end 122 may be shaped, for example, by grinding, to include an external bevel, such as, for example, an external bevel of approximately 20 degrees. An intermediate length of inner tubular member 107 is coaxially received within shaft 102 and is fixedly coupled to shaft 102 for translational and rotational movement therewith. Proximal end 121 of inner tubular member 107 is slidably mounted within a vacuum tube connector 125, which in turn is coupled to a vacuum tube 130 inserted through lumen 48-2 of cap 48. An O-ring 126 is mounted within connector 125 to maintain a good seal with inner tubular member 107. An annular bushing 128 mounted within housing 43 receives inner tubular member 107 and maintains its alignment.

Tubular members 106 and 107 are arranged so that, when inner tubular member 107 is in a fully retracted (i.e., proximal) position, distal end 122 of inner tubular member 107 is withdrawn sufficiently to permit tissue to enter window 119 (preferably with distal end 122 of inner tubular member 107 positioned proximal to window 119), and so that, when inner tubular member 107 is in a fully advanced (i.e., distal) position, distal end 122 of tubular member 107 is positioned distally of distal end 119-2 of window 119. In this manner, as inner tubular member 107 is moved translationally and rotationally past window 119, tissue within window 119 may be sheared. To promote such a shearing of tissue, the outer diameter of inner tubular member 107 may be just slightly less (e.g., about 0.002 inch) than the inner diameter of outer tubular member 106.

Device 41 further comprises an indicator sleeve 128. Sleeve 128, which may be an elongated tubular member made of a material that is easily distinguishable visually from strain relief member 104, is coaxially mounted over strain relief member 104 and fixedly mounted thereto, with a proximal end 128-1 of sleeve 128 lying flush against the distal end of housing 43. An example of a material suitable for use as sleeve 128 may be a white or colored length of shrink-wrap material. Sleeve 128 may be dimensioned so that, when device 41 is inserted into access device 13, distal end 128-2 of sleeve 128 is visible to a user until distal end 111 of device 41 is advanced beyond the distal end of access device 13. In other words, distal end 128-2 may be used to indicate when distal end 111 of device 41 lies flush with the distal end of access device 13. In this manner, a user may safely control the position of the distal end of device 41 and, therefore, keep it within access device 13 when inserting device 41 into a patient, thereby reducing the risks for lacerations and perforations during introduction of device 41.

System 11 further comprises a specimen container 141 and a vacuum source 143. The proximal end of vacuum tube 130 is connected to a first port 145 of container 141. The distal end of a tube 147 is connected to a second port 149 of container 141, and the proximal end of tube 147 is connected to vacuum source 143. In this manner, vacuum source 143 is used to apply suction to device 41, and any withdrawn tissue, liquids or similar matter suctioned through device 41 may be collected in container 141.

System 11 further comprises a motor unit 151, which may include a motor (not shown) and electronics (not shown). A pneumatic foot switch 153 is fluidly coupled to a tube 155 which, in turn, is fluidly coupled to a pneumatic switch 157 on motor unit 151. Foot switch 153 is used as a power switch to selectively activate or de-activate the motor within unit 151. The proximal end of shaft 59 is mechanically coupled for rotation to the motor located within unit 151, and the distal end of shaft 59 is inserted through opening 48-1 and coupled to internal shaft 51 in the manner discussed above. A protective sheath 160 covers much of the length of shaft 59. Unit 151 further includes a vacuum sensor 161 coupled to container 141 by a tube 163 so that the pressure within container 141 may be monitored. In this manner, a sudden increase in vacuum pressure may indicate that a clog has occurred. The presence of a clog may be indicated by an alarm (not shown) located on unit 151. The detection of a clog is often a clear indication that the further operation of device 41 may only aggravate the clogging situation and that a cessation of tissue removal may be necessary.

Unit 151 is configured to synchronize actuation of its motor with actuation of vacuum source 143. This may be done using a cable 165 electrically connecting unit 151 and vacuum source 143. In this manner, turning on the motor will turn on vacuum source 143 at the same time. Correspondingly, vacuum source 143 is deactivated whenever the motor is not turned on. Such an arrangement may ameliorate the above-discussed problem of distension fluid being suctioned from the uterus through device 41 even when device 41 is not actuated for cutting.

In use, the distal end of shaft 14-2 of access device 13 may be inserted transcervically, i.e., through the vagina and the cervix, into the uterus of the patient. If desired, prior to insertion of shaft 14-2 into the patient, the cervix may be gradually dilated in the conventional manner using obturators of increasing diameter. The uterus may be washed of blood or other debris that may be present by dispensing fluid from fluid supply 16 first through port 15 and then through first channel 23-1 of device 13. Fluid and debris present in the uterus may exit the uterus proximally through a removable outflow channel (not shown) inserted into channel 23-1 of device 13 and connected at its proximal end to container 141. When the washing procedure is complete, fluid may continue to be dispensed into the uterus in order to fluidly distend the uterus to a desired extent. With the uterus thus distended, access device 13 may then be used to examine the interior of the uterus.

If polyps or like abnormalities are detected that one wishes to remove, tissue removal device 41 may be loaded into access device 13, i.e., by inserting the distal ends of outer tubular member 106 and inner tubular member 107 distally through channel 23-1 of access device 13. Tissue cutting device 41 may then be manipulated so that window 119 of outer tubular member 106 may be positioned in proximity to the polyp or other targeted tissue. Next, foot switch 153 may be depressed, causing the motor within unit 151 to be actuated and also causing vacuum source 143 to be actuated. The actuation of vacuum source 143 causes suction to be applied to inner tubular member 107, thereby drawing tissue into outer tubular member 106 through window 119. The actuation of the motor within unit 151 causes inner tubular member 107 simultaneously to rotate and to oscillate back and forth translationally within outer tubular member 106, thereby resulting in the cutting of the tissue that is drawn through window 119.

The cut tissue may then be suctioned from the patient through inner tubular member 107 by means of the aforementioned suction and, thereafter, collected in container 141. Once the polyps or other targeted tissues have been removed from the patient, foot switch 153 may be released, causing vacuum source 143 and the motor within unit 151 to be turned off. Tissue cutting device 41 and access device 13 may then be removed from the patient. Tissue cutting device 41 may be designed to be a single use device. If so, device 41 may then be disconnected from tube 130 and shaft 59 and disposed of properly.

It will be appreciated that, although the above discussion contemplates using access device 13 to introduce tissue cutting device 41 into the uterus, one may insert tissue cutting device 41 transcervically into the uterus without the use of access device 13. In such a situation, fluid may be administered transcervically to the uterus by a fluid dispensing device in order to distend the uterus, and, thereafter, observation of the uterus may be accomplished, for example, by ultrasonic imaging using an ultrasonic probe inserted transcervically into the uterus. Such an ultrasonic probe may be separate from device 41 or may be integrated into device 41. Alternatively, imaging of the uterus may be performed by MRI imaging.

Although one may vary one or more of the speed of rotational movement of inner tubular member 107, the frequency of oscillating translational movement of inner tubular member 107, the advance ratio of inner tubular member 107 (i.e., the ratio of the speed at which inner tubular member 107 oscillates translationally to the speed at which inner tubular member 107 rotates), and the magnitude of suction provided by vacuum source 143, the following conditions are preferred: speed of rotation of inner tubular member 107—at least 1100 rpm, more preferably at least 5000 rpm, even more preferably approximately 6000 rpm; frequency of oscillating translational movement of inner tubular member 107—at least 1.5 cycles per second, more preferably about 2.5 to 4 cycles per second, even more preferably about 2.8 cycles per second; advance ratio of preferably less than 0.25, more preferably less than 0.15; and vacuum pressures in the range of 200 to 650 mmHg. The above parameters may be selected to achieve a rate of tissue removal of at least 1.5 gm/min while outer tubular member 106 has an outer diameter of no greater than about 3.0 mm.

As can also be appreciated, as suction is applied to inner tubular member 107, some of the distension fluid located in the uterus may incidentally be withdrawn from the uterus through inner tubular member 107. This loss of distension fluid from the uterus may be undesirable if it interferes with maintenance of the uterus in an adequately distended state. System 11 may be constructed and operated so that, with a vacuum in excess of 300 mmHg, a volume of no more than about 300 cc/min of fluid is removed. This may be achieved, as in the present embodiment, by applying suction only when the motor for moving inner tubular member 107 is actuated. Alternatively, this may be achieved by having some arrangement for closing window 119 with inner tubular member 107 each time the motor control is stopped. Examples of such arrangements are discussed later in this application.

Figure 4:
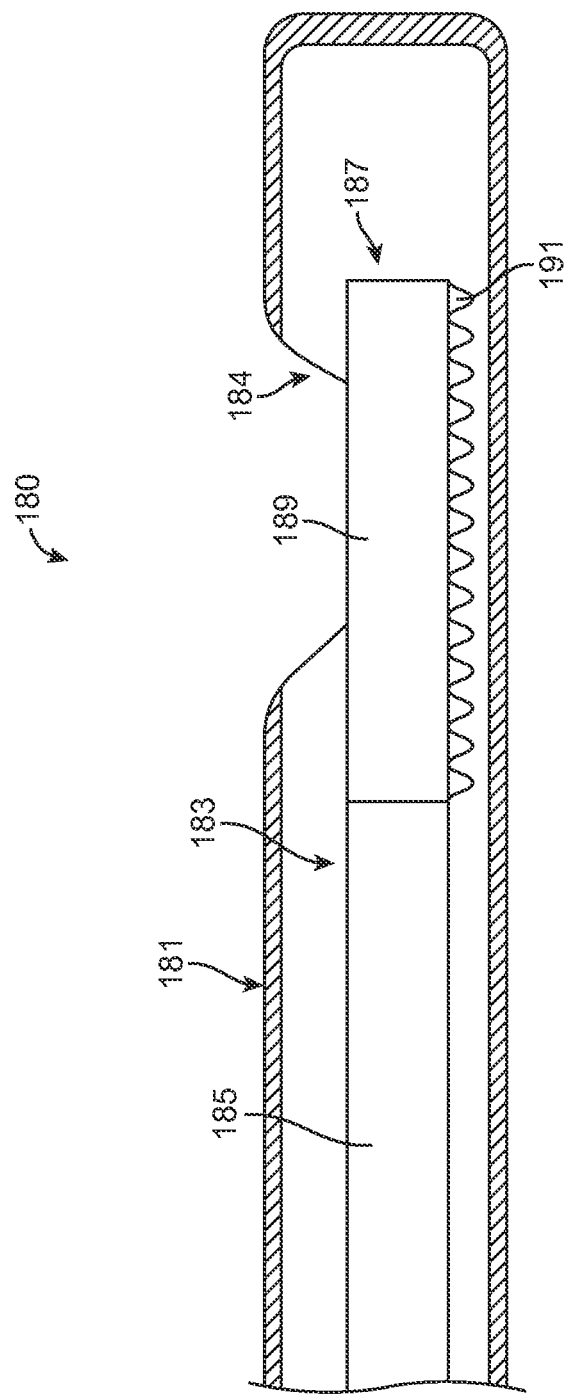
FIG. 4 is a fragmentary side view, partly in section, of a first alternate embodiment of a tissue cutting device for use in the system of FIG. 1.

FIG. 4 is a fragmentary side view, partly in section, of a first alternate embodiment of a tissue cutting device for use in system 11, the first alternate embodiment being represented generally by reference numeral 180. Device 180 is similar in many respects to device 41, one difference between the two devices being that, whereas device 41 comprises an outer tubular member 106 and an inner tubular member 107, device 180 comprises an outer tubular member 181 and a cutter 183. Outer tubular member 181 is similar in most respects to outer tubular member 106, the principal difference between the two tubular members being that, whereas outer tubular member 106 may be made of molded plastic, outer tubular member 181 may be made of stainless steel or another similarly suitable material.

Outer tubular member 181 includes a window 184, similar in size and shape to window 119, through which a polyp or similar tissue may be drawn. Cutter 183 comprises a proximal portion 185 and a distal portion 187, proximal portion 185 and distal portion 187 being securely joined to one another in an end-to-end fashion, for example, using a suitable adhesive. Proximal portion 185 comprises a tube, which may be made of extruded plastic, and may correspond in length to a majority of the length of inner tubular member 107. Distal portion 187, which may be made, for example, by injection molding, comprises a tubular portion 189 and a serrated edge 191. In use, a polyp or similar tissue may be drawn, by suction, into the interior of outer tubular member 181 through window 184. The tissue may then be cut by serrated edge 191 as cutter 183 moves across the interior of window 184. The severed tissue may then be removed, by suction, through the hollow interior of cutter 183.

Figure 5A:
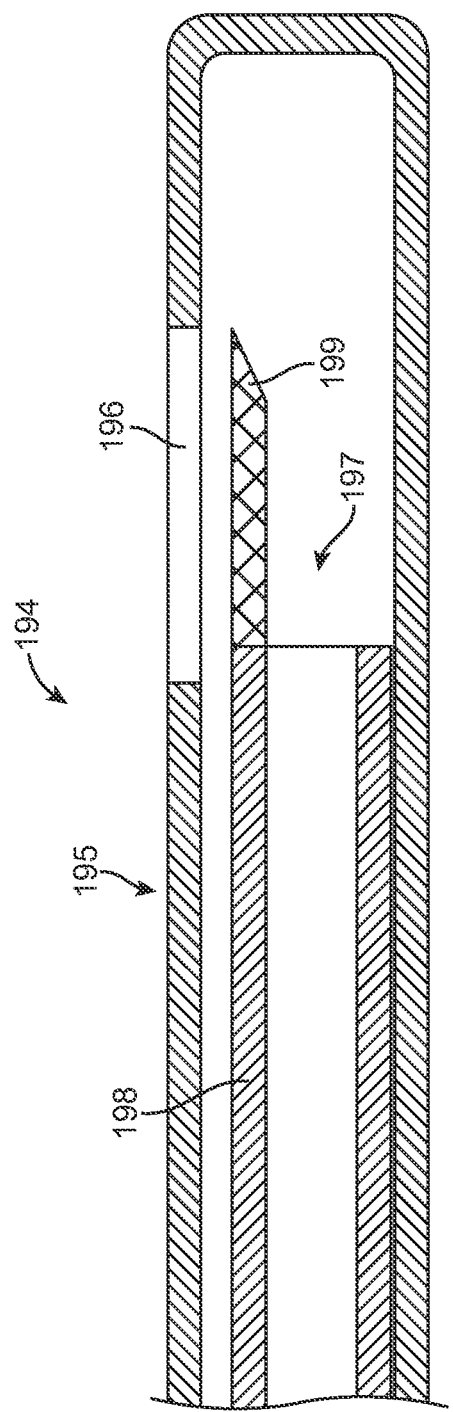
FIGS. 5(a) and 5(b) are fragmentary longitudinal and transverse section views, respectively, of a second alternate embodiment of a tissue cutting device for use in the system of FIG. 1.
Figure 5B:
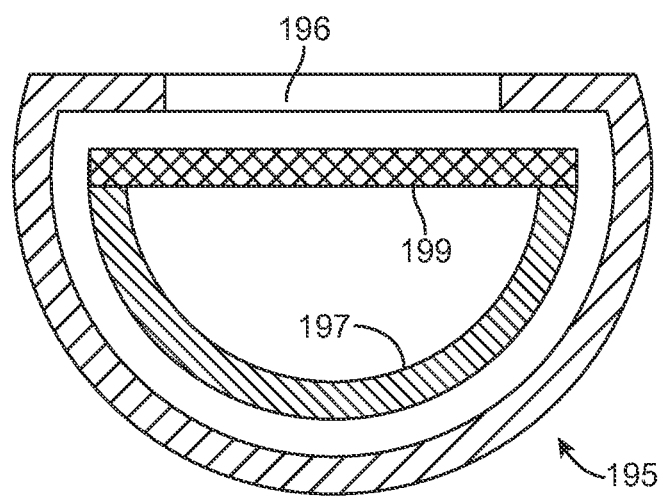

FIGS. 5(*a*) and 5(*b*) depict fragmentary longitudinal and transverse section views of a second alternate embodiment of a tissue cutting device for use in system 11, the second alternate embodiment being represented generally by reference numeral 194. Device 194 is similar in most respects to device 41. One difference between the two devices is that, whereas device 41 comprises outer tubular member 106 and inner tubular member 107, device 194 includes an outer tubular member 195 and a cutter 197. Outer tubular member 195 is similar to outer tubular member 106 (or to outer tubular member 181 of device 180), except that outer tubular member 195 is D-shaped in transverse cross-section. Outer tubular member 195 includes a window 196, through which a polyp or similar tissue may be drawn. Cutter 197 comprises a proximal portion 198 and a distal portion 199, proximal portion 198 and distal portion 199 being securely joined to one another in an end-to-end fashion by suitable means. Proximal portion 198 comprises a tube and may correspond in length to a majority of the length of inner tubular member 107. Distal portion 199 comprises a razor blade. In use, a polyp or similar tissue may be drawn, by suction, into the interior of outer tubular member 195 through window 196.

The tissue may then be cut by distal portion 199 as distal portion 199 moves across the interior of window 196. The severed tissue may then be removed, by suction, through the hollow interior of proximal portion 198. As can be appreciated, since rotational movement of cutter 197 is not desired, structure corresponding to distal portion 102-2 and spur gear 81 of device 41 may be omitted from device 194.

FIG. 6 is a fragmentary side view, partly in section, of a third alternate embodiment of a tissue cutting device for use in system 11, the third alternate embodiment being represented generally by reference numeral 200. Device 200 is similar in many respects to device 41, one difference between the two devices being that, whereas device 41 comprises outer tubular member 106 and inner tubular member 107, device 200 comprises an outer tubular member 201 and a cutter 203. Outer tubular member 201 is similar, for example, to outer tubular member 106 (or to outer tubular member 181 of device 180). Cutter 203 is in the form of an auger. In use, tubular member 201 may be positioned so that a polyp or similar tissue extends into the interior of tubular member 201 through window 205. The tissue may then be cut and moved proximally through the interior of tubular member 201 by the rotational movement of 203.

As can be appreciated, device 200 may obviate the need for the use of suction in system 11. Therefore, when using device 200, components relating to a vacuum source in system 11 may be omitted. In addition, since oscillating translational movement of cutter 203 may not be desired, those components of tissue removal device 41 used to provide oscillating translational movement may be omitted from device 200.

Figure 7:
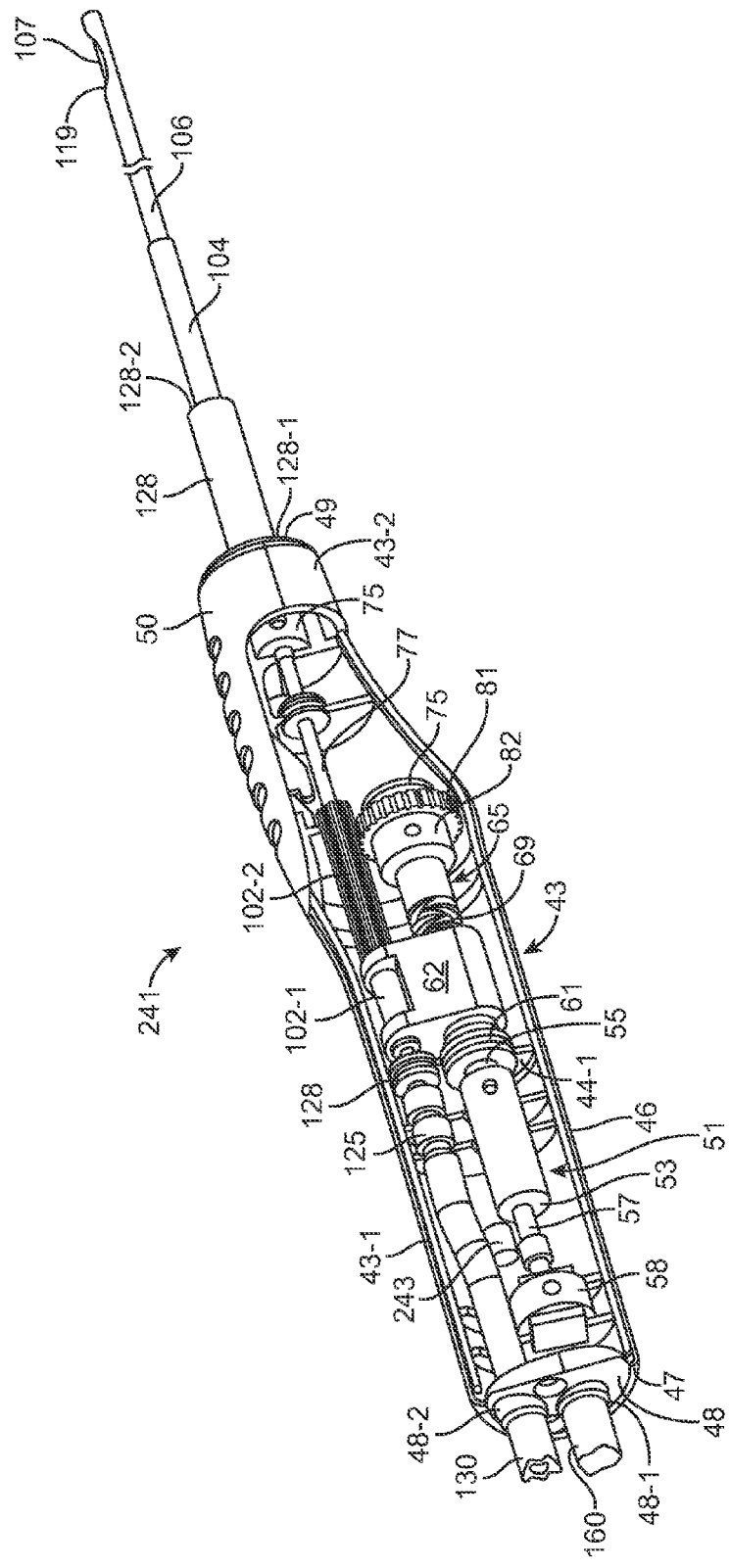
FIG. 7 is a fragmentary perspective view, broken away in part, of a fourth alternate embodiment of a tissue cutting device for use in the system of FIG. 1.

FIG. 7 is a fourth alternate embodiment of a tissue cutting device for use in system 11, the fourth alternate embodiment being represented generally by reference numeral 241. Device 241 is similar to device 41, the principal difference between the two devices being that device 241 additionally includes a tissue trap 243 disposed within housing 43. Tissue trap 243 is appropriately coupled to tube 130 to collect tissue from those materials suctioned through tube 130.

Figure 8A:
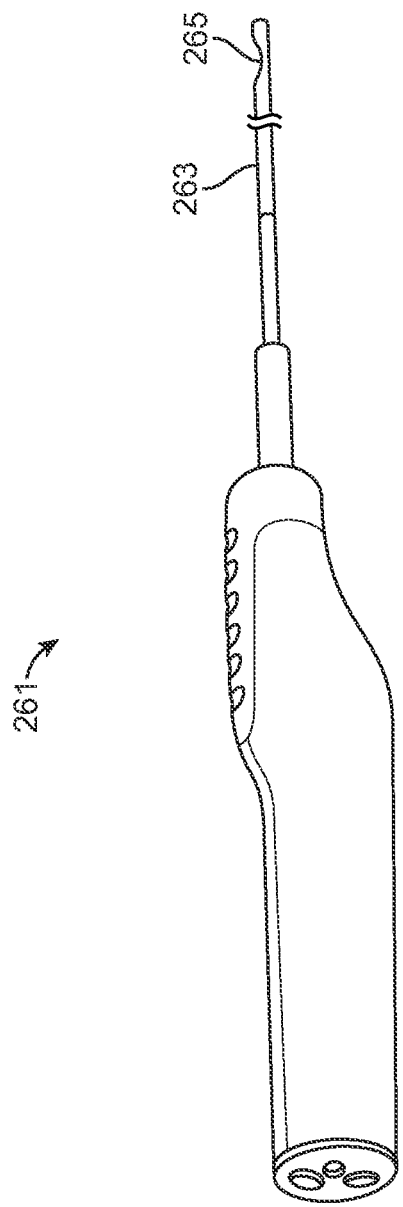
FIGS. 8(a) and 8(b) are perspective and enlarged, fragmentary, top views, respectively, of a fifth alternate embodiment of a tissue cutting device for use in the system of FIG. 1.
Figure 8B:
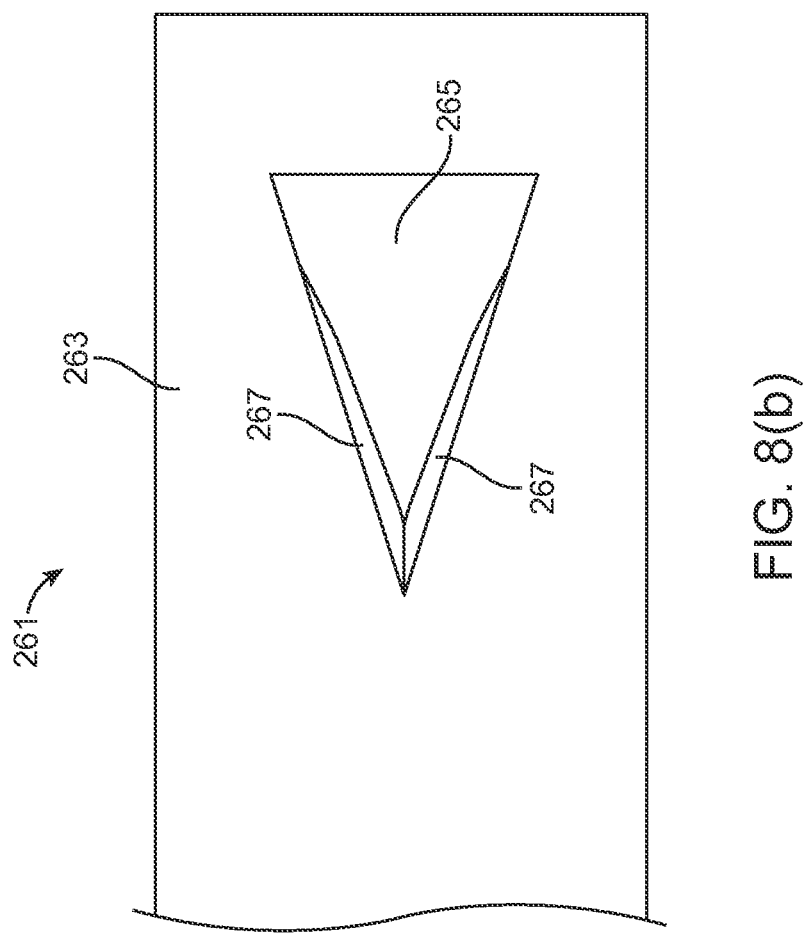

FIGS. 8(*a*) and 8(*b*) illustrate yet another alternate embodiment of a tissue removal device for use in system 11, the fifth alternate embodiment being represented generally by reference numeral 261. Device 261 is similar in many respects to device 41, the principal difference between the two devices being that, whereas device 41 comprises, amongst other things, outer tubular member 106, inner tubular member 107, and a mechanism for rotating and for translationally moving inner tubular member 107 relative to outer tubular member 106, device 261 does not include structure corresponding to inner tubular member 107 (nor does it include a corresponding mechanism for rotating and for translationally moving such an inner tubular member). Instead, device 261 comprises a tubular member 263. Tubular member 263, in turn, comprises an opening 265 having one or more cutting edges 267. In use, a polyp or similar tissue may be drawn, by suction, into tubular member 263 through window 265. The tissue may then be cut along one or more of edges 267 by manually moving device 261 and tubular member 263 in the direction opposite to the direction of suction.

Figure 9A:
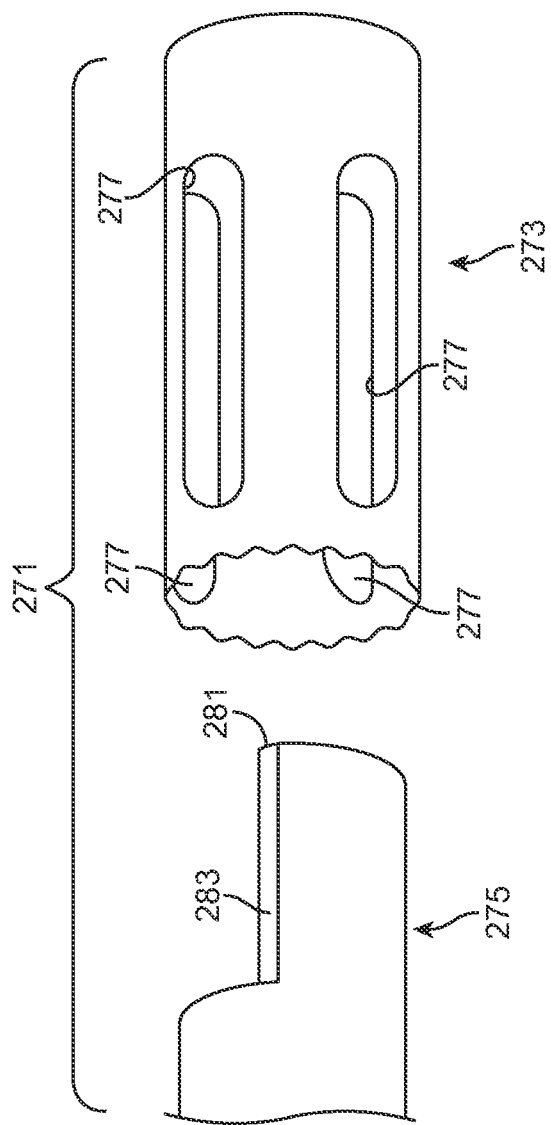
FIGS. 9(a) through 9(c) are fragmentary exploded perspective, fragmentary longitudinal section, and transverse section views, respectively, of a sixth alternate embodiment of a tissue cutting device for use in the system of FIG. 1.
Figure 9B:
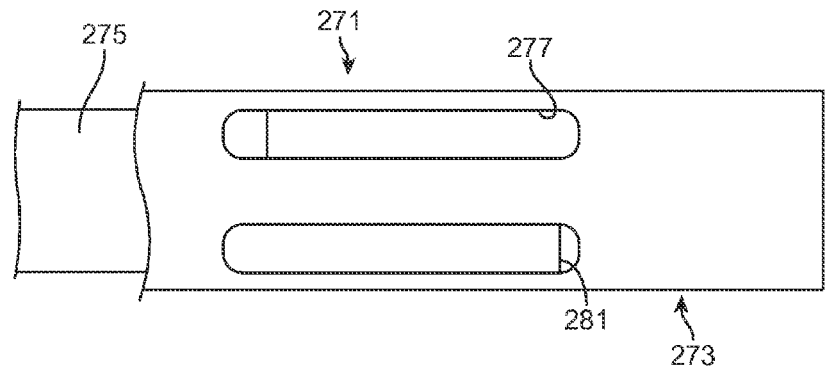
Figure 9C:
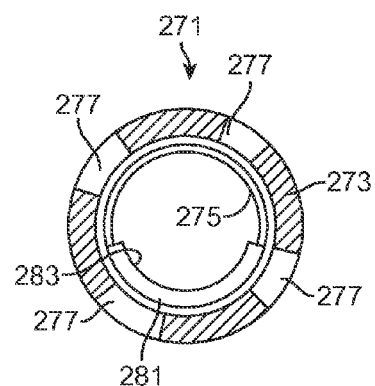

FIGS. 9(*a*) through 9(*c*) illustrate a still further embodiment of a tissue cutting device for use in system 11, the tissue cutting device being represented generally by reference numeral 271. Device 271 is similar in most respects to device 41, the principal difference between the two devices being that, whereas device 41 comprises an outer tubular member 106 and an inner tubular member 107, device 271 comprises an outer tubular member 273 and an inner tubular member 275.

Outer tubular member 273 is similar in many respects to outer tubular member 106 (or to outer tubular member 181 of device 180), the principal difference between the two outer tubular members being that, whereas outer tubular member 106 comprises a single window 119, outer tubular member 273 is shaped to include four transverse windows 277 evenly spaced around its circumference. Inner tubular member 275 is similar in many respects to inner tubular member 107, the principal difference between the two inner tubular members being that, whereas inner tubular member 107 comprises a beveled distal end 122, inner tubular member 275 comprises a distal end 281 shaped to include a blade 283. In use, with device 271 inserted into a patient and with suction applied, a polyp or other tissue may be drawn into the interior of outer tubular member 273 through one or more of windows 277. As inner tubular member 275 rotates within outer tubular member 273, the tissue that has been drawn into outer tubular member 273 is severed by blade 283.

Figure 10:
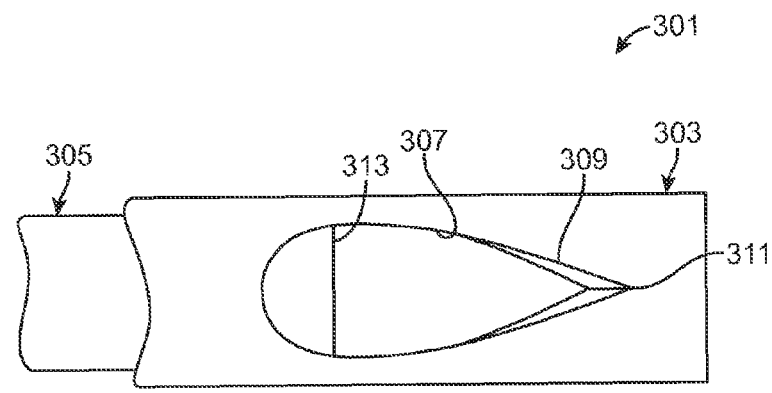
FIG. 10 is a fragmentary top view of a seventh alternate embodiment of a tissue cutting device for use in the system of FIG. 1.

FIG. 10 is a fragmentary top view of a seventh alternate embodiment of a tissue cutting device for use in system 11, represented generally by reference numeral 301. Device 301 is similar in most respects to device 41. One difference between the two devices is that, whereas device 41 comprises outer tubular member 106 and inner tubular member 107, device 301 comprises an outer tubular member 303 and an inner tubular member 305. Outer tubular member 303 is similar in most respects to outer tubular member 106 (or to outer tubular member 181 of device 180), the principal difference between the respective outer tubular members being that, whereas outer tubular member 106 comprises a window 119, outer tubular member 303 comprises a window 307. Window 307 has a generally tear-drop profile, with window 307 having a cutting edge 309 at its narrow distal end 311. Inner tubular member 305 is similar in most respects to inner tubular member 107, the principal difference between the two inner tubular members being that, whereas inner tubular member 107 comprises a sharpened distal end 122, inner tubular member 305 comprises a blunt distal end 313.

In use, inner tubular member 305 oscillates translationally relative to outer tubular member 303, and a polyp or similar tissue may be drawn, by suction, into the interior of outer tubular member 303 through window 307 when inner tubular member 305 is moved sufficiently proximally relative to window 307. The tissue may then be cut as inner tubular member 305 moves distally and pushes the drawn tissue against cutting edge 309 of outer tubular member 303. The severed tissue may then be removed, by suction, through the hollow interior of inner tubular member 305. As can be appreciated, since rotational movement of inner tubular member 305 may not be desired, structure corresponding to distal portion 102-2 and spur gear 81 of device 41 may be omitted from device 301.

Figure 11:
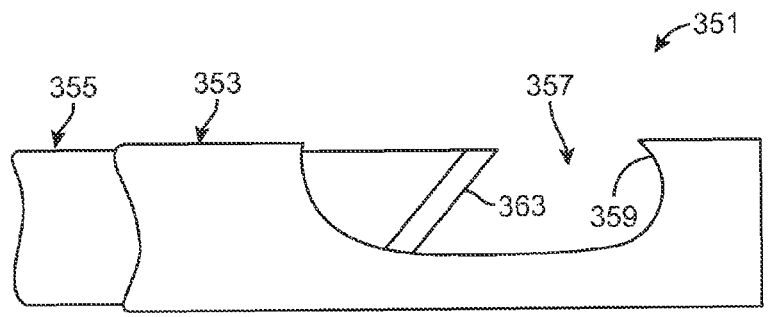
FIG. 11 is a fragmentary side view of an eighth alternate embodiment of a tissue cutting device for use in the system of FIG. 1.

FIG. 11 is a fragmentary side view of an eighth alternate embodiment of a tissue cutting device for use in system 11, the eighth alternate embodiment being represented generally by reference numeral 351. Device 351 is similar in most respects to device 41. One difference between the two devices is that, whereas device 41 comprises outer tubular member 106 and inner tubular member 107, device 351 comprises an outer tubular member 353 and an inner tubular member 355. Outer tubular member 353 is similar in most respects to outer tubular member 106 (or to outer tubular member 181 of device 180), the principal difference between the respective outer tubular members being that, whereas outer tubular member 106 comprises a window 119, outer tubular member 353 comprises a window 357. Window 357 differs from window 119 in that window 357 has a distal end 359 that bends back proximally and is well-suited for capturing tissue. Inner tubular member 355 is similar in most respects to inner tubular member 107, the principal difference between the two inner tubular members being that, whereas inner tubular member 107 comprises a sharpened distal end 122, inner tubular member 355 comprises a sharpened distal end 363.

In use, inner tubular member 355 oscillates translationally relative to outer tubular member 353, and a polyp or similar tissue may be drawn, by suction, into the interior of outer tubular member 353 through window 357 when inner tubular member 355 is moved sufficiently proximally relative to window 357. The tissue may then be cut as inner tubular member 355 moves distally and the drawn tissue is trapped between distal end 363 of inner tubular member 355 and distal end 359 of window 357. The severed tissue may then be removed, by suction, through the hollow interior of inner tubular member 355. As can be appreciated, since rotational movement of inner tubular member 355 may not be desired, structure corresponding to distal portion 102-2 and spur gear 81 of device 41 may be omitted from device 351.

Figure 12:
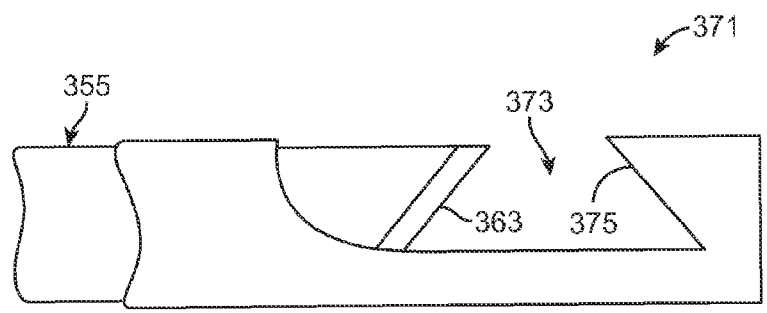
FIG. 12 is a fragmentary side view of a ninth alternate embodiment of a tissue cutting device for use in the system of FIG. 1.

FIG. 12 is a fragmentary side view of a ninth alternate embodiment of a tissue cutting device for use in system 11, the ninth alternate embodiment being represented generally by reference numeral 371. Device 371 is similar in most respects to device 351, the principal difference between the two devices being that, whereas device 351 comprises a window 357 having a distal end 359, device 371 comprises a window 373 having a distal end 375. Device 371 may be used in the same manner as device 351.

Figure 13:
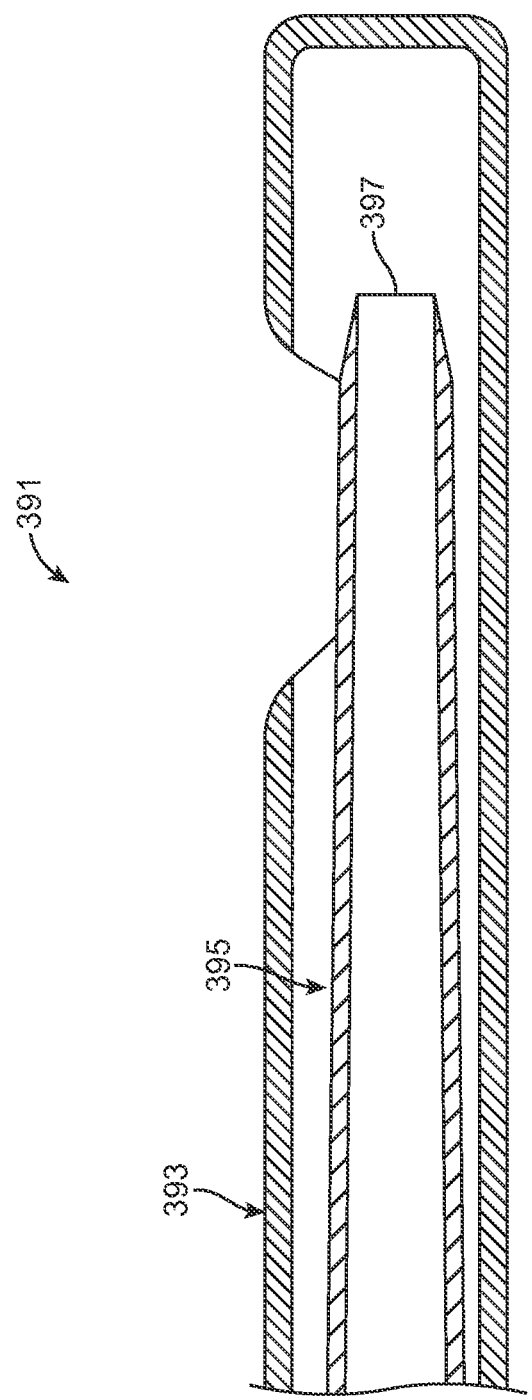
FIG. 13 is a fragmentary longitudinal section view of a tenth alternate embodiment of a tissue cutting device for use in the system of FIG. 1.
Figure 14:
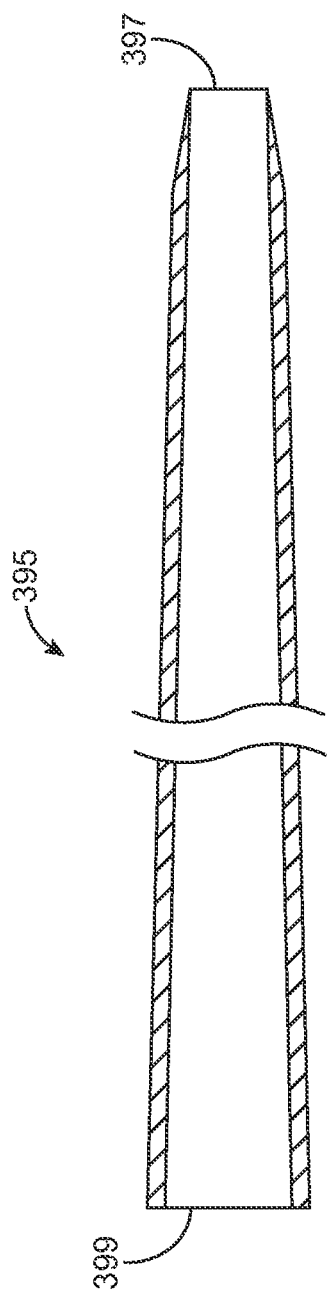
FIG. 14 is a fragmentary longitudinal section view of the inner tubular member shown in FIG. 13.

FIG. 13 is a fragmentary side view of a tenth alternate embodiment of a tissue cutting device for use in system 11, the tenth alternate embodiment being represented generally by reference numeral 391. Device 391 is similar in most respects to device 41. One difference between the two devices is that, whereas device 41 comprises an outer tubular member 106 and an inner tubular member 107, device 391 comprises an outer tubular member 393 and an inner tubular member 395 (inner tubular member 395 shown separately in FIG. 14, but not to-scale). Outer tubular member 393 is similar in most respects to outer tubular member 106, the principal difference between the two outer tubular members being that, whereas outer tubular member 106 may be made of plastic, outer tubular member 393 may be made of plastic, stainless steel, or another suitable material. Inner tubular member 395 is similar in most respects to inner tubular member 107, the principal difference between the two inner tubular members being that, whereas inner tubular member 107 may be made of 300-series stainless steel and may have a uniform inner diameter over its entire length (or, alternatively, may have a distal portion having a uniform first diameter and a proximal portion having a uniform second diameter, the second diameter being slightly greater than the first diameter), inner tubular member 395 may be made of a molded plastic, such as an injection molded liquid crystal polymer, and is conically shaped to taper from a more narrow distal end 397 to a wider proximal end 399. The broadening of inner tubular member 395, particularly the widening of its inner diameter, moving from distal end 397 to proximal end 399 may reduce the risk that inner tubular member 395 may become clogged with solid matter. The taper may be on the order of approximately 0.1 inch in diameter over a length of approximately 12 inches.

Figure 15:
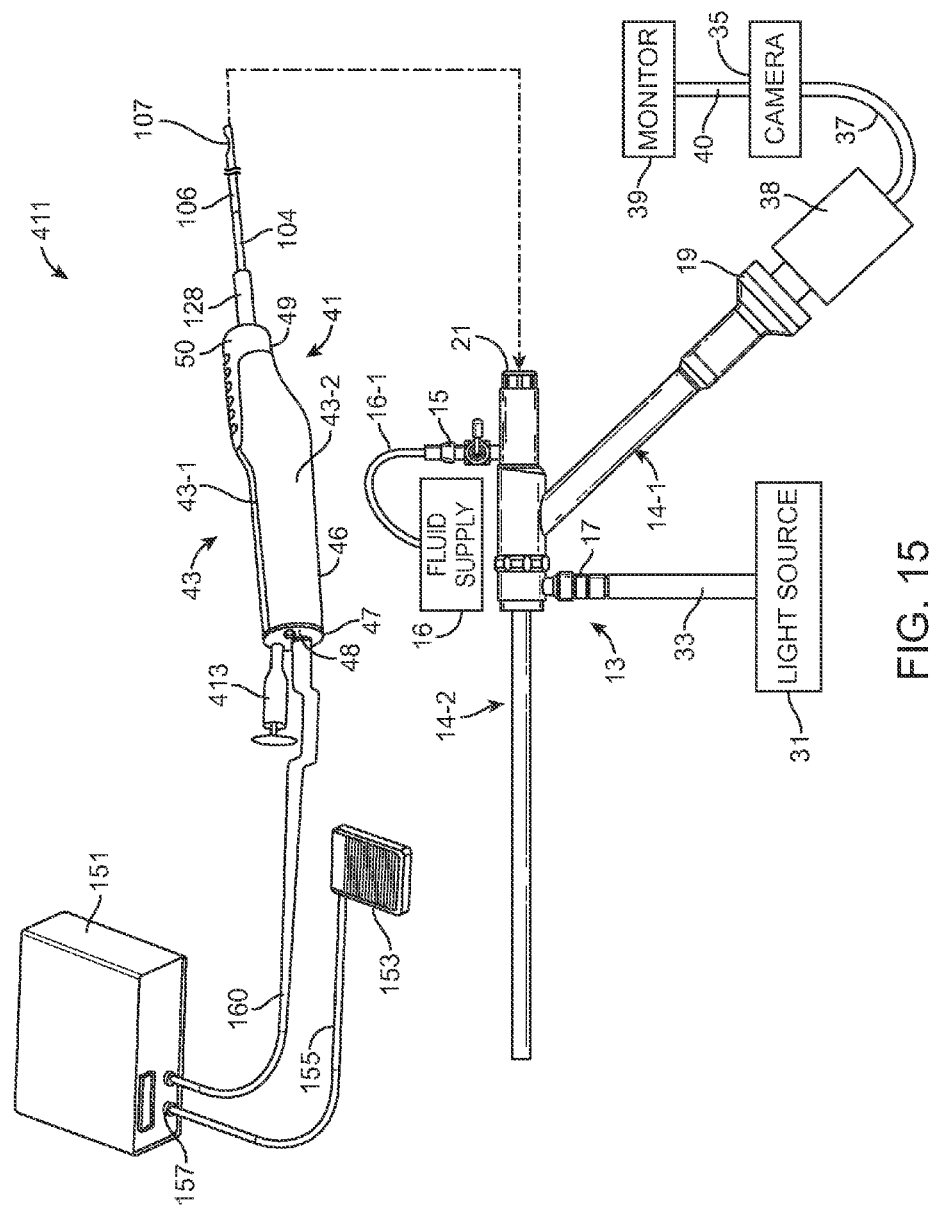
FIG. 15 is a perspective view of a second embodiment of a tissue removal system constructed according to the teachings of the disclosure.

FIG. 15 depicts a second embodiment of a tissue removal system constructed according to the teachings of the disclosure, the tissue removal system being represented generally by reference numeral 411. System 411 is similar in many respects to system 11, the principal difference between the two systems being that, whereas system 11 comprises specimen container 141 and vacuum source 143, system 411 comprises a syringe 413. System 411 may be used in much the same manner as system 11, except that, when one wishes to apply suction, one uses syringe 413. In this manner, one may control when suction is being applied so as to limit the amount of distending fluid that is suctioned when device 41 is not being used to cut tissue.

Figure 16:
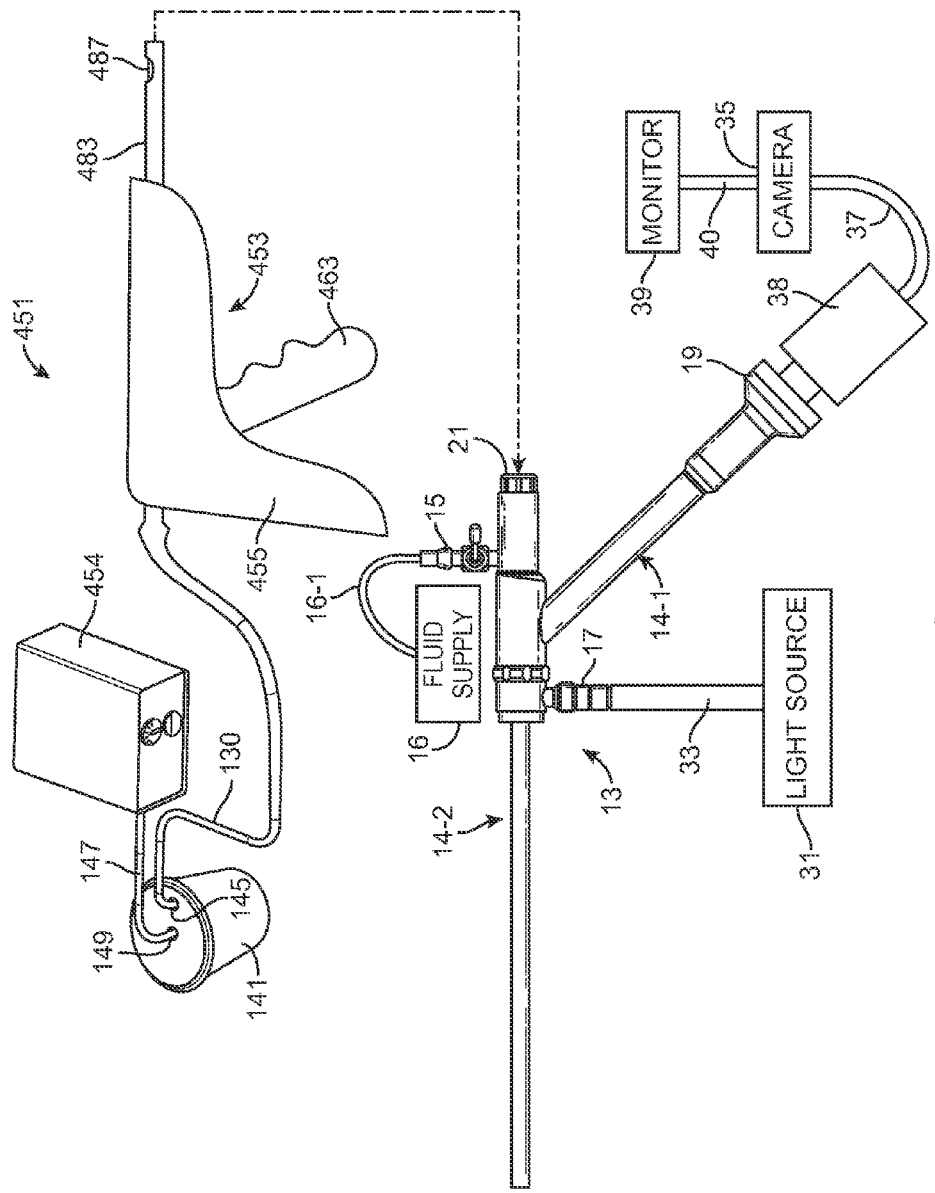
FIG. 16 is a perspective view of a third embodiment of a tissue removal system constructed according to the teachings of the disclosure.

FIG. 16 depicts a third embodiment of a tissue removal system constructed according to the teachings of the disclosure, the tissue removal system being represented generally by reference numeral 451. System 451 is similar in many respects to system 11. One difference between the two systems is that, whereas system 11 comprises device 41 and a motorized mechanism for powering device 41 (which motorized mechanism includes unit 151 and foot switch 153), system 451 comprises a hand-powered device 453. Another difference between system 451 and system 11 is that, whereas actuation of vacuum source 143 is coupled to actuation of unit 151, system 451 comprises a vacuum source 454 that is continuously being operated. A "continuously operated vacuum source" is a vacuum source that is applying suction for a period of time that encompasses and exceeds the period of time during which cutting occurs. Consequently, as will be seen below, device 453 may be designed so that suction from source 454 is applied to a patient only when device 453 is actively being used to cut tissue.

Figure 17:
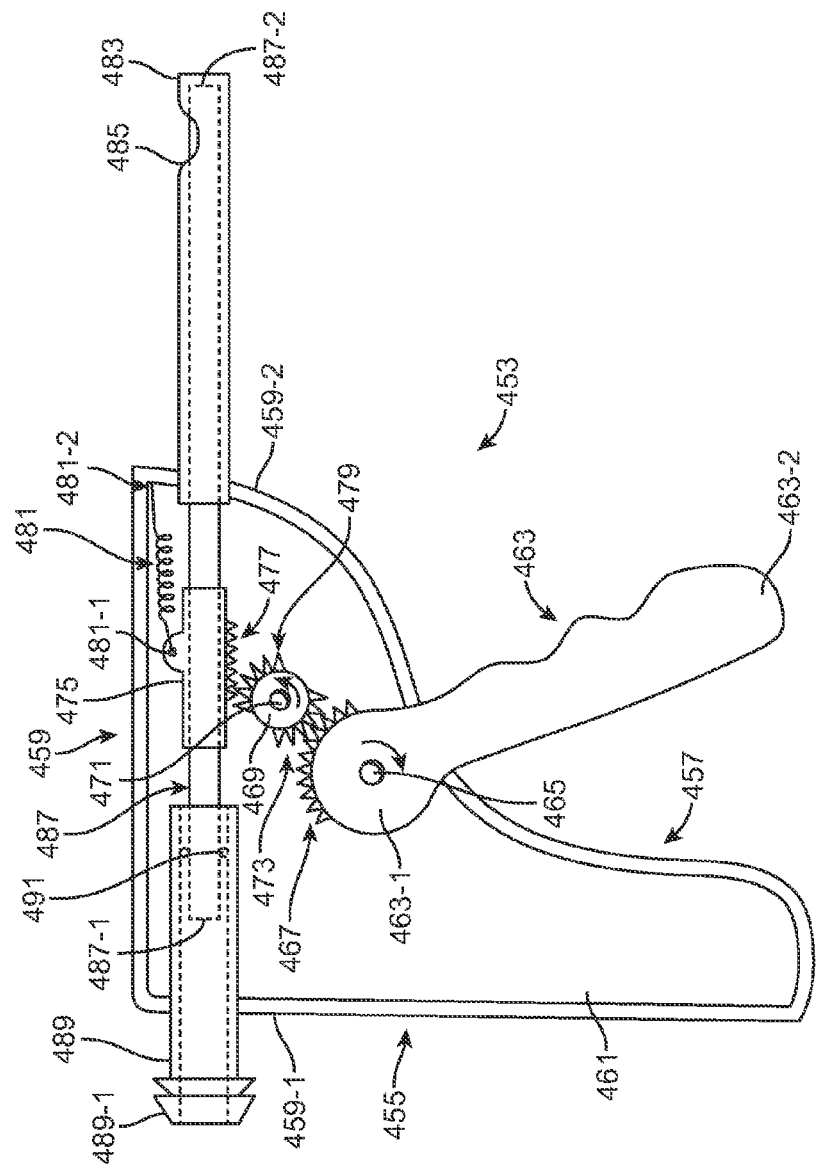
FIG. 17 is an enlarged side view of the tissue cutting device shown in FIG. 16.

Device 453 is shown in greater detail in FIG. 17, and includes a gun-shaped housing 455 shaped to include a handle portion 457 and a barrel portion 459. Housing 455 is formed from a pair of matching housing halves 461, the right housing half not being shown in FIG. 17 to reveal the interior of housing 455. Device 453 also comprises a trigger 463, which is pivotally mounted to housing 455 about a pivot pin 465. Trigger 463 is shaped to include a first end 463-1 positioned inside of housing 455 and a second end 463-2 positioned outside of housing 455. First end 463-1 is rounded in profile and shaped to include a set of gear teeth 467 positioned along a portion of its circumference.

Device 453 further comprises a reversing gear 469 pivotally mounted to housing 455 about a pivot pin 471. Gear 471 includes a first set of teeth 473 engageable with teeth 467 on trigger 463.

Device 453 further comprises a carriage 475 slidably mounted within housing 455. Carriage 475 is shaped to include a set of teeth 477 engageable with a second set of teeth 479 provided on gear 469. In this manner, the squeezing of trigger 463 causes carriage 475 to be moved back a short distance in the direction of the proximal end 459-1 of barrel portion 459. A spring 481 having a first end 481-1 fixed to carriage 475 and a second end 481-2 fixed to the distal end 459-2 of barrel portion 459 is used to bias carriage 475 in the direction of distal end 459-2.

Device 453 further comprises an outer tubular member 483 fixedly mounted to housing 455 and extending distally from distal end 459-2 of barrel portion 459. Outer tubular member 483 is similar to outer tubular member 106 or to outer tubular member 181 and includes a window 485 through which a polyp or similar tissue may pass to the interior of member 483.

Device 453 further comprises an inner tubular member 487. Inner tubular member 487 is shaped to include a proximal end 487-1 and a distal end 487-2. Proximal end 487-1 is disposed within a vacuum connector 489 fixedly mounted at proximal end 459-1 of barrel portion 459. Connector 489 has a barbed proximal end 489-1 adapted for insertion into the distal end of vacuum tube 130. An O-ring 491 is inserted around proximal end 487-1 to provide a vacuum seal around inner tubular member 487. Distal end 487-2 of inner tubular member 487 is disposed within outer tubular member 483. An intermediate portion of inner tubular member 487 is inserted through and fixedly coupled to carriage 475. In this manner, as carriage 475 moves back and forth in barrel portion 459, inner tubular member 487 moves back and forth correspondingly. It should be noted that, unlike, for example, inner tubular member 107, inner tubular member 487 does not rotate, but rather, only moves translationally in the manner discussed above.

In use, vacuum connector 489 may be connected to vacuum source 454, and outer tubular member 483 may be inserted into the patient (either via access device 13 or otherwise) and positioned so that window 485 is aligned with a polyp or similar tissue. Next, trigger 463 may be squeezed towards handle portion 457. As trigger 463 is initially drawn towards handle portion 457, the squeezing of trigger 463 causes gear 469 to rotate due to the engagement of teeth 467 with teeth 473. This, in turn, causes carriage 475 to be moved backwards a short distance towards proximal end 459-1 as a result of the engagement of teeth 477 with teeth 479. This movement of carriage 475, in turn, causes inner tubular member 487 to be moved proximally relative to outer tubular member 483, permitting the polyp or like tissue to be drawn by suction through window 485 and into the interior of outer tubular member 483. However, due to the number and placement of teeth 467 and 473 on trigger 463 and gear 469, respectively, as trigger 463 continues to be squeezed towards handle portion 457, teeth 467 are moved past teeth 473, causing gear 469 to become disengaged from trigger 463. This disengagement of gear 469 from trigger 463 allows spring 481 to pull carriage 475 back distally to its initial position, thereby causing the tissue extending through window 485 to be severed. The distal movement of carriage 475 simultaneously causes gear 469 to be rotated back to its initial angular position.

As can be seen, one advantageous feature of device 453 is that, even though vacuum source 454 is continuously being operated, no suction is applied to the contents of the uterus through device 453 unless trigger 463 is being operated since window 485 is kept closed by inner tubular member 487, except while trigger 463 is being actuated. When trigger 463 is no longer being actuated and returns to its inactive position, inner tubular member 487 returns to its most distal position, where it completely seals off window 485. In other words, device 453 does not require that any active steps be taken in order to close window 485 after operation of trigger 463 as the release of trigger 463 causes inner tubular member 487 to return to a position in which it closes window 485.

Figure 18:
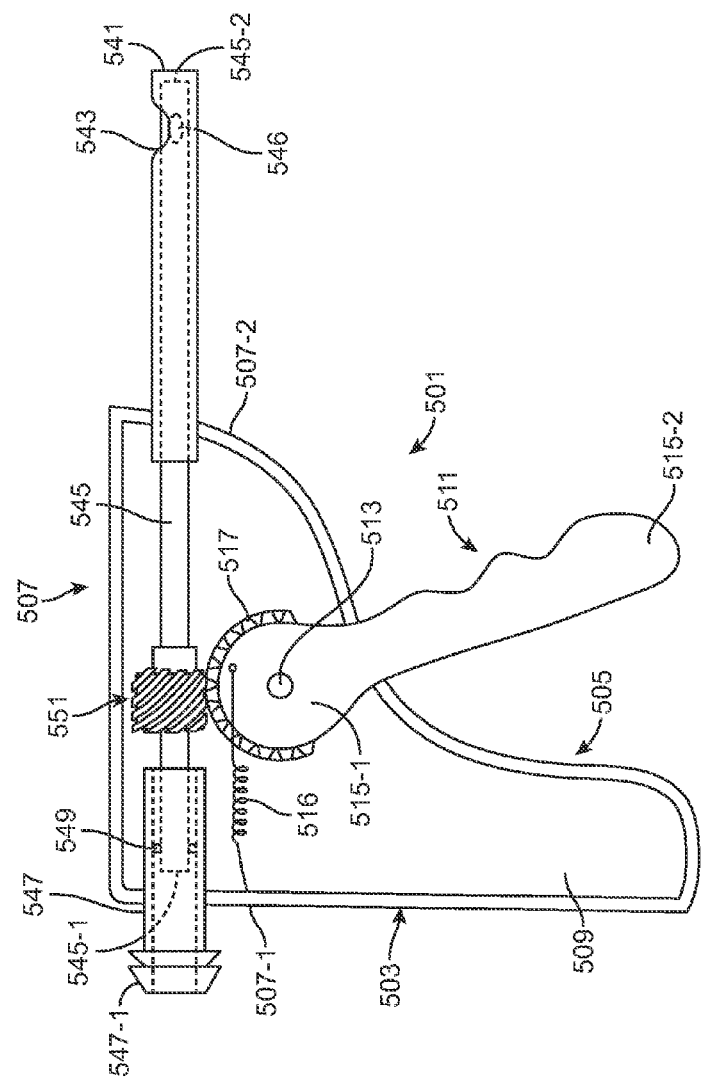
FIG. 18 is a side view of a first alternate embodiment of a tissue cutting device for use in the system of FIG. 16.

FIG. 18 is a side view of a first alternate embodiment of a tissue cutting device for use in system 451, the tissue cutting device being represented generally by reference numeral 501. Device 501 comprises a gun-shaped housing 503, which includes a handle portion 505 and a barrel portion 507. Housing 503 is formed from a pair of matching housing halves 509, the right housing half not shown in FIG. 18 to thereby reveal the interior of housing 503.

Figure 18A:
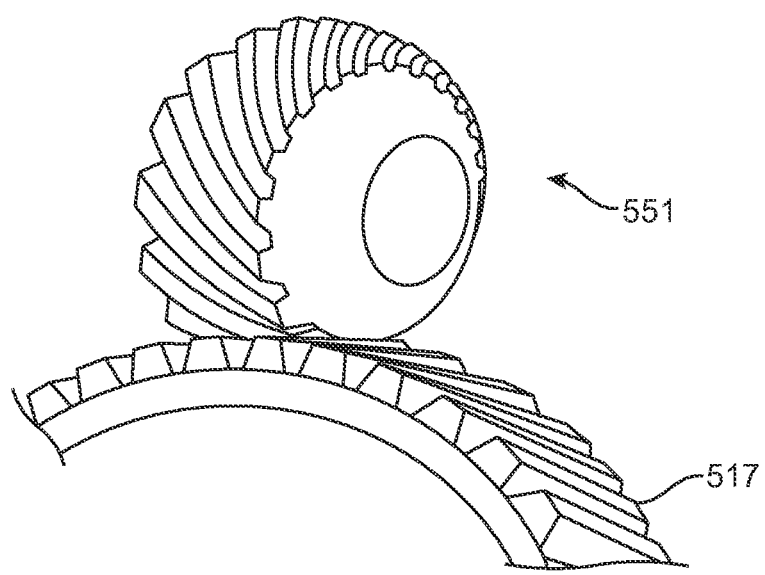
FIG. 18(a) is a fragmentary perspective view showing the helical gears of FIG. 18.

Device 501 also comprises a trigger 511, which is pivotally mounted to housing 503 about a pivot pin 513. Trigger 511 is shaped to include a first end 515-1 positioned inside of housing 503 and a second end 515-2 positioned outside of housing 503. First end 515-1 is rounded in profile and shaped to include a helical gear 517 (see also FIG. 18(a)) extending along much of its circumference. A spring 516 connected at one end to a proximal end 507-1 of barrel portion 507 and at the opposite end to first end 515-1 of trigger 511 is used to bias second end 515-2 of trigger 511 away from handle portion 509.

Device 501 further comprises an outer tubular member 541 fixedly mounted to housing 503 and extending distally from a distal end 507-2 of barrel portion 507. Outer tubular member 541 is similar to outer tubular member 106 or to outer tubular member 181, and includes a window 543 through which a polyp or similar tissue may pass to the interior of member 541.

Device 501 further comprises an inner tubular member 545, which includes a proximal end 545-1 and a distal end 545-2. Proximal end 545-1 is disposed within a vacuum connector 547 fixedly mounted at proximal end 507-1 of barrel portion 507. Connector 547 has a barbed proximal end 547-1 adapted for insertion into vacuum tube 130. An O-ring 549 is inserted around proximal end 545-1 of inner tubular member 545 to provide a vacuum seal around inner tubular member 545. Distal end 545-2 of inner tubular member 545 is disposed within outer tubular member 541. A transverse opening 546 is provided in inner tubular member 545 proximate to distal end 545-2. Opening 546 is appropriately positioned on inner tubular member 545 so that, by appropriately rotating inner tubular member 545, opening 546 becomes aligned with opening 543 of outer tubular member 541.

Device 501 further comprises a helical gear 551 inserted over and fixedly coupled to an intermediate portion of inner tubular member 545, helical gear 551 being engaged with helical gear 517. Helical gear 551 and helical gear 517 are appropriately dimensioned so that one trigger stroke results in one complete rotation of inner tubular member 545. It should be noted that, unlike, for example, inner tubular member 107, inner tubular member 545 does not move translationally, but rather, only rotates.

In use, vacuum connector 547 is connected to vacuum source 454, and outer tubular member 541 is inserted into the patient (either via access device 13 or otherwise) and positioned so that window 543 is aligned with a polyp or similar targeted tissue. Next, trigger 511 is squeezed towards handle portion 505. As trigger 511 is drawn towards handle portion 505, gear 517 on trigger 511 causes gear 551 to turn which, in turn, causes inner tubular member 545 to rotate. During a portion of its rotation, opening 546 in inner tubular member 545 comes into alignment with window 543 of outer tubular member 541. During this period in which opening 546 and window 543 are aligned, suction is able to be applied to window 543, and a polyp or similar targeted tissue may be drawn through both window 543 and opening 546. Then, as inner tubular member 545 continues to rotate, opening 546 moves out of angular alignment with window 543, causing the polyp or like tissue to be severed. Thereafter, as trigger 511 is released, inner tubular member 545 rotates back to its initial angular position.

One advantageous feature of device 501 is that, even if vacuum source 454 is continuously being operated, no suction is applied to the contents of the uterus through device 501, except during a short portion of the trigger stroke in which window 543 and opening 546 are aligned with one another. This is because, before trigger 511 is actuated and after trigger 511 returns to its inactive position, opening 546 is not aligned with window 543. Consequently, device 501 does not require that any active steps be taken in order to close window 543 after operation of trigger 511 as the release of trigger 511 causes inner tubular member 545 to return to a position in which it closes window 543.

Figure 19:
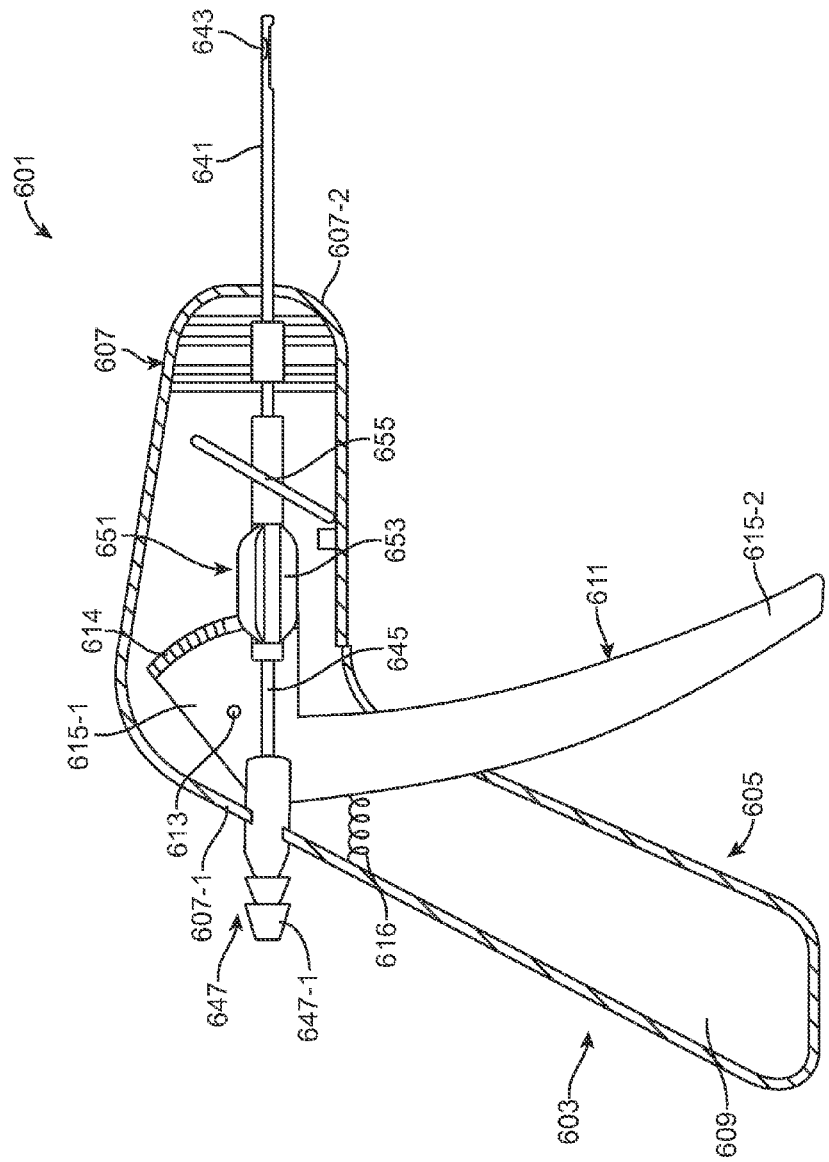
FIG. 19 is a side view of a second alternate embodiment of a tissue cutting device for use in the system of FIG. 16.

FIG. 19 is a side view of a second alternate embodiment of a tissue cutting device for use in system 451, the tissue cutting device being represented generally by reference numeral 601. Device 601 comprises a gun-shaped housing 603 having a handle portion 605 and a barrel portion 607. Housing 603 is formed from a pair of matching housing halves 609, the right housing half not being shown in FIG. 19 to reveal the interior of housing 603.

Device 601 also comprises a trigger 611, which is pivotally mounted to housing 603 about a pivot pin 613. Trigger 611 includes a first end 615-1 positioned inside of housing 603 and a second end 615-2 positioned outside of housing 603. First end 615-1 is wedge-shaped and includes a multi-toothed gear 614 arranged along its wide end. A spring 616 connected at one end to a proximal end 607-1 of barrel portion 607 and at the opposite end to first end 615-1 of trigger 611 is used to bias second end 615-2 of trigger 611 away from handle portion 609.

Device 601 further comprises an outer tubular member 641 fixedly mounted to housing 603 and extending distally from a distal end 607-2 of barrel portion 607. Outer tubular member 641 is similar to outer tubular member 106 or to outer tubular member 181, and includes a window 643 through which a polyp or similar tissue may pass to the interior of outer tubular member 641.

Device 601 further comprises an inner tubular member 645. Inner tubular member 645 is similar in shape to inner tubular member 487 and includes a proximal end and a distal end. The proximal end of inner tubular member 645 is disposed within a vacuum connector 647 fixedly mounted at proximal end 607-1 of barrel portion 607. Connector 647 has a barbed proximal end 647-1 adapted for insertion into vacuum tube 130. An O-ring (not shown) may be inserted around the proximal end of inner tubular member 645 within connector 647 to provide a vacuum seal around inner tubular member 645. The distal end of inner tubular member 645 is disposed within outer tubular member 641.

Device 601 further comprises a coupling member 651 inserted over inner tubular member 645 and fixedly coupled thereto for translational and rotation movement. Coupling member 651 comprises a proximal portion 653 and a distal portion 655. Proximal portion 653 comprises an elongated spur gear engaged with gear 614 in such a way that, as trigger 611 is pivoted, gear 614 rotates, thereby causing inner tubular member 645 to rotate. Distal portion 655 comprises a wobble member that causes coupling member 651 and inner tubular member 645 to move proximally as trigger 611 is squeezed and to move distally as trigger 611 is released.

In use, vacuum connector 647 is connected to vacuum source 454, and outer tubular member 641 is inserted into the patient (either via access device 13 or otherwise) and positioned so that window 643 is aligned with a polyp or similar targeted tissue. Next, trigger 611 is squeezed towards handle portion 605. As trigger 611 is drawn towards handle portion 605, gear 614 on trigger 611 causes proximal portion 653 of coupling member 651 to turn which, in turn, causes inner tubular member 645 to rotate. At the same time that inner tubular member 645 is rotating, distal portion 655 of coupling member 651 causes inner tubular member 645 to be moved proximally in front of window 643, thereby allowing suction to be applied to window 643 and causing the polyp or similar targeted tissue to be drawn through window 643 into the interior of outer tubular member 641. Thereafter, as trigger 611 is released, inner tubular member 645 is caused to rotate back to its initial angular position and is caused to move distally back to it is initial translational position. As inner tubular member 645 moves distally across window 643, the tissue extending through window 643 is severed by the moving inner tubular member 645.

One advantageous feature of device 601 is that, even if vacuum source 454 is continuously being operated, no suction is applied to the contents of the uterus through device 601, except during a portion of the trigger stroke in which the distal end of inner tubular member 645 is moved proximally sufficiently to open window 643. This is because, before trigger 611 is actuated and after trigger 611 returns to its inactive position, window 643 is closed off by inner tubular member 645. Consequently, device 601 does not require that any active steps be taken in order to close window 643 after operation of trigger 611 as the release of trigger 611 causes inner tubular member 645 to return to a position in which it closes window 643.

Figure 20:
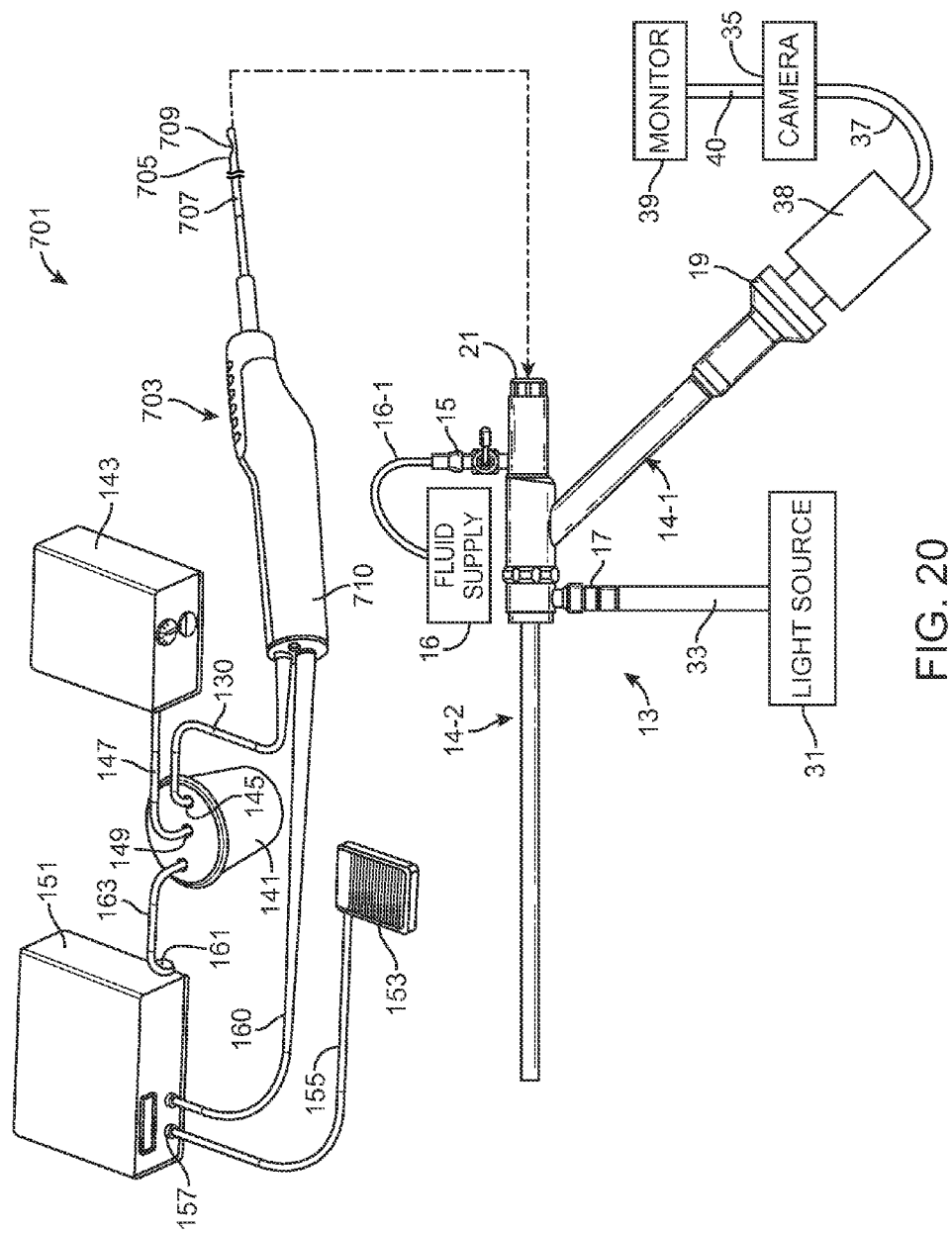
FIG. 20 is a perspective view of a fourth embodiment of a tissue removal system constructed according to the teachings of the disclosure.
Figure 21A:
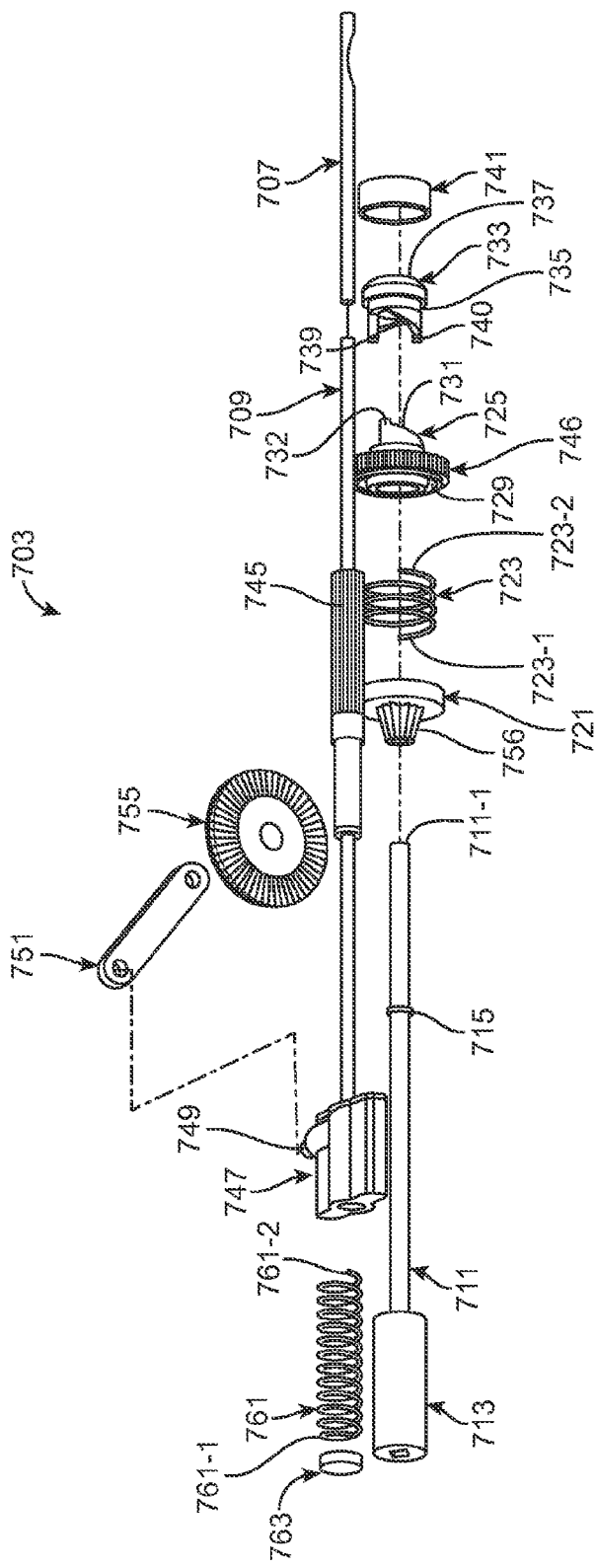
FIG. 21(a) is a partly exploded perspective view of the tissue cutting device shown in FIG. 20, certain components of the device, such as the device housing, not being shown.
Figure 21E:
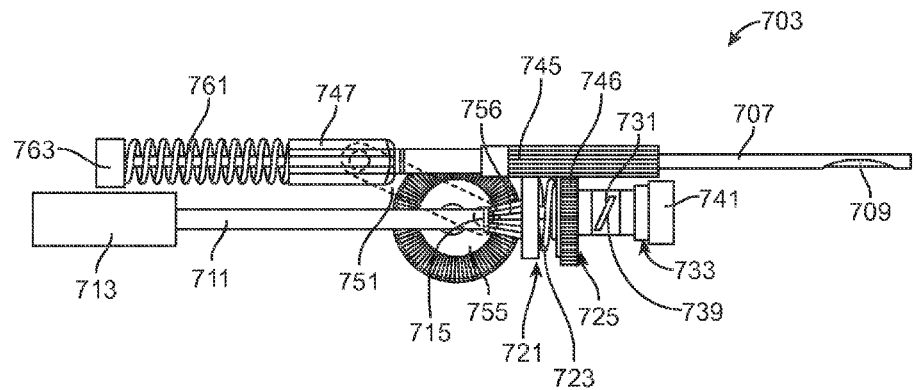
FIGS. 21(e) through 21(g) show the tissue cutting device of FIG. 21(a) at different stages in its operation.
Figure 21F:
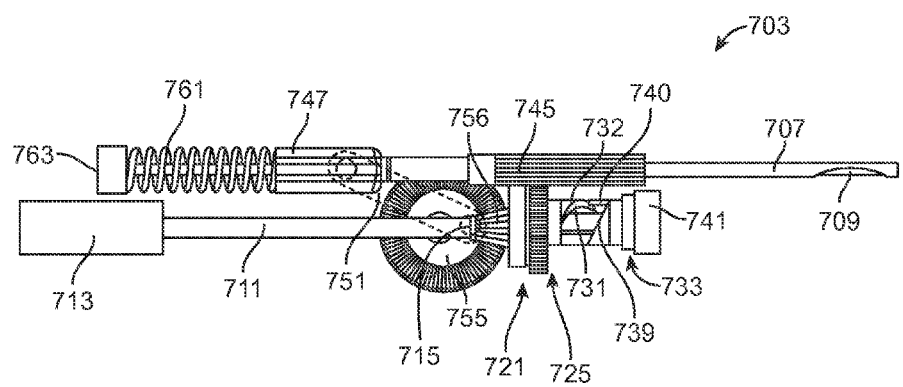
Figure 21G:
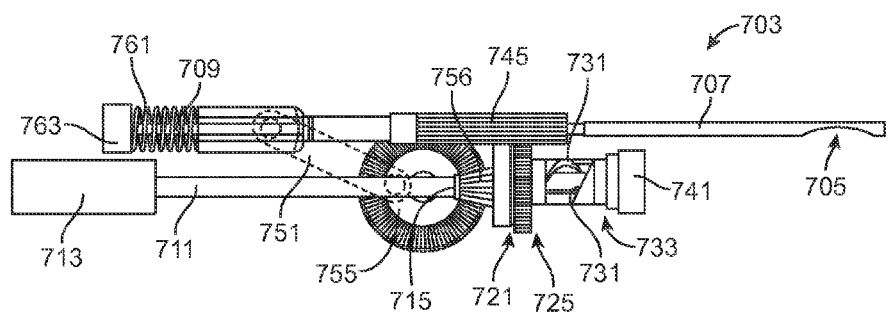

FIG. 20 depicts a fourth embodiment of a tissue removal system constructed according to the teachings of the disclosure, the tissue removal system being represented generally by reference numeral 701. System 701 is similar in many respects to system 11. One difference between the two systems is that, whereas motor unit 151 and vacuum source 143 of system 11 are coupled together via cable 165 so as to be either switched on together or switched off together, motor unit 151 and vacuum source 143 are not coupled together. Instead, in system 701, vacuum source 143 is continuously operating (unless system 701 is completely shut down) whereas motor unit 151 is switched on and off using a foot switch 153. Another difference between system 11 and system 701 is that, whereas system 11 comprises tissue cutting device 41, system 701 comprises a tissue cutting device 703. As will hereinafter be described, device 703 is designed so that, when foot switch 153 is depressed, suction from vacuum source 143 is applied to the patient through a resection window 705 in an outer tubular member 707 in device 703 and, thereafter, when foot switch 153 is no longer depressed, device 701 no longer permits suction from vacuum source 143 to be applied to the patient through window 705 due to a passive, entirely mechanical arrangement for moving an inner tubular member 709 in such a way as to close window 705.

Referring now to FIGS. 21(a) through 21(g), there are shown various views of device 703, certain components of device 703, such as the device housing 710 (which is shown in FIG. 20), not being shown in FIGS. 21(*a*) through 21(*g*) for clarity, and other components of device 703 being shown in some but not others of FIGS. 21(*a*) through 21(*g*).

Device 703 comprises a rotatable drive shaft 711. Drive shaft 711 includes at its proximal end a drive socket 713 adapted to be mechanically coupled to an external drive shaft (not shown). A washer 715 is fixedly mounted or integrally formed on drive shaft 711 at an intermediate location thereon.

Device 703 further comprises a cone clutch/bevel gear 721, a cone spring 723, and a cone clutch/spur gear 725, all three components being loosely inserted over, i.e., floating on, drive shaft 711. The proximal end of cone clutch/bevel gear 721 abuts the distal end of washer 715. A proximal end 723-1 of cone clutch spring 723 sits within a groove 727 provided in the distal end of cone clutch/bevel gear 721. A distal end 723-2 of cone clutch spring 723 sits within a groove 729 provided in the proximal end of cone clutch/spur gear 725. The distal end of cone clutch/bevel gear 721 and the proximal end of cone clutch/spur gear 725 are complementarily shaped to selectively permit mating engagement with one another. The distal end of cone clutch/spur gear 725 is shaped to include a cam 731.

Device 703 further comprises a cap 733 inserted over and fixedly mounted to distal end 711-1 of shaft 711 for rotation therewith. Cap 733 comprises a proximal portion 735 and a distal portion 737. Proximal portion 735 is shaped to include a cam 739 engageable in the manner hereinafter described with cam 731 of cone clutch/spur gear 725. Distal portion 737 comprises a dome-shaped member adapted to rotatably sit within a bearing 741 fixed to the inside of housing 710.

Device 703 further comprises a pinion gear 745 inserted over and fixedly mounted to inner tubular member 709 at an intermediate location thereon. Pinion gear 745 is engaged with and coupled for rotation to teeth 746 of cone clutch/spur gear 725.

Device 703 further comprises a driver 747 inserted over and fixedly mounted to inner tubular member 709, driver 747 abutting the proximal end of pinion gear 745. Driver 747 includes a mounting post 749, which is used to receive one end of a bell crank 751. The opposite end of bell crank 751 is mounted on a post 753 formed on a bevel gear 755, bevel gear 755 being engaged with teeth 756 on cone clutch/bevel gear 721.

Device 703 further comprises a spring 761 inserted over inner tubular member 709. Spring 761 comprises a proximal end 761-1 fixed to a cap 763 on the inside of housing 710 and a distal end 761-2 fixed to the proximal end of drive 747.

The manner in which device 703 may be operated is illustrated in FIGS. 21(*e*) through 21(*g*). As seen best in FIG. 21(*e*), prior to actuation of device 703, cone clutch/spur gear 725 and cap 733 are angularly positioned relative to one another so that cam 731 of cone clutch/spur gear 725 is aligned with cam 739 of cap 733. In addition, teeth 756 of cone clutch/bevel gear 721 are engaged with bevel gear 755, and teeth 746 of cone clutch/spur gear 725 are engaged with pinion gear 745. Notwithstanding the above, there is no movement of the aforementioned components prior to actuation of device 703.

With the depression of foot switch 153, the external drive shaft that is coupled to motor unit 151 begins to rotate. Because this external drive shaft is rotationally coupled to drive socket 713, the rotation of the external drive shaft causes drive socket 713 and drive shaft 711 to rotate. As drive shaft 711 begins to rotate, cap 733, which is fixed to distal end 711-1 of drive shaft 711, also begins to rotate. By contrast, cone clutch/spur gear 725 is not fixedly coupled for rotation to drive shaft 711, and as cap 733 initially begins to rotate, cone clutch/spur gear 725 does not rotate. The rotation of cap 733 relative to cone clutch/spur gear 725 causes cam 739 to begin to slide along cam 731, causing cap 733 to push cone clutch/spur gear 725 and spring 723 proximally towards cone clutch/bevel gear 721. This proximal pushing of cone clutch/spur gear 725 and spring 723 towards cone clutch/bevel gear 721 continues until a contact point 740 at the end of cam 739 engages a contact point 732 at the end of cam 731. With contact points 740 and 732 thus engaged with one another, as is shown in FIG. 21(*f*), cone clutch/spur gear 725 becomes engaged with and coupled for rotation to cap 733. Moreover, the above-described proximal pushing of cone clutch/spur gear 725 towards cone clutch/bevel gear 721 results in cone clutch/spur gear 725 engaging cone clutch/bevel gear 721 such that cone clutch/bevel gear 721 is coupled for rotation to cone clutch/spur gear 725. Consequently, continued rotation of drive shaft 711 results in the simultaneous rotation of cap 733, cone clutch/spur gear 725 and cone clutch/bevel gear 721. As cone clutch/spur gear 725 rotates, pinion gear 745, which is engaged with cone clutch/spur gear 725, also rotates. This rotation of pinion gear 745, in turn, causes inner member 709 to rotate. At the same time, as cone clutch/bevel gear 721 rotates, bevel gear 755, which is engaged with cone clutch/bevel gear 721, also rotates. This rotation of bevel gear 755, in turn, causes bell crank 751 to move driver 747 back and forth in an oscillating fashion, with each rotation of bevel gear 755 corresponding to one back and forth cycle of driver 747. Because driver 747 is coupled for translational movement to inner member 709, proximal movement of driver 747 causes inner member 709 to retract relative to outer member 707, thereby opening resection window 705 (see FIG. 21(*g*)). Similarly, distal movement of driver 747 causes inner member 709 to return to its distal position within outer member 709, closing resection window 705 and cutting any tissue extending through window 705.

When it is desired to turn device 703 off, foot switch 153 is no longer depressed. This causes the external drive shaft to stop rotating, which, in turn, causes shaft 711 to stop rotating. Because cap 733 is fixed to shaft 711 for rotation, the cessation of rotation of shaft 711 causes a corresponding cessation of rotation of cap 733. Due to inertia, cone clutch/spur gear 725 does not cease rotating as quickly as does cap 733, and, as a result, cone clutch/spur gear 725 rotates relative to cap 733, causing cams 731 and 739 once again to come into in alignment with one another. The alignment of cams 731 and 739 with one another, in turn, causes spring 723 to open up and decouples the rotation of cone clutch/bevel gear 721 from cone clutch/spur gear 725. As can be appreciated, with the stoppage of rotation of cone clutch/spur gear 725, pinion gear 745 stops rotating and, thus, so does inner member 709. In addition, with the stoppage of rotation of cone clutch/bevel gear 721, bevel gear 755 stops rotating and driver 747 stops moving back and forth. If, when bevel gear 755 stops rotating, driver 747 and inner member 709 are positioned proximally, as in FIG. 21(*g*), spring 761 provides a return force sufficient to return driver 747 and inner member 709 to their respective distal positions. In this manner, device 703 assures that resection window 705 is not open when device 703 is not being used to cut tissue.

Figure 22A:
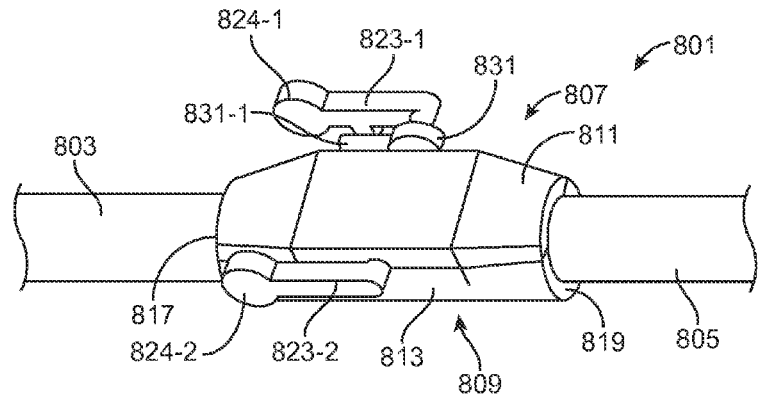
Figure 22B:
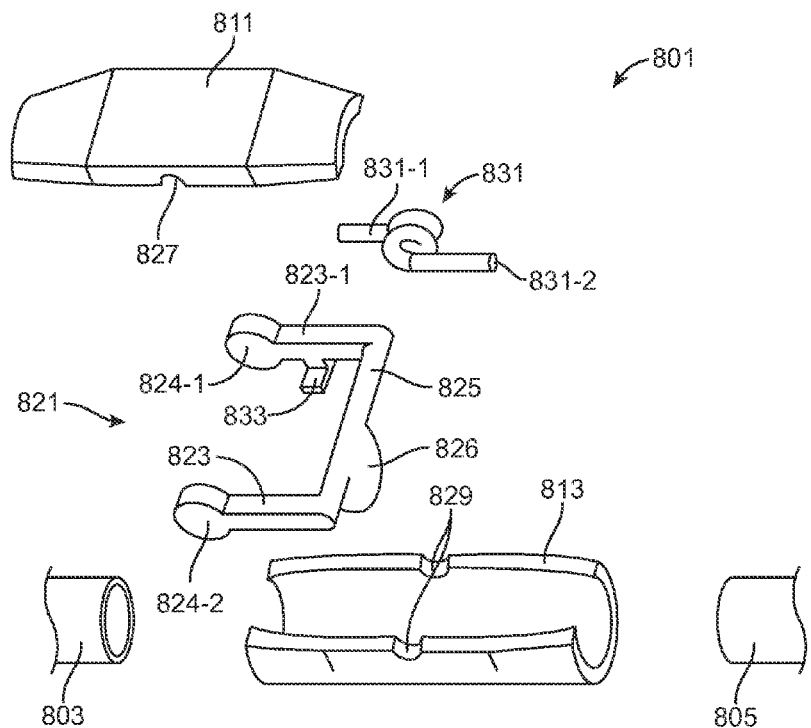

Referring now to FIGS. 22(*a*) through 22(*d*), there are shown various views of a first alternate embodiment of a tissue cutting device for use in system 701, the tissue cutting device being represented generally by reference numeral 801. Device 801, which is similar in certain respects to device 41, differs notably from device 41 in that device 801 includes a mechanical arrangement for keeping suction from being applied to resection window 119 of outer tubular member 106 when device 801 is not being used to cut tissue. Accordingly, whereas device 41 includes inner tubular member 107, device 801 instead includes a proximal inner tubular member 803, a distal inner tubular member 805, and a valved connector 807.

Connector 807 comprises a housing 809. Housing 809, in turn, comprises a top piece 811 and a bottom piece 813. Top piece 811 and bottom piece 813 are suitably joined together to define a hollow cavity 815, a proximal end 817, and a distal end 819. Member 803 is inserted into proximal end 817 of housing 809 and fixed thereto by suitable means, and member 805 is inserted into distal end 819 of housing 809 and fixed thereto by suitable means.

Connector 807 further comprises a clip 821. Clip 821 is a one-piece member which includes a pair of parallel side arms 823-1 and 823-2 and a transverse arm 825, transverse arm 825 interconnecting side arms 823-1 and 823-2. Side arm 823-1 is shaped to include an enlarged disc-shaped member 824-1 at an end distal to transverse arm 825, and side arm 823-2 is shaped to include an enlarged disc-shaped member 824-2 at an end distal to transverse arm 825. Side arms 823-1 and 823-2 are positioned outside of housing 809, with transverse arm 825 extending transversely through housing 809 using recesses 827 provided in top piece 811 and complementary recesses 829 provided in bottom piece 813. Transverse arm 825 is shaped to include a door 826 extending perpendicularly therefrom, door 826 being dimensioned to selectively block the flow of fluids through housing 809 in the manner described below.

Connector 807 further comprises a coil spring 831, which has a first end 831-1 fixed to a mounting post 833 extending from arm 823-1, and a second end 831-2 fixed to housing 809. Spring 831 is used to bias clip 821 so that, when device 801 is in its rest state, i.e., device 801 is not being used to cut tissue, clip 821 is positioned so that door 826 blocks the flow of fluids through housing 809 (see FIG. 22(c)). By contrast, when device 801 is used to cut tissue, proximal tubular member 803 is caused to rotate, and, in turn, housing 809, which is mechanically coupled to member 803, is caused to rotate. This rotation of housing 809 effectively creates a centrifugal force that causes arms 823-1 and 823-2 to overcome the bias of spring 831 and to swing from an orientation generally parallel to the longitudinal axis of housing 809 to an orientation generally perpendicular to the longitudinal axis of housing 809, thereby resulting in door 826 being pivoted upwardly towards top piece 811 of housing 809 (see FIG. 22(d)). With door 826 thus pivoted, fluid is permitted to flow through housing 809. Thereafter, when the rotation of proximal tubular member 803 stops and there is no longer any force overcoming that provided by spring 831, spring 831 causes clip 821 to be pivoted back to its original orientation, wherein door 826 blocks the flow of fluid through housing 809. Therefore, as can be seen, device 801 permits suction to be applied to distal member 805 only when device 801 is being used to cut tissue.

Referring now to FIGS. 23(a) through 23(f), there are shown various views of a second alternate embodiment of a tissue cutting device for use in system 701, the tissue cutting device being represented generally by reference numeral 851. Device 851 is similar in many respects to device 801, the principal difference between the two devices being that, whereas device 801 comprises valved connector 807, device 851 comprises a valved connector 857.

Connector 857 comprises a tubular housing 859 shaped to include a hollow cavity 865, a proximal end 867, and a distal end 869. Member 803 is inserted into proximal end 867 of housing 859 and fixed thereto by suitable means, and member 805 is inserted into distal end 869 of housing 859 and fixed thereto by suitable means. Housing 859 also comprises a transverse opening 870 provided in a top wall 871 of housing 859 midway between proximal end 867 and distal end 869, and further comprises a pair of transverse slots 872-1 and 872-2 provided in top wall 871 on proximal and distal sides, respectively, of opening 870.

Connector 857 further comprises a slide 881. Slide 881 may be a one-piece member shaped to include an elongated post 883 having a square flange 884 at one end of post 883 and a disc-shaped knob 887 at an opposite end of post 883. Slide 881 also includes a paddle 889 extending downwardly from the flange 884. Paddle 889 is appropriately dimensioned to be inserted through opening 870 and to selectively block the flow of fluids through housing 859 in the manner described below.

Connector 857 further comprises a support bracket 891. Bracket 891 includes a pair of legs 893-1 and 893-2 and a bridge 895, bridge 895 interconnecting legs 893-1 and 893-2 at their respective top ends. The bottom ends of legs 893-1 and 893-2 are appropriately dimensioned to be inserted into and securely retained within openings 872-1 and 872-2, respectively. Bridge 895 includes a transverse slot 897. Legs 893-1 and 893-2 and slot 897 are appropriately dimensioned for post 883 to extend therethrough, with knob 887 being retained by the top surface of bridge 895.

Connector 857 further comprises a coil spring 899. Coil spring 899 is inserted coaxially around post 883 of slide 881, with a first end 899-1 of coil spring 899 seated on flange 884 and a second end 899-2 of coil spring 899 abutting the bottom surface of bridge 895.

Figure 23A:
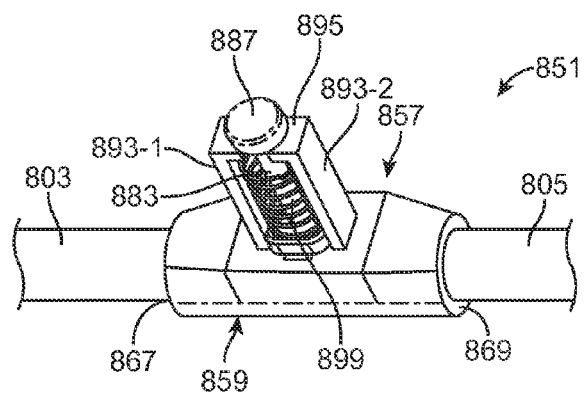
FIGS. 23(a) through 23(f) are fragmentary perspective in a rest state, fragmentary exploded perspective, fragmentary longitudinal section in a rest state, fragmentary longitudinal section in a rotating state, transverse sectional in a rest state, and transverse sectional in a rotating state views, respectively, of a second alternate embodiment of a tissue cutting device for use in the system of FIG. 20.
Figure 23B:
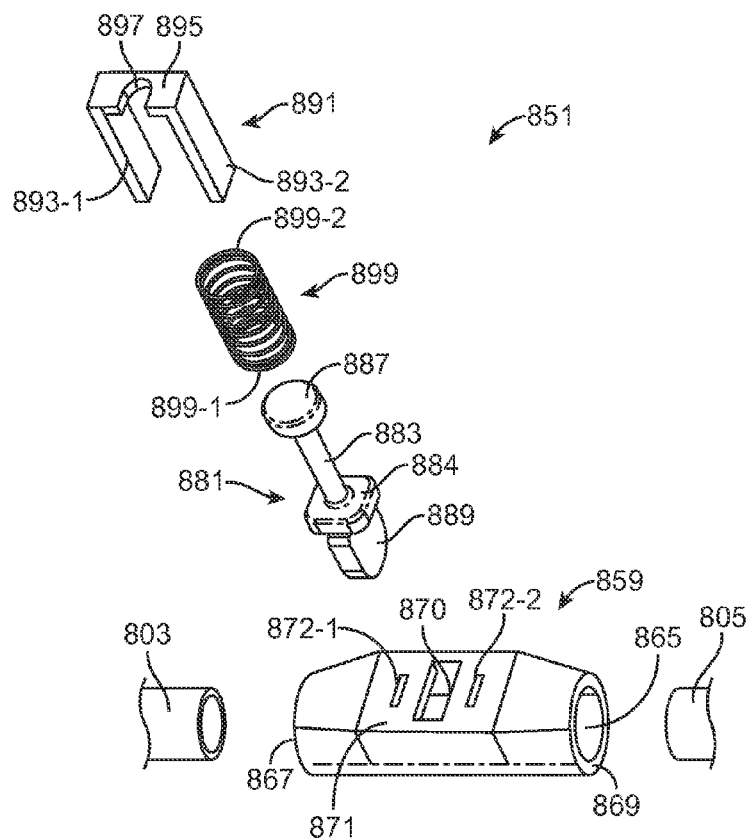
Figure 23C:
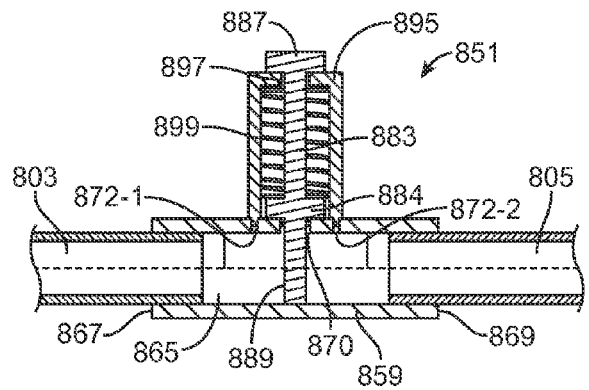
Figure 23D:
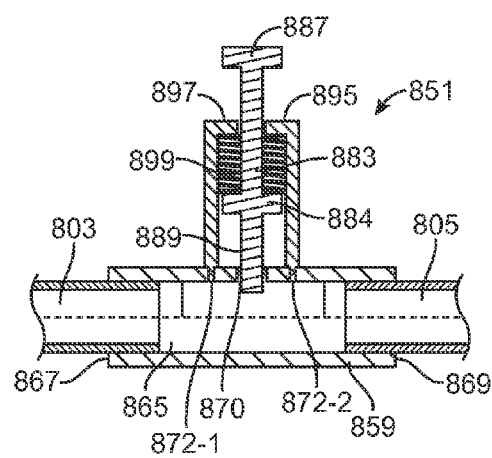
Figures 23E, 23F:
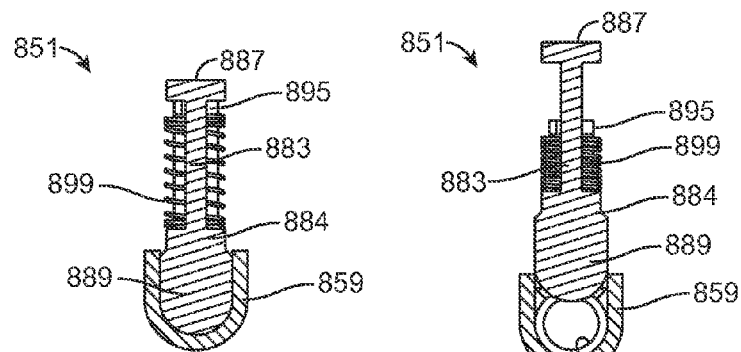

When device 851 is in its rest state, i.e., device 851 is not being used to cut tissue, slide 881 is biased by spring 899 downwardly into cavity 865 so that paddle 889 blocks the flow of fluids through housing 859 (see FIGS. 23(c) and 23(e)). By contrast, when device 851 is used to cut tissue, proximal tubular member 803 is caused to rotate and, in turn, housing 859, which is mechanically coupled to member 803 is also caused to rotate. This rotation of housing 859 effectively creates a centrifugal force that causes slide 881 to overcome the bias of spring 899 and to slide radially outwardly away from cavity 865, thereby allowing fluids to flow between proximal end 867 and distal end 869 of housing 859 (see FIGS. 23(d) and 23(f)). Thereafter, when the rotation of proximal tubular member 803 stops and there is no longer any force overcoming that provided by spring 899, spring 899 forces slide 881 downwardly such that paddle 889 once again blocks the flow of fluid through housing 859. Therefore, as can be seen, device 851 permits suction to be applied to distal member 805 only when device 851 is being used to cut tissue.

Referring now to FIGS. 24(a) through 24(d), there are shown various views of a third alternate embodiment of a tissue cutting device for use in system 701, the tissue cutting device being represented generally by reference numeral 901. Device 901 is similar in many respects to device 801, the principal difference between the two devices being that, whereas device 801 comprises valved connector 807, device 901 comprises a valved connector 907.

Connector 907 comprises a housing 909. Housing 909, in turn, comprises a top piece 911 and a bottom piece 913. Top piece 911 and bottom piece 913 are suitably joined together to define a hollow cavity 915, a proximal end 917, and a distal end 919. Top piece 911 includes a vent 912.

Member 803 is inserted into proximal end 917 of housing 909 and fixed thereto by suitable means, and member 805 is inserted into distal end 919 of housing 909 and fixed thereto by suitable means.

Connector 907 further comprises a clip 921. Clip 921 may be a one-piece member shaped to include a pair of parallel side arms 923-1 and 923-2 and a transverse arm 925, transverse arm 925 interconnecting side arms 923-1 and 923-2. Side arm 923-1 includes an enlarged disc-shaped member 924-1 at an end distal to transverse arm 925, and side arm 923-2 includes an enlarged disc-shaped member 924-2 at an end distal to transverse arm 925. Side arms 923-1 and 923-2 are positioned outside of housing 909, with transverse arm 925 extending transversely through housing 909 using recesses 927 provided in top piece 911 and complementary recesses 929 provided in bottom piece 913. Transverse arm 925 is shaped to include a door 926 extending perpendicularly therefrom, door 926 being dimensioned to selectively cover vent 912 in the manner described below.

Connector 907 further comprises a coil spring 931 having a first end 931-1 fixed to a mounting post 933 extending from arm 923-1, and a second end 931-2 fixed to a post 932 on housing 909. Spring 931 is used to bias clip 921 so that, when device 901 is in its rest state, i.e., device 901 is not being used to cut tissue, clip 921 is positioned so that door 926 does not cover vent 912 (see FIG. 24(c)).

Connector 907 further comprises a clip 941. Clip 941 may be a one-piece member shaped to include a pair of parallel side arms 943-1 and 943-2 and a transverse arm 945, transverse arm 945 interconnecting side arms 943-1 and 943-2. Side arms 943-1 and 943-2 are positioned outside of housing 909, with transverse arm 945 extending transversely through housing 909 using recesses 947 provided in top piece 911 and complementary recesses 949 provided in bottom piece 913. Transverse arm 945 is shaped to include a damper 946 extending perpendicularly therefrom, damper 946 being dimensioned to block the flow of fluid through housing 909 in the manner described below.

Connector 907 further comprises a coil spring 951 having a first end 951-1 fixed to a mounting post 953 extending from arm 923-1, and a second end 951-2 fixed to a post 954 on housing 909. Spring 951 is used to bias clip 941 so that, when device 901 is in its rest state, i.e., device 901 is not being used to cut tissue, clip 941 is positioned so that damper 946 blocks the flow of fluid through housing 900 (see FIG. 24(c)).

Figure 24A:
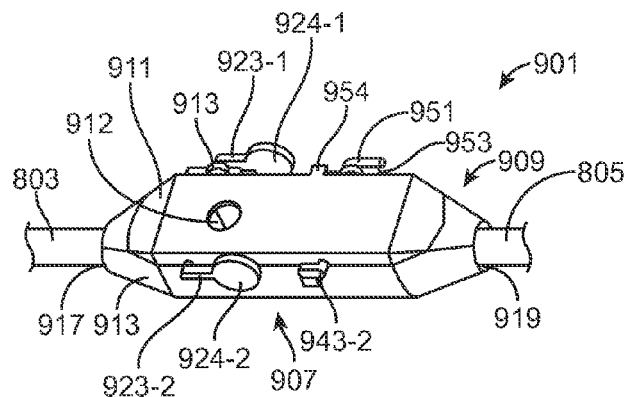
FIGS. 24(a) through 24(d) are fragmentary perspective in a rest state, fragmentary exploded perspective, fragmentary longitudinal section in a rest state, and fragmentary longitudinal section in a rotating state views, respectively, of a third alternate embodiment of a tissue cutting device for use in the system of FIG. 20.
Figure 24B:
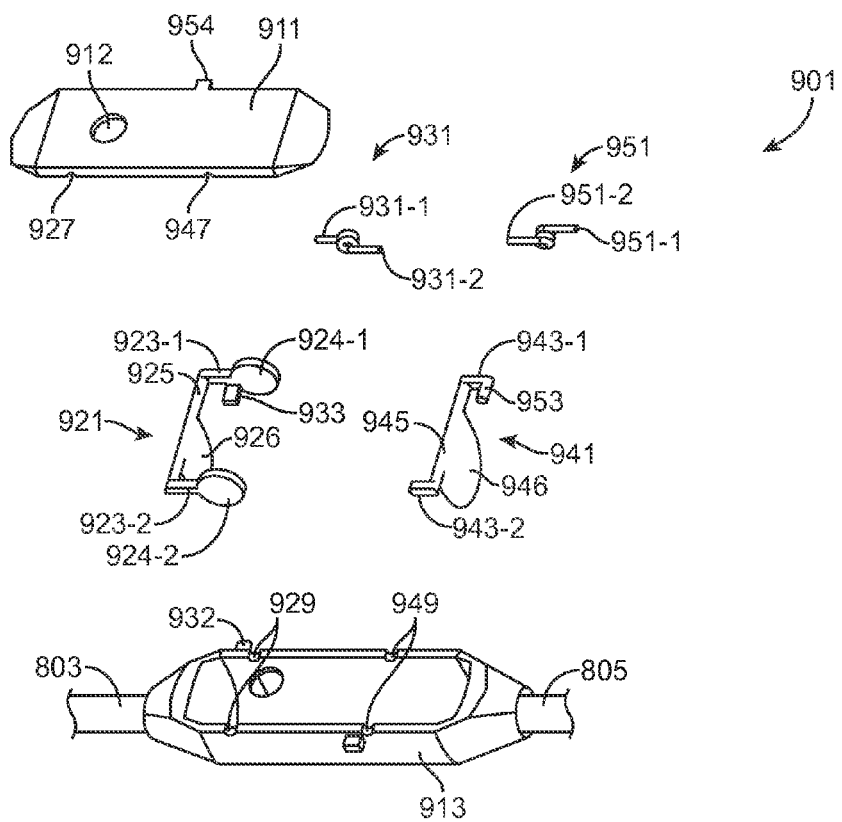
Figure 24C:
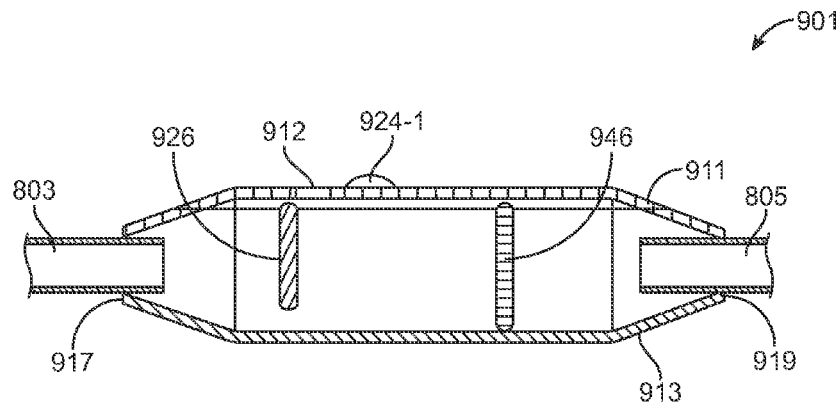
Figure 24D:
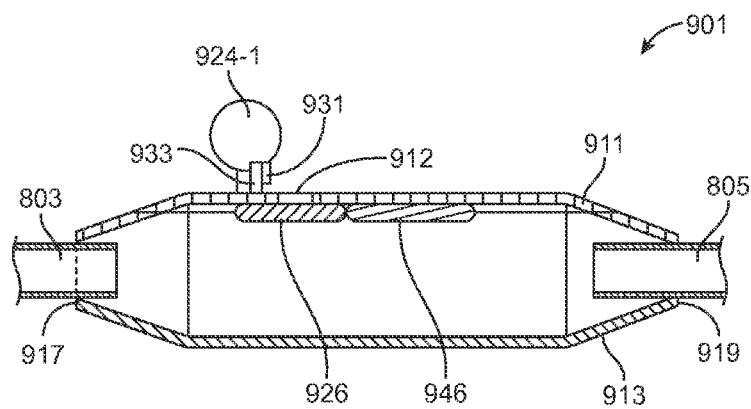

When device 901 is not being used to cut tissue, door 926 does not cover vent 912, and damper 946 blocks the flow of fluid through housing 900 (see FIG. 24(c)). As a result, suction applied to member 803 results in air being drawn into housing 909 through vent 912, and, consequently, no suction is applied to member 805. By contrast, when device 901 is used to cut tissue, proximal tubular member 803 is caused to rotate, and, in turn, housing 909, which is mechanically coupled to member 803, is caused to rotate. This rotation of housing 909 effectively creates a centrifugal force that causes arms 923-1 and 923-2 to overcome the bias of spring 931 and to swing from an orientation generally parallel to the longitudinal axis of housing 909 to an orientation generally perpendicular to the longitudinal axis of housing 909, thereby resulting in door 926 being pivoted upwardly to cover vent 912. With vent 912 covered, the continued application of suction to member 803 overcomes the bias of spring 951 and causes damper 946 to be pivoted upwardly, thereby allowing fluid to flow from the distal end 919 of housing 909 to the proximal end 917 of housing 909 (see FIG. 24(d)). Thereafter, when the rotation of proximal tubular member 803 stops and there is no longer any force overcoming that provided by spring 931, spring 931 causes clip 921 to be pivoted back to its original orientation away from covering vent 912. With vent 912 once again uncovered, the suction applied to member 803 causes air to be drawn in through vent 912, thereby minimizing the suction applied to damper 946, which then, due to spring 951, pivots back to its original position blocking the flow of fluid through housing 909. Therefore, as can be seen, device 901 permits suction to be applied to distal member 805 only when device 901 is being used to cut tissue.

Referring now to FIGS. 25(a) through 25(d), there are shown various views of a fourth alternate embodiment of a tissue cutting device for use in system 701, the tissue cutting device being represented generally by reference numeral 971. Device 971 is similar in many respects to device 801, the principal difference between the two devices being that, whereas device 801 comprises valved connector 807, device 971 comprises a valved connector 977.

Connector 977 comprises a housing 979. Housing 979, in turn, comprises a top piece 981 and a bottom piece 983. Top piece 981 and bottom piece 983 are suitably joined together to define a generally tubular proximal portion 984 and a generally tubular distal portion 986, proximal portion 984 and distal portion 986 being in fluid communication with one another, proximal portion 984 having a greater maximum diameter than distal portion 986. Proximal portion 984 is shaped to include a proximal end 987, an outwardly tapering proximal wall 988, an inwardly tapering distal wall 989, and a side wall 990, side wall 990 interconnecting proximal wall 988 and distal wall 989. Three transverse openings 991 are evenly spaced around the circumference of side wall 990. Distal portion 986 is shaped to include a distal end 992. Member 803 is inserted into proximal end 987 of proximal portion 984 of housing 909 and fixed thereto by suitable means, and member 805 is inserted into distal end 992 of distal portion 986 of housing 909 and fixed thereto by suitable means.

Connector 977 further comprises three balls 993 disposed within proximal portion 984. Balls 993 are appropriately dimensioned to selectively cover openings 991 in the manner described below. Although not shown, proximal portion 984 may be shaped to include one or more tracks to assure that each ball 993 is aligned with a corresponding opening 991. Also, it should be understood that while connector 977 has been described herein as having three balls 993 and three openings 991, connector 977 may be modified to include a greater or lesser number of balls 993 and a corresponding number of openings 991. Connector 977 further comprises a duckbill valve 995 securely mounted within distal portion 986 of housing 979.

Figure 25A:
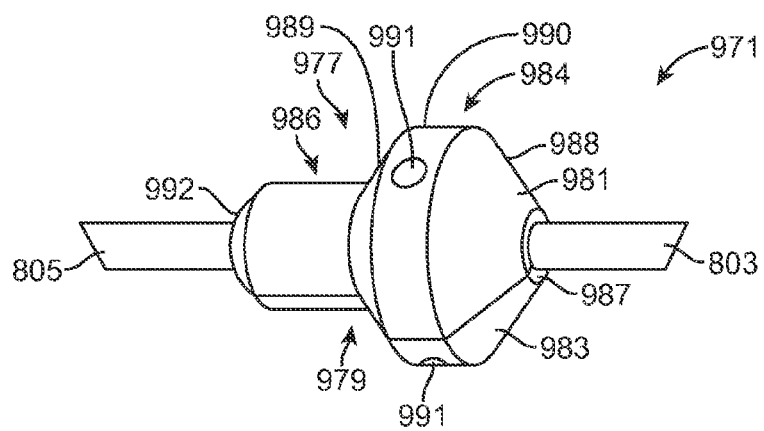
FIGS. 25(a) through 25(d) are fragmentary perspective in a rest state, fragmentary partly exploded perspective, fragmentary longitudinal section in a rest state, and fragmentary longitudinal section in a rotating state views, respectively, of a fourth alternate embodiment of a tissue cutting device for use in the system of FIG. 20.
Figure 25B:
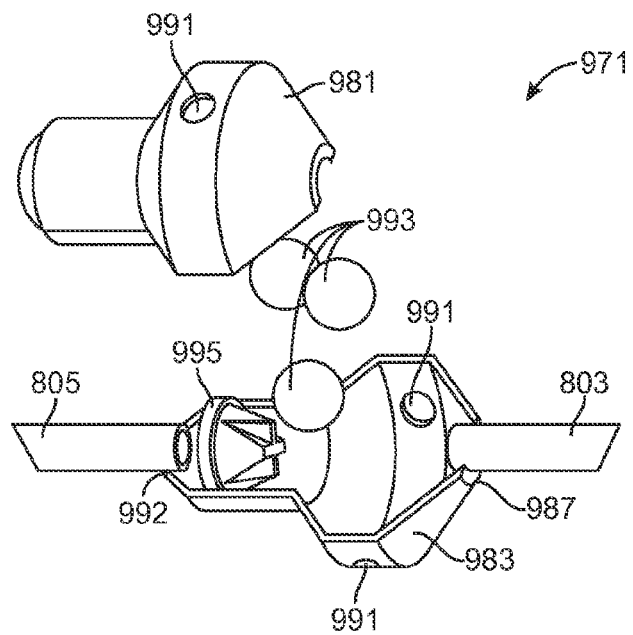
Figure 25C:
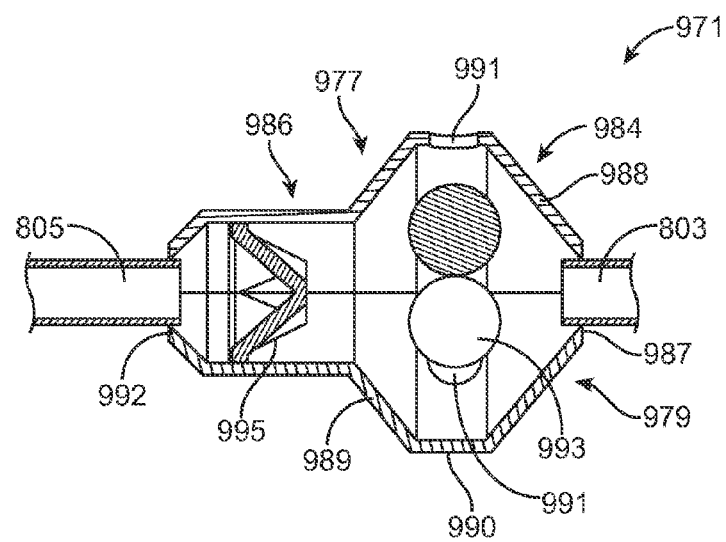
Figure 25D:
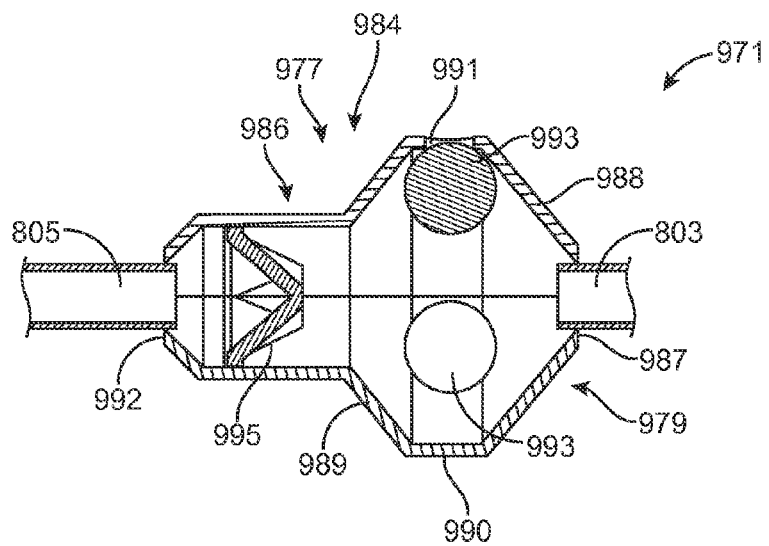

When device 971 is not being used to cut tissue, balls 993 do not cover openings 991 (see FIG. 25(c)). As a result, suction applied to member 803 results in air being drawn into housing 979 through openings 991, and, consequently, no suction is applied to member 805. By contrast, when device 971 is used to cut tissue, proximal tubular member 803 is caused to rotate, and, in turn, housing 979, which is mechanically coupled to member 803, is caused to rotate. This rotation of housing 979 effectively creates a centrifugal force that moves balls 993 radially outwardly, where they cover openings 991 (see FIG. 25(d)). With openings 991 thus covered, the continued application of suction to member 803 opens valve 995 and results in suction being applied to member 805. Thereafter, when the rotation of proximal tubular member 803 stops, and balls 993 are no longer forced radially outwardly against openings 991, thereby leaving openings 991 uncovered, the suction applied to member 803 causes air to be drawn in through opening 991. As a result, valve 995 is closed once again, and no suction is applied to member 805. Therefore, as can be seen, device 971 permits suction to be applied to distal member 805 only when device 971 is being used to cut tissue.

Figure 26A:
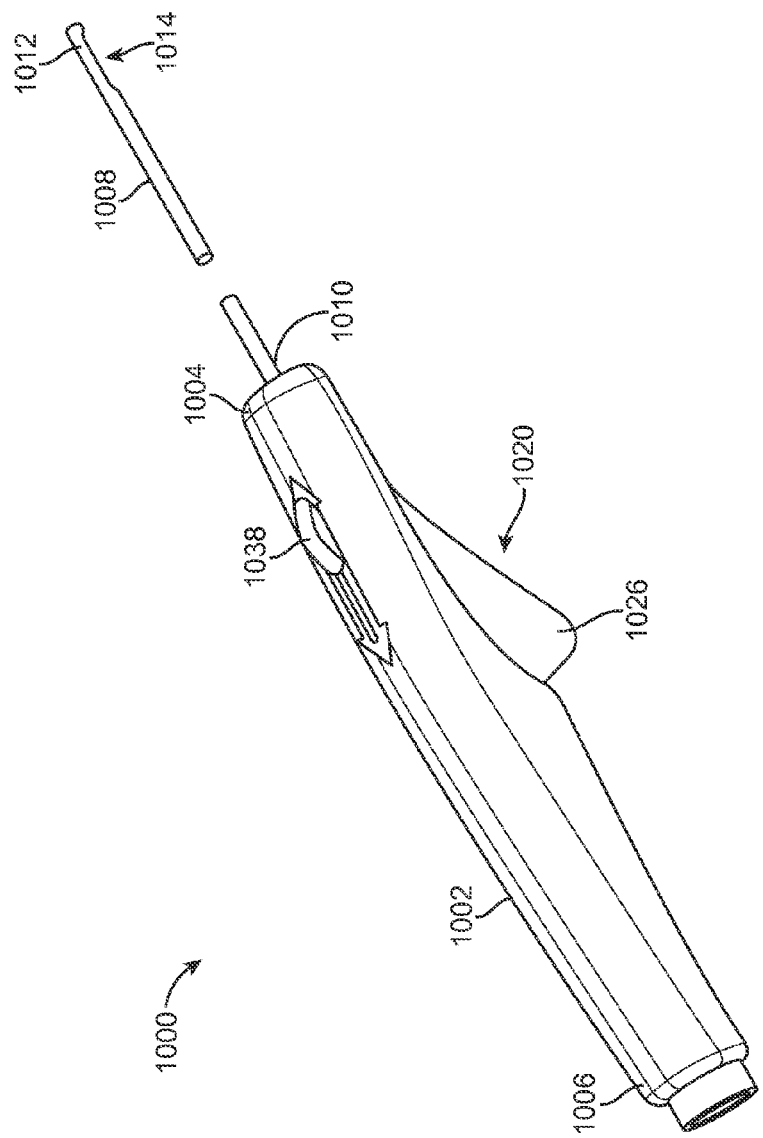
FIG. 26(a) is a perspective view of yet another embodiment of a tissue cutting device.
Figure 26B:
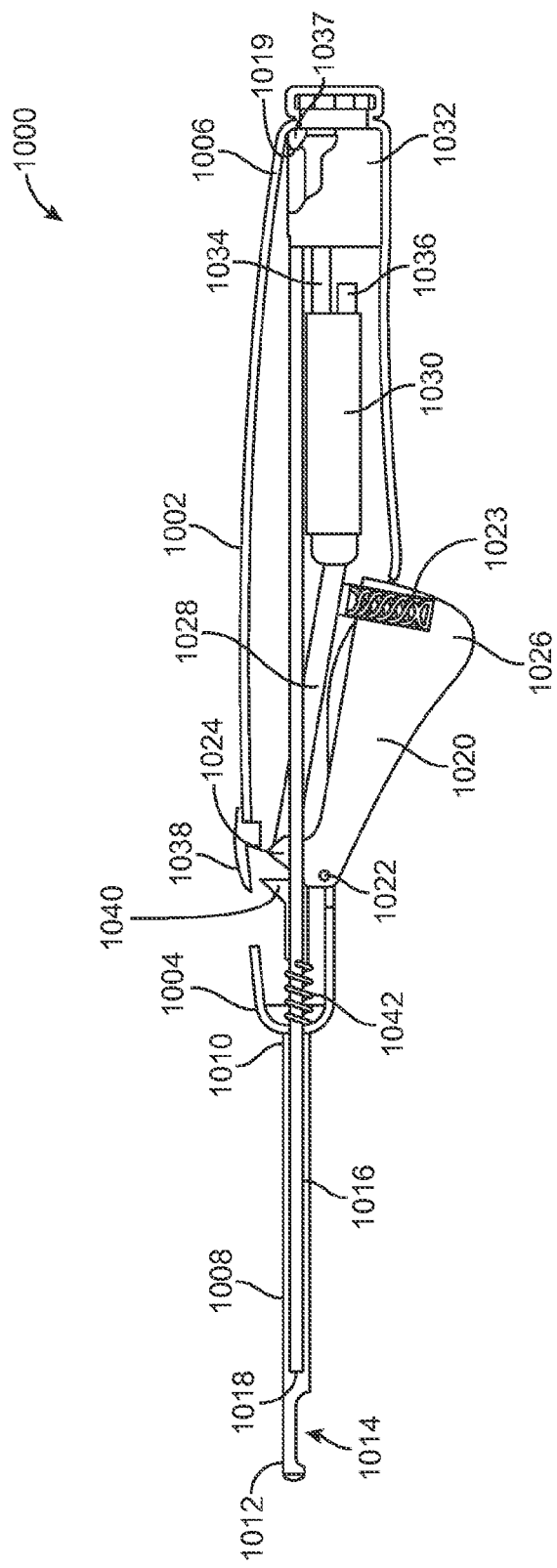
FIGS. 26(b) and 26(c) are cross-sectional views of the tissue cutting device in FIG. 26(a) in vacuum mode and cutting mode, respectively.
Figure 26C:
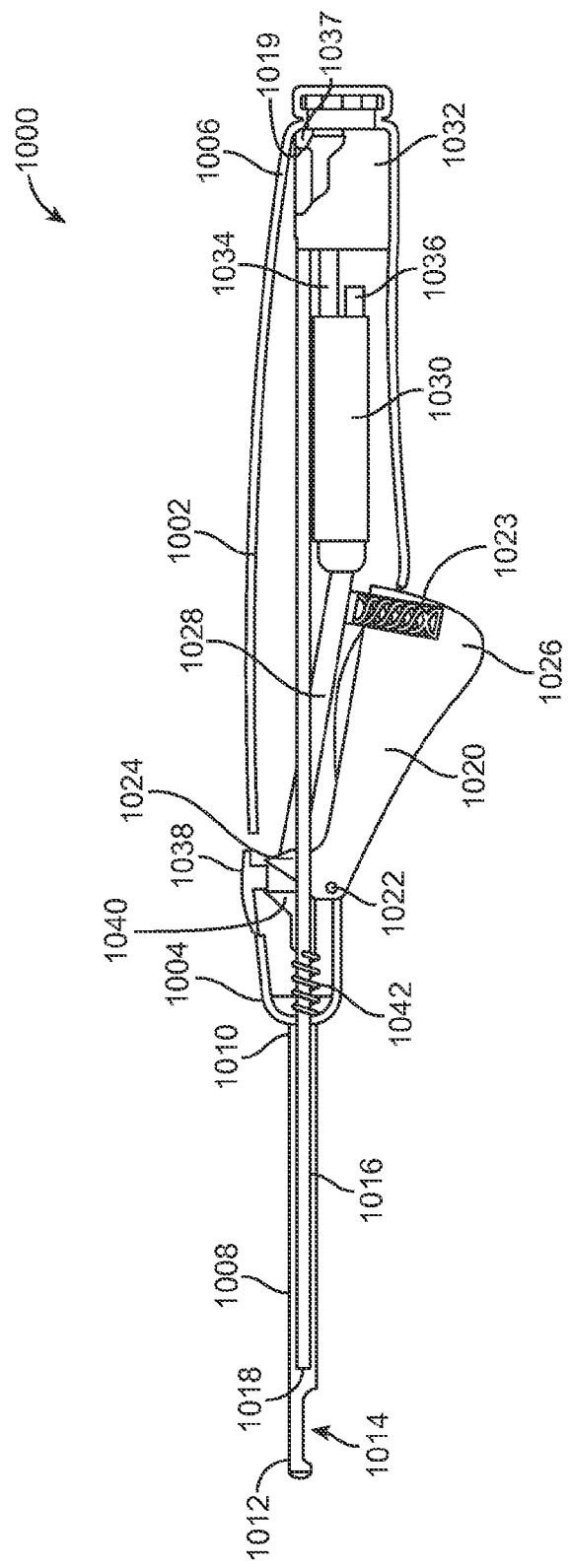

FIGS. 26(a)-26(c) illustrate still another embodiment of a tissue removal device 1000. The tissue removal device 1000 in this embodiment is not attached to a motor unit or a vacuum source. Rather, the tissue removal device 1000 includes manually operated assemblies, described in further detail below, for creating vacuum and for cutting tissue.

Tissue removal device 1000 is similar in many respects to the tissue removal devices previously described herein. For example, similar to the other tissue removal devices described herein, tissue removal device 1000 includes a housing 1002 having a distal end 1004 and a proximal end 1006, an outer tubular member 1008 having a proximal end 1010 coupled to the distal end 1004 of the housing 1002 and a distal end 1012 having a tissue resection window 1014, and an inner tubular member 1016 configured for sliding within the outer tubular member 1008. The outer tubular member 1008 may be configured for transcervical insertion. Additionally or alternatively, the outer tubular member 1008 is configured for insertion through a working channel of an endoscopic instrument so that the tissue resection window 1014 is positioned in an interior region of a patient's body. The distal end 1012 of the outer tubular member 1008 may be conformable or rigid. The outer tubular member 1008 may be configured to rotate relative to the housing 1002. The inner tubular member 1016 is hollow, and includes an open distal end 1018, an open proximal end 1019, and a lumen extending between the open distal end 1018 and the open proximal end 1019. The distal end 1018 of the inner tubular member 1016 includes a cutting edge for severing tissue projecting into the tissue resection window 1014.

However, whereas the other tissue removal devices described herein are configured for being operated while attached to a vacuum source and/or a motor unit, the tissue removal device 1000 is completely manually operated. Thus, the tissue removal device 1000 is "tetherless," because it does not require tubes or cables for connecting the device 1000 to a vacuum source and/or a motor unit.

The tissue removal device 1000 comprises an actuator in the form of a manually operated actuator, or trigger 1020 coupled to the housing 1002 by a pinned connection 1022. The trigger 1020 includes a first end 1024 positioned inside of the housing 1002, and a second end 1026 positioned outside of the housing 1002. The trigger 1020 is coupled to the housing 1002 such that a user may hold the housing 1002 in one hand and actuate the trigger 1020 by squeezing, thus rotating the trigger 1020 towards the housing 1002 about the pivot point 1022. A spring 1023 coupled to the housing 1002 and the trigger 1020 causes the trigger 1020 to be biased away from the housing 1002, as shown in FIGS. 26(*a*)-26(*c*). In this manner, when the trigger 1020 is released after being actuated, the spring 1023 restores the trigger 1020 to its un-actuated position away from the housing 1002. It should be understood that the individual components of the device 1000 illustrated in FIGS. 26(*a*)-26(*c*) are not necessarily drawn to scale, and that FIGS. 26(*a*)-26(*c*) are provided for illustrating the principles of the disclosed embodiments.

The first end 1024 of the trigger 1020 is coupled to a piston 1028, which is disposed within a vacuum generation chamber 1030. Rotation of the trigger 1020 about the pin 1022 moves the piston 1028 within the vacuum generation chamber 1030. In particular, moving the trigger 1020 towards the housing 1002 causes the piston 1028 to be pulled out of the vacuum generation chamber 1030. The vacuum generation chamber 1030 is coupled to a removable tissue trap 1032 through a one-way valve 1034. The one-way valve 1034 allows air to be withdrawn from the tissue trap 1032 and into the vacuum generation chamber 1030 when the piston 1028 is moved distally relative to the vacuum generation chamber 1030. The one-way valve 1034 further prevents air from entering the tissue trap 1032 from the vacuum generation chamber 1030 due to movement of the piston 1028 proximally relative to the vacuum generation chamber 1030. Another one-way valve 1036 coupled to the vacuum generation chamber 1030 allows the vacuum generation chamber 1030 to expel air.

The proximal end 1019 of the inner tubular member 1016 is disposed within the tissue trap 1032. In this embodiment, when the inner tubular member 1016 is in a proximal position, as shown in FIGS. 26(*b*) and 26(*c*), the proximal end 1019 of the inner tubular member 1016 is in sealing engagement with a seal 1037 disposed within the tissue trap 1032. For example, the seal 1037 may be a rubber plug, and the proximal end 1019 of the inner tubular member 1016 may be in a sealing engagement with the plug 1037, so that vacuum created in the tissue trap 1032 is prevented from escaping through the lumen of the inner tubular member 1016. When the inner tubular member 1016 is moved in the distal direction, the seal 1037 unplugs the proximal end 1019 of the inner tubular member 1016, and the vacuum within the tissue trap 1032 escapes through the hollow inner tubular member 1016, thereby subjecting tissue adjacent to the tissue resection window 1014 to vacuum and pulling the tissue into the window 1014.

It should be well understood that the device 1000 could alternatively be configured such that the proximal end 1019 of the inner tubular member 1016 is in a sealing engagement with a seal in the tissue trap 1032 when the inner tubular member 1016 is in a distal position, rather than a proximal position. In this alternative embodiment, the sealing engagement between the proximal end 1019 of the inner tubular member 1016 and the seal is opened when the inner tubular member 1016 is moved in a proximal direction relative to the housing 1002. In this alternative embodiment, vacuum is created within the tissue trap 1032 while the tissue resection window 1014 is closed.

The trigger 1020 is selectively operatively coupled to the inner tubular member 1016 by a sliding lever, or slider, 1038 coupled to the housing 1002. As shown in FIG. 26(*a*), the slider 1038 is configured for allowing a user to choose between "vacuum mode" and "cutting mode." In order to put the device 1000 in vacuum mode, the slider 1038 is displaced in a proximal position relative to the housing 1002, and in order to put the device 1000 in cutting mode, the sliding 1038 is displaced in a distal position relative to the housing 1002.

FIG. 26(*b*) depicts the device 1000 in vacuum mode, with the slider 1038 in its proximal position. When the device 1000 is in vacuum mode, actuation of the trigger 1020 pulls the piston 1028 distally within the vacuum generation chamber 1030, thereby pulling air out of the tissue trap 1032 through the one-way valve 1034 and creating a vacuum within the tissue trap 1032. When the trigger 1020 is released and pushed away from the housing 1002 by the spring 1023, the piston 1028 moves proximally through the vacuum generation chamber 1030, and air is thereby expelled from the chamber 1030 through the other one-way valve 1036. The trigger 1020 may be pumped several times to create sufficient vacuum within the tissue trap 1032. Alternatively, the device 1000 may be configured so that sufficient vacuum is created within the tissue trap 1032 with only a single squeeze of the trigger 1020.

In yet another alternative embodiment, rather than creating vacuum within the tissue trap 1032 that is later released through the inner tubular member 1016, the vacuum created by squeezing the trigger 1020 may immediately be applied to the tissue through the inner tubular member 1016. Thus, each time the trigger 1020 is squeezed, tissue is pulled into the resection window 1014. This embodiment does not require the seal 1037 between the proximal end 1019 of the inner tubular member 1016 and the tissue trap 1032.

After sufficient vacuum is created within the tissue trap 1032, the vacuum may be released and applied to tissue in order to suction tissue into the tissue resection window 1014, and the tissue within the window 1014 may be cut by putting the device 1000 in the cutting mode. In order to release the vacuum and cut the tissue, the slider 1038 is moved distally relative to the housing 1002 to put the device 1000 in cutting mode, as shown in FIG. 26(*c*). Switching to cutting mode may cause the trigger 1020 to become disengaged from the piston 1028. However, in this embodiment, the trigger 1020 remains coupled to the piston 1028 when the device 1000 is in cutting mode. As such, vacuum is created each time the trigger 1020 is actuated. In cutting mode, actuation of the trigger 1020 causes the first end 1024 of the trigger 1020 to contact the slider 1038 and push the slider 1038 in the distal direction. The distance covered by the slider 1038 during actuation of the trigger 1020 is approximately equal to the length of the window 1014 in the outer tubular member 1008. The slider 1038 contacts a block 1040 fixedly coupled to the inner tubular member 1016 so that distal movement of the slider 1038 causes distal movement of the inner tubular member 1016. As discussed above, distal movement of the inner tubular member 1016 breaks the seal between the proximal end 1019 of the inner tubular member 1016 and the tissue trap 1032, so that the vacuum created within the tissue trap 1032 is applied to tissue through the inner tubular member 1016. The vacuum applied through the inner tubular member 1016 causes tissue adjacent to the window 1014 to be pulled into the window 1014. Further distal movement of the inner tubular member 1016 causes the distal end 1018 of the inner tubular member 1016 to move across the window 1014, thereby severing the tissue extending into the window 1014. The severed tissue is suctioned proximally through the inner tube 1016 and into the tissue trap 1032. When the trigger 1020 is released and restored to its original position by the spring 1023, the inner tubular member 1016 is restored to the proximal position shown in FIGS. 26(*b*) and 26(*c*) by the spring 1042. At the completion of the tissue removal procedure, the tissue trap 1032 with the removed tissue therein is removed from the housing 1002.

Figure 27A:
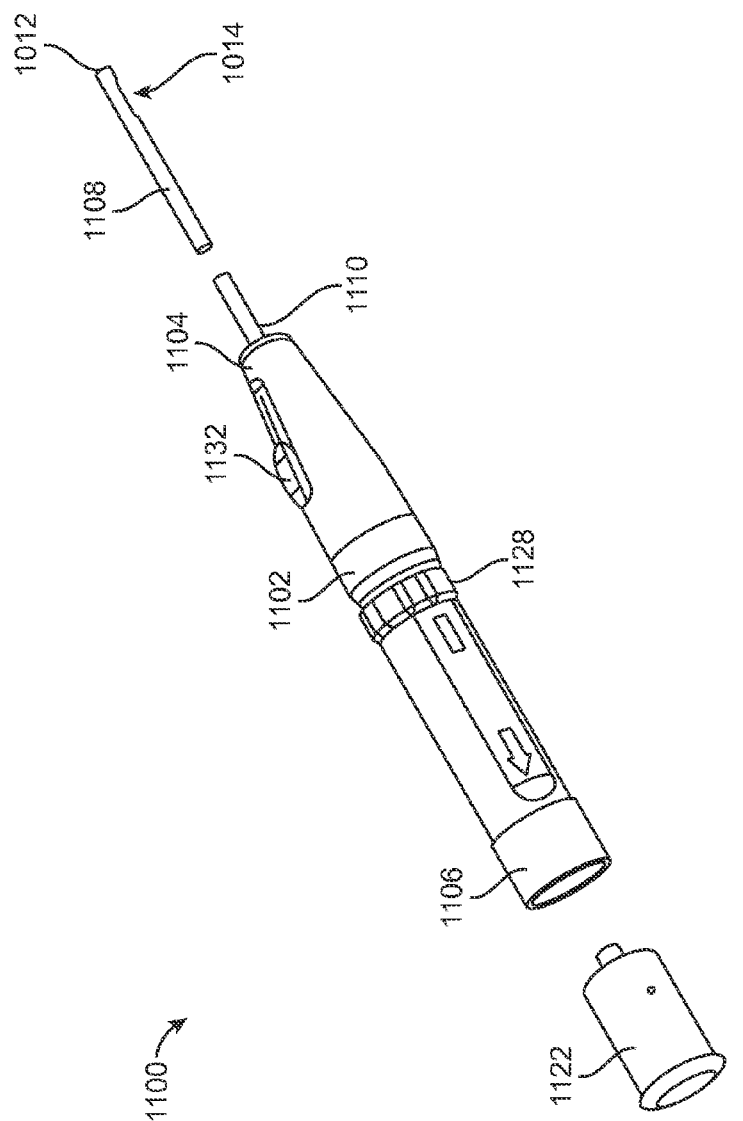
FIGS. 27(a) and 27(b) are perspective and cross-sectional views, respectively, of a still further embodiment of a tissue cutting device.
Figure 27B:
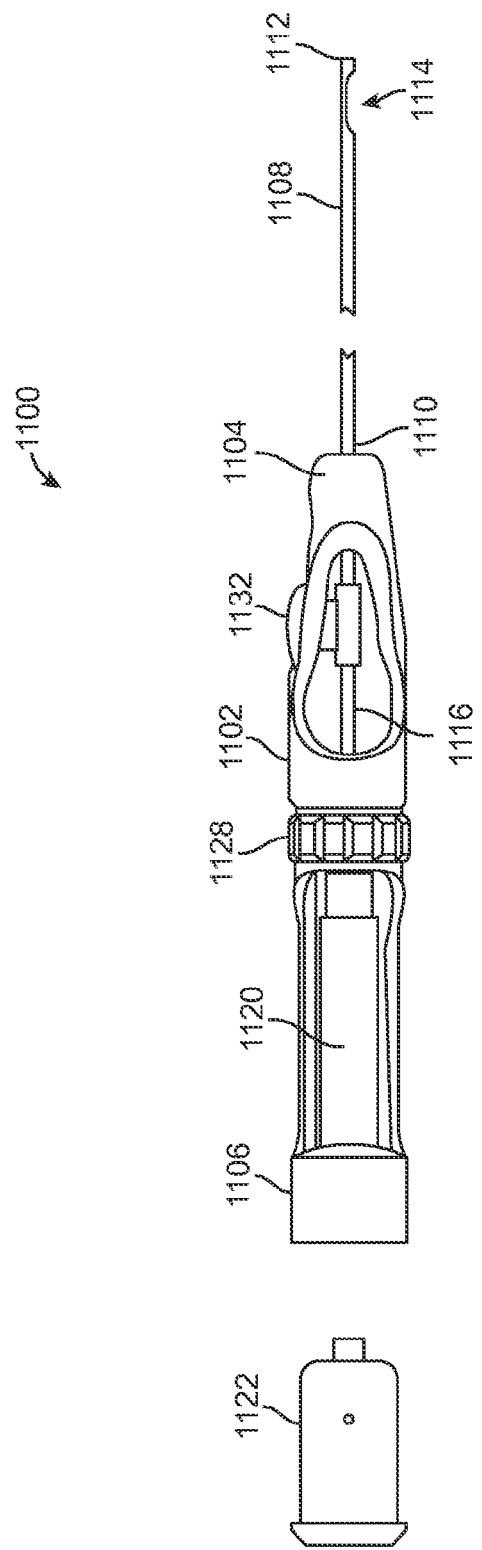

FIGS. 27(*a*) and 27(*b*) depict another embodiment of a tissue removal device 1100. Similar to the tissue removal device 1000 depicted in FIGS. 26(*a*)-26(*c*), the tissue removal device 1100 in this embodiment is not attached to a motor unit or a vacuum source. Rather, the tissue removal device 1100 includes manually operated assemblies, described in further detail below, for creating vacuum and for cutting tissue.

Tissue removal device 1100 is similar in many respects to the tissue removal devices previously described herein. For example, similar to the other tissue removal devices described herein, tissue removal device 1100 includes a housing 1102 having a distal end 1104 and a proximal end 1106, an outer tubular member 1108 having a proximal end 1110 coupled to the distal end 1104 of the housing 1102 and a distal end 1112 having a tissue resection window 1114, and an inner tubular member 1116 configured for sliding within the outer tubular member 1108. The outer tubular member 1108 is configured for transcervical insertion. Additionally or alternatively, the outer tubular member 1108 is configured for insertion through a working channel of an endoscopic instrument so that the tissue resection window 1114 is positioned in an interior region of a patient's body. The distal end 1112 of the outer tubular member 1108 may be conformable or rigid. The outer tubular member 1108 may be configured to rotate relative to the housing 1102. The inner tubular member 1116 is hollow, and includes an open distal end, an open proximal end, and a lumen extending between the open distal end and the open proximal end. The distal end of the inner tubular member 1116 includes a cutting edge for severing tissue projecting into the tissue resection window 1114.

However, whereas the other tissue removal devices described herein are configured for being operated while attached to a vacuum source and/or a motor unit, the tissue removal device 1100 is completely manually operated. Thus, the tissue removal device 1100 is "tetherless," because it does not require tubes or cables for connecting the device 1100 to a vacuum source and/or a motor unit.

Similar to the tissue removal device 1000 depicted in FIGS. 26(*a*) through 26(*c*), the tissue removal device 1100 includes a vacuum generation chamber 1120 coupled to a tissue trap 1122 through a one-way valve (not shown). The one-way valve allows air to be withdrawn from the tissue trap 1122 and into the vacuum generation chamber 1120, and also prevents air from entering the tissue trap 1122 from the vacuum generation chamber 1120. The tissue removal device 1100 also includes another one-way valve (not shown), similar to the one-way valve 1036 in the device 1000, coupled to the vacuum generation chamber 1120 for allowing air to be expelled from the vacuum generation chamber 1120.

The proximal end of the inner tubular member 1116 is disposed within the tissue trap 1122. Similar to the embodiment shown in FIGS. 26(*a*)-26(*c*), when the inner tubular member 1116 is in a proximal position, the proximal end of the inner tubular member 1116 is in sealing engagement with a seal (not shown) disposed within the tissue trap 1122. For example, the seal may be a rubber plug (not shown), and the proximal end of the inner tubular member 1116 may be in a sealing engagement with the plug, so that vacuum created in the tissue trap 1022 is prevented from escaping through the lumen of the inner tubular member 1116. When the inner tubular member 1116 is moved in the distal direction, the seal is opened, and the vacuum within the tissue trap 1122 escapes through the hollow inner tubular member 1116, thereby subjecting tissue adjacent to the tissue receiving window 1114 to vacuum and pulling the tissue into the window 1114.

It should be well understood that the device 1100 could alternatively be configured such that the proximal end of the inner tubular member 1116 is in a sealing engagement with the seal in the tissue trap 1122 when the inner tubular member 1116 is in a distal position, rather than a proximal position. In this alternative embodiment, the sealing engagement between the proximal end of the inner tubular member 1116 and the seal would be opened when the inner tubular member 1116 is moved in a proximal direction relative to the housing 1102. In this alternative embodiment, vacuum is created within the tissue trap 1122 while the tissue resection window 1114 is closed.

The vacuum generation chamber 1120 is coupled (e.g., through a piston) to an actuator in the form of an actuation member, such as a ring 1128, disposed around a tubular portion of the housing 1102, and configured for sliding axially relative to the housing 1102. The ring 1128 is coupled to the vacuum generation chamber 1120 in a manner such that pulling the ring 1128 proximally relative to the housing 1102 creates vacuum in the tissue trap 1122 by pulling air out of the tissue trap 1122 through the one-way valve between the chamber 1120 and the tissue trap 1122. The ring 1128 may be spring-biased in the distal position, or may be manually moved between the proximal and distal positions. When the ring 1128 returns to the distal position, air is expelled from the vacuum generation chamber 1120 through the other one-way valve (not shown). The ring 1128 may be moved back and forth relative to the housing 1102 several times to create sufficient vacuum within the tissue trap 1122, or the device 1100 may be configured to that sufficient vacuum is created within the tissue trap 1122 by sliding the ring 1028 proximally one time.

After sufficient vacuum is created within the tissue trap 1122, the vacuum may be released and applied to tissue in order to suction the tissue into the tissue resection window 1114, and the tissue within the window 1114 may be cut. In order to release the vacuum and cut the tissue, a sliding button, or slider, 1132 coupled to the housing 1102 and fixedly coupled to the inner tubular member 1116 is moved in the distal direction relative to the housing 1102, which causes the inner tubular member 1116 to move distally relative to the outer tubular member 1108. Similar to the embodiment shown in FIGS. 26(*a*)-26(*c*), moving the inner tubular member 1116 in the distal direction opens the seal between the proximal end of the inner tubular member 1116 and the tissue trap 1122 so that the vacuum created in the tissue trap 1122 is applied through the inner tubular member 1116 and tissue is pulled into the window 1114 in the outer tubular member 1108. The inner tubular member 1116 continues to move in the distal direction until the window 1114 is closed and the tissue is severed. The severed tissue is suctioned proximally through the inner tubular member 1116 and into the tissue trap 1122. When the slider 1132 is moved back to the proximal position, the inner tubular member 1116 is pulled back proximally into the proximal position. The slider 1132 and/or the inner tubular member 1116 may be spring-loaded to return to the proximal position without any action from the user, or may be manually returned to the proximal position. At the completion of the procedure, the tissue trap 1122 with the removed tissue therein is removed from the housing 1102.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although this disclosure has been provided in the context of certain embodiments and examples, it will be understood by those skilled in the art that the disclosure extends beyond the specifically disclosed embodiments to other alternative embodiments and/or uses of the embodiments and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present inventions disclosed herein should not be limited to the illustrated and/or described embodiments.

What is claimed is:

1. A tissue removal device, comprising:
   a housing;
   an outer tubular member coupled to the housing and having a distal portion including a tissue resection window;
   an inner tubular member slidably disposed within the outer tubular member and defining an inner lumen extending from an open distal end to an open proximal end, the open distal end comprising a cutting edge to sever tissue extending through the tissue resection window;
   a vacuum generation chamber disposed in the housing including a movable piston disposed in the vacuum generation chamber;
   a tissue trap disposed in or coupled to the housing, the tissue trap defining a sealed interior in fluid communication with the vacuum generation chamber via a one-way valve, so that air may be withdrawn from the tissue trap interior into the vacuum generation chamber by movement of the piston in a first direction, while air is prevented from entering the tissue trap interior from the vacuum generation chamber due to movement of the piston in a second direction opposite the first direction, wherein the open proximal end of the inner tubular member is disposed within the tissue trap interior; and
   a manual actuator moveably coupled to the housing and operatively connected to the piston, such that movement of the actuator relative to the housing causes movement of the piston within the vacuum generation chamber wherein the actuator is selectively operatively coupled to the inner tubular member such that movement of the actuator relative to the housing causes movement of the inner tubular member relative to the outer tubular member, wherein in a first configuration the actuator is not operatively coupled to the inner tubular member, and in a second configuration the actuator mechanically engages the inner tubular member such that movement of the actuator relative to the housing causes the open distal end of the inner tubular member to move distally across the tissue resection window as the actuator is moved relative to the housing.

2. The device of claim 1, wherein the actuator is coupled to the housing by a pinned connection, such that rotation of the actuator about the pin moves the piston within the vacuum generation chamber.

3. The device of claim 1, wherein the actuator is selectively operatively coupled to the inner tubular member by a slider having a first position relative to the housing in which the actuator is not operatively coupled to the inner tubular member, and a second position relative to the housing in which the actuator mechanically engages the inner tubular member such that movement of the actuator relative to the housing causes the open distal end of the inner tubular member to move distally across the tissue resection window as the actuator is moved relative to the housing.

4. The device of claim 3, further comprising a spring configured to restore the inner tubular member to a proximally withdrawn position following movement of the inner tubular member caused by the actuator.

5. The device of claim 1, wherein the actuator comprises an actuation member that slides axially relative to the housing, and wherein sliding the actuator along the housing moves the piston within the vacuum generation chamber.

6. The device of claim 5, wherein the actuation member is configured as a ring positioned around tubular portion of the housing.

7. The device of claim 1, further comprising a seal disposed within the tissue trap interior and configured for engaging and sealing the open proximal end of the inner tubular member when the inner tubular member is in a proximally withdrawn position relative to the outer tubular member.

8. The device of claim 1, wherein the distal portion of the outer tubular member is configured for insertion through a working channel of an endoscopic instrument for positioning the tissue resection window in an interior region of a patient's body.

9. The device of claim 1, further comprising a spring configured to restore the actuator to a non-actuated position following movement of the actuator.

10. A tissue removal device, comprising:
a housing;
an outer tubular member coupled to the housing and having a distal portion including a tissue resection window;
an inner tubular member slidably disposed within the outer tubular member and defining an inner lumen extending from an open distal end to an open proximal end, the open distal end comprising a cutting edge to sever tissue extending through the tissue resection window;
a vacuum generation chamber disposed in the housing including a movable piston disposed in the vacuum generation chamber;
a tissue trap disposed in or coupled to the housing, the tissue trap defining a sealed interior in fluid communication with the vacuum generation chamber via a one-way valve, so that air may be withdrawn from the tissue trap interior into the vacuum generation chamber by movement of the piston in a first direction, while air is prevented from entering the tissue trap interior from the vacuum generation chamber due to movement of the piston in a second direction opposite the first direction, wherein the open proximal end of the inner tubular member is disposed within the tissue trap interior;
an actuator moveably coupled to the housing by a pinned connection and operatively connected to the piston, such that rotation of the actuator about the pin moves the piston within the vacuum generation chamber; and
a first spring configured to restore the actuator to a non-actuated position following manual rotation of the actuator relative to the housing wherein the actuator is selectively operatively coupled to the inner tubular member such that movement of the actuator relative to the housing causes movement of the inner tubular member relative to the outer tubular member, wherein in a first configuration the actuator is not operatively coupled to the inner tubular member, and in a second configuration the actuator mechanically engages the inner tubular member such that movement of the actuator relative to the housing causes the open distal end of the inner tubular member to move distally across the tissue resection window as the actuator is moved relative to the housing.

11. The device of claim 10, wherein the actuator is selectively operatively coupled to the inner tubular member by a slider having a first position relative to the housing in which the actuator is not operatively coupled to the inner tubular member, and a second position relative to the housing in which the actuator mechanically engages the inner tubular member to cause the open distal end of the inner tubular member to move distally across the tissue resection window as the actuator is rotated relative to the housing.

12. The device of claims 10, further comprising a second spring configured to restore the inner tubular member to a proximally withdrawn position following movement of the inner tubular member caused by the actuator.

13. The device of claim 10, further comprising a seal disposed within the tissue trap interior and configured for engaging and sealing the open proximal end of the inner tubular member when the inner tubular member is in a proximally withdrawn position relative to the outer tubular member.

14. The device of claim 10, wherein the distal portion of the outer tubular member is configured for insertion through a working channel of an endoscopic instrument for positioning the tissue resection window in an interior region of a patient's body.

* * * * *